US012622644B2

(12) United States Patent
Adawi et al.

(10) Patent No.: US 12,622,644 B2
(45) Date of Patent: May 12, 2026

(54) OCCLUSION DETECTION VIA FLUID DILUTION

(71) Applicant: Biosense Webster (Israel) Ltd., Yokneam (IL)

(72) Inventors: Eid Adawi, Tur'an (IL); Shmuel Auerbach, Kerem Maharal (IL); Nakdimon Nissim Levy, Pardes Hana (IL); Eliyahu Ravuna, Kiryat Ata (IL); Iyar Rom, Givat Haim Ichud (IL); Shiran Eliyahu, Yokneam Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 388 days.

(21) Appl. No.: 16/720,514

(22) Filed: Dec. 19, 2019

(65) Prior Publication Data

US 2020/0205738 A1 Jul. 2, 2020

Related U.S. Application Data

(60) Provisional application No. 62/786,997, filed on Dec. 31, 2018, provisional application No. 62/786,957, filed on Dec. 31, 2018.

(51) Int. Cl.
A61B 5/00 (2006.01)
A61B 5/01 (2006.01)
(Continued)

(52) U.S. Cl.
CPC .............. A61B 5/6853 (2013.01); A61B 5/01 (2013.01); A61B 5/026 (2013.01); A61M 25/10 (2013.01);
(Continued)

(58) Field of Classification Search
CPC .. A61B 5/01; A61B 5/015; A61B 5/02; A61B 5/02007; A61B 5/026; A61B 5/027;
(Continued)

(56) References Cited

U.S. PATENT DOCUMENTS 6,391,024 B1 5/2002 Sun et al.
7,320,704 B2 1/2008 Lashinski et al.
(Continued)

OTHER PUBLICATIONS

Chinese First Office Action and Search Report dated Apr. 17, 2023, for Application No. 201911419596.8, 17 pages.
(Continued)

*Primary Examiner* — Eric J Messersmith
*Assistant Examiner* — Nidhi N Patel
(74) *Attorney, Agent, or Firm* — FBT Gibbons LLP

(57) ABSTRACT

A method of occlusion detection is disclosed. The method comprises the steps of positioning a medical tool coupled to a distal portion of a distal end of a delivery catheter at a target cavity within a patient. The medical tool includes an expandable balloon, and at least one sensor. The expandable balloon is expanded when positioned at the target cavity. The expandable balloon includes a membrane formed of a plurality of irrigation pores. Fluid is introduced into the target cavity either by injection or through the pores, or both. Using a sensor, a characteristic of blood is detected with the target cavity. The characteristic of blood is processed to determine the presence or absence of an occlusion within the cavity.

12 Claims, 35 Drawing Sheets

(51) Int. Cl.

| | |
|---|---|
| *A61B 5/026* | (2006.01) |
| *A61B 5/0538* | (2021.01) |
| *A61M 25/10* | (2013.01) |

(52) U.S. Cl.
CPC .... *A61B 5/0538* (2013.01); *A61M 2025/1052* (2013.01); *A61M 2025/1086* (2013.01); *A61M 2210/125* (2013.01)

(58) Field of Classification Search
CPC ....... A61B 5/028; A61B 5/053; A61B 5/0538; A61B 5/6853; A61B 5/14539; A61B 2018/00238; A61B 2018/00375; A61B 2018/00577; A61M 25/10; A61M 2025/1052; A61M 2025/1086; A61M 2210/125

See application file for complete search history.

(56) References Cited

U.S. PATENT DOCUMENTS

| | | | |
|---|---|---|---|
| 9,439,653 | B2 | 9/2016 | Avneri et al. |
| 9,468,485 | B2 | 10/2016 | Wittenberger et al. |
| 10,631,969 | B2 | 4/2020 | Edmiston et al. |
| 10,828,019 | B2 | 11/2020 | Goble et al. |
| 2006/0089637 | A1 | 4/2006 | Werneth et al. |
| 2008/0097422 | A1 | 4/2008 | Edwards et al. |
| 2011/0144637 | A1 | 6/2011 | Pageard et al. |
| 2013/0274712 | A1* | 10/2013 | Schecter ............... A61B 34/76 |
| | | | 604/100.01 |
| 2014/0276709 | A1 | 9/2014 | Wittenberger et al. |
| 2014/0276789 | A1 | 9/2014 | Dandler et al. |
| 2015/0265329 | A1* | 9/2015 | Lalonde ................. A61B 18/02 |
| | | | 606/21 |
| 2016/0157914 | A1 | 6/2016 | Avitall |
| 2016/0175041 | A1 | 6/2016 | Govari et al. |
| 2017/0347896 | A1 | 12/2017 | Keyes et al. |
| 2018/0140807 | A1* | 5/2018 | Herrera ................. A61B 6/485 |
| 2018/0161093 | A1 | 6/2018 | Basu et al. |

OTHER PUBLICATIONS

Chinese Second Office Action dated Sep. 27, 2023, for Application No. 201911419596.8, 16 pages.
Chinese Third Office Action and Search Report dated Mar. 20, 2024, for Application No. 201911419596.8, 11 pages.
Chinese Final Office Action and Search Report dated Jun. 4, 2024, for Application No. 201911419596.8, 13 pages.
European Partial Search Report and Written Opinion dated May 29, 2020, for Application No. 19220231.5, 11 pages.
European Extended Search Report and Written Opinion dated Sep. 2, 2020, for Application No. 19220231.5, 10 pages.
European Communication dated Dec. 6, 2022, for Application No. 19220231.5, 4 pages.
European Communication dated Dec. 7, 2023, for Application No. 19220231.5, 4 pages.
Japanese First Office Action dated Jul. 11, 2023, for Application No. 2019-237832, 5 pages.

\* cited by examiner

900

Position medical tool at a target cavity — 901

Expand the expandable balloon — 902

Inject a fluid inside the target cavity — 903

Detect, via at least one sensor, at least one characteristic of blood of the target cavity — 904

Process the at least one characteristic of blood detected by at least one sensor — 905

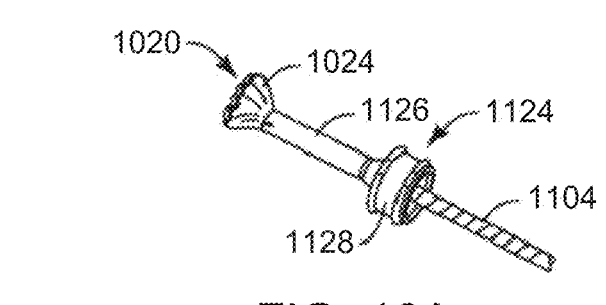
FIG. 16A
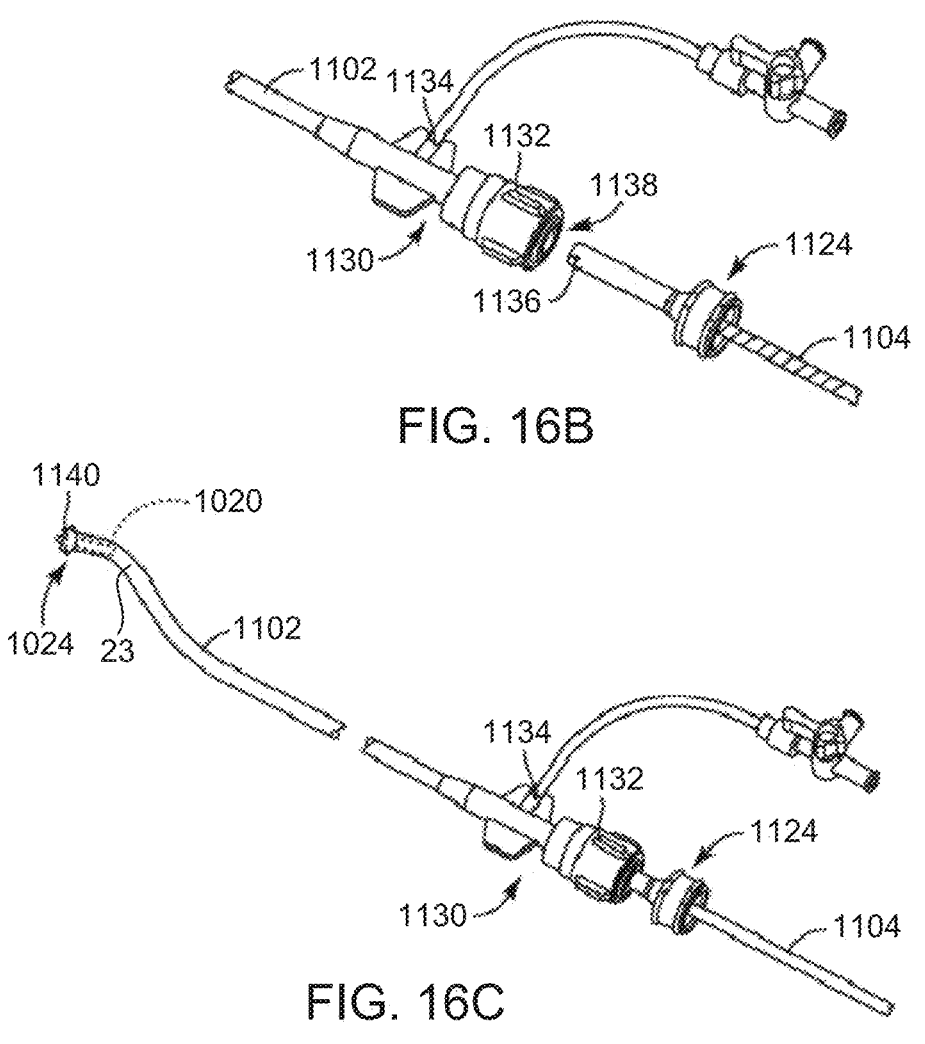
FIG. 16B
FIG. 16C

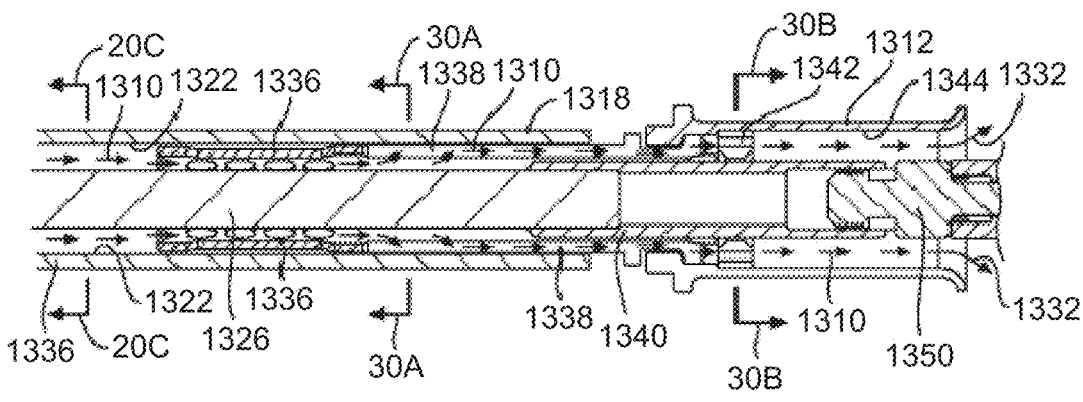
FIG. 30
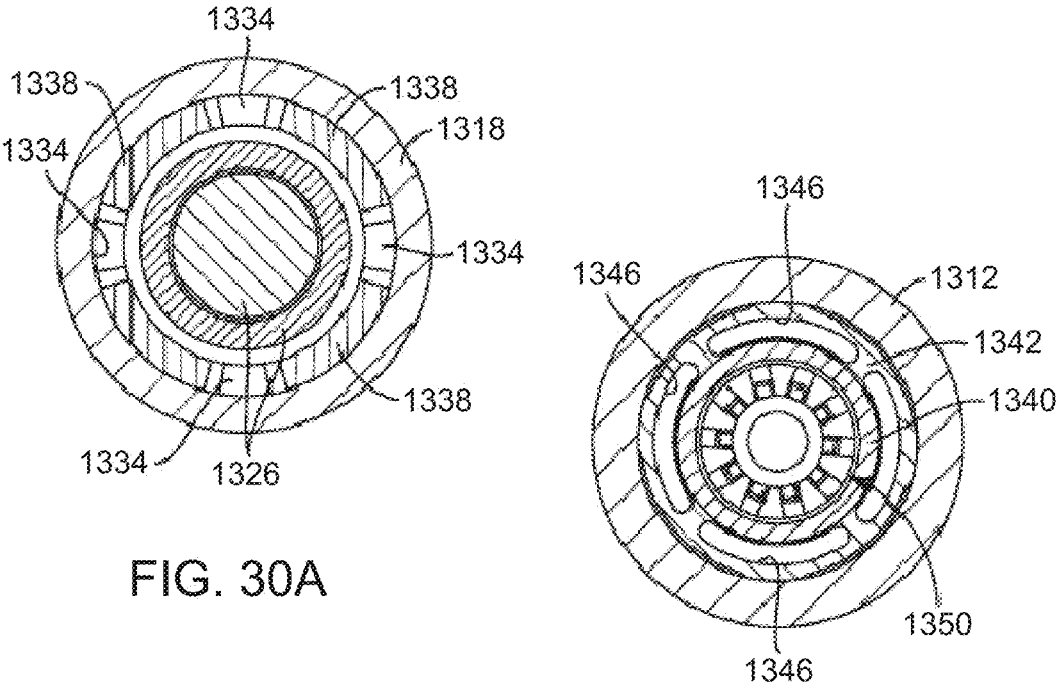
FIG. 30A
FIG. 30B

2200

| Position medical tool at a target cavity |
|---|

2201

| Deploy occluder portion of medical device |
|---|

2202

| Actuate anchor portion of medical device |
|---|

2203

| Inject a fluid inside target cavity |
|---|

2204

| Detect, via at least one sensor, at least one characteristic of blood of the target cavity |
|---|

2205

| Process the at least one characteristic of blood detected by at least one sensor |
|---|

2206

OCCLUSION DETECTION VIA FLUID DILUTION

CROSS-REFERENCE TO RELATED APPLICATIONS

This application claims the benefit of U.S. Provisional Application No. 62/786,957 filed on Dec. 31, 2018, and U.S. Provisional Application No. 62/786,997 filed on Dec. 31, 2018, the content of which are hereby incorporated by reference herein.

This application incorporates herein by reference as if fully set forth the contents of a non-provisional application titled Occlusion Detection By Pressure Measurement being filed on the same day as this application. That non-provisional application claims the benefit of U.S. Provisional Application No. 62/786,982 filed on Dec. 31, 2018. This application incorporates herein by reference as if fully set forth the contents of that provisional application.

BACKGROUND

The present invention concerns detecting occlusion within cavities of the heart using fluid dilution systems and methods. However, it should be understood that the systems, devices and methods of the present invention are not limited to use for detecting occlusion within cardiac cavities. In addition, the present invention could be used for determining occlusions in other parts of the body, such as blood clots in the brain. The fluid dilution systems, device and methods of the present invention are disclosed in two exemplary embodiments.

Under a first exemplary embodiment, the fluid dilution system, device and methods are used to detect occlusion of the pulmonary vein ("PV") or other heart cavities during ablation of cardiac tissue. Ablation of cardiac tissue has been used to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters may be visualized using fluoroscopy.

Under the second exemplary embodiment, the fluid dilution system, device and methods are used to detect occlusion of the left atrial appendage, or the left atrium as part of reducing the risk imposed by atrial fibrillation. The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

In general, occlusion is detected by injecting contrast fluid into a target cavity, e.g., the pulmonary vein or the left atrium, and observing whether the contrast fluid escapes from the target cavity. However, contrast fluid has several disadvantages, such as allergic reactions. It would therefore be advantageous to provide a system, method and/or device that is capable of occlusion detection in the pulmonary vein, the left atrial appendage, the left atrium, and other cavities of the heart, as well as in other parts of the human body, without use of contrast fluid.

SUMMARY

Under the first exemplary embodiment, a system, a device and methods for occlusion detection within the pulmonary vein are disclosed. The system for occlusion detection may include a sheath extending a length in a proximal-distal direction, the sheath including a tube defined by a sheath wall. The system also includes a delivery system including a catheter extending between proximal and distal ends, and a handle coupled to proximal end of the catheter, the catheter comprising an inner lumen. The system also includes a medical tool comprising an expandable balloon that may be coupled to the sheath. The expandable balloon includes distal and proximal ends defining a longitudinal axis. At least one sensor is configured to sense at least one characteristic of blood located within a target cavity, and at least one processor is configured to process the blood characteristic data acquired from the at least one sensor. Under the method, the medical tool is positioned at a target location within a portion of an organ of a patient. The method may include expanding the expandable balloon of the medical tool, injecting a fluid through an inner lumen of the catheter, detecting, via the at least one sensor, at least one characteristic of blood in the target cavity, and processing via the processor the at least one characteristic of blood. The presence or absence of an occlusion may be determined by the at least one characteristic of blood. Injecting a fluid, such as saline, may change the at least one characteristic of blood inside the target cavity. Therefore, changes in the at least one characteristic of blood may indicate the presence or absence of an occlusion.

Under the second exemplary embodiment, a system and method for detecting occlusion within the left atrial appendage, within the left atrium, within other cardiac cavities, or within other parts of the human body is disclosed. The system may include a sheath, a delivery system, a medical tool, at least one sensor and a processor. The sheath has a length and a sheath lumen extending through the length of the sheath. The delivery system may include a delivery catheter extending between a proximal end and a distal end, and a handle coupled to the proximal end of the delivery catheter. The medical tool is coupled to a distal end of the delivery catheter at a target location within a portion of an organ of a patient. The medical tool may include a hub including a bore defining an axis, and an occluder portion coupled to the hub. The occluder portion may be configured to be moved between a non-deployed position wherein the occluder portion is positioned within a distal portion of the sheath, and a deployed position upon the sheath being moved proximally relative to the occluder portion. An anchor portion may be provided that extends between a first end coupled to the handle and a second end pivotably coupled to a distal end of the occluder portion. Upon the occluder portion being maintained in the deployed position, the anchor portion is pivotable relative to the occluder portion between an anchor non-deployed position and an anchor deployed position. The at least one sensor may be configured to detect at least one physical characteristic of blood. The processor may be configured to process the blood characteristic data acquired from the at least one sensor. The system may be used to take measurements inside the left atrial appendage, the left atrium or both the left atrial appendage and the left atrium simultaneously.

The method of the second exemplary embodiment comprises positioning the medical tool at a target location within a portion of an organ of a patient. The medical tool may include an occluder portion, an anchor portion, a tissue growth member and a hub. The method includes deploying the occluder portion to the expanded, deployed position, actuating the anchor portion from the retracted position to the anchor deployed position, and injecting a fluid through the delivery catheter and through the hub of the medical tool, and into a target cavity. The tissue growth member prevents the fluid from exiting the cavity. The method includes detecting, via at the least one sensor, at least one characteristic of blood in the target cavity, and processing, via the processor, the at least one characteristic of blood data, wherein the presence or absence of an occlusion is determined by the at least one characteristic of blood. Injecting a fluid, such as saline, may change the at least one characteristic of blood inside the target cavity. Therefore, changes in the at least one characteristic of blood may indicate the presence or absence of an occlusion.

BRIEF DESCRIPTION OF THE DRAWINGS

FIGS. 16A-16C are perspective views of a loader, depicting the loader being pushed over an occluder portion of the medical tool, the medical tool inserted into a sheath, and pushed to a distal end of the sheath, respectively, according to the second exemplary embodiment of the present invention;

FIG. 30 is an enlarged cross-sectional view of the distal portion of the delivery system and the hub of the medical tool (with the occluder portion removed for simplification purposes), depicting a flow path of the fluid moving through the delivery system and hub of the medical tool, according to the second exemplary embodiment of the present invention;

FIG. 30A is an enlarged cross-sectional view taken from region 30A of FIG. 30, depicting the flow path for the fluid at a distal portion of the delivery system;

FIG. 30B is an enlarged cross-sectional view taken from region 30B of FIG. 20, depicting the flow path for the fluid at the hub of the medical tool;

DETAILED DESCRIPTION OF THE PREFERRED EMBODIMENTS

Figure 1:
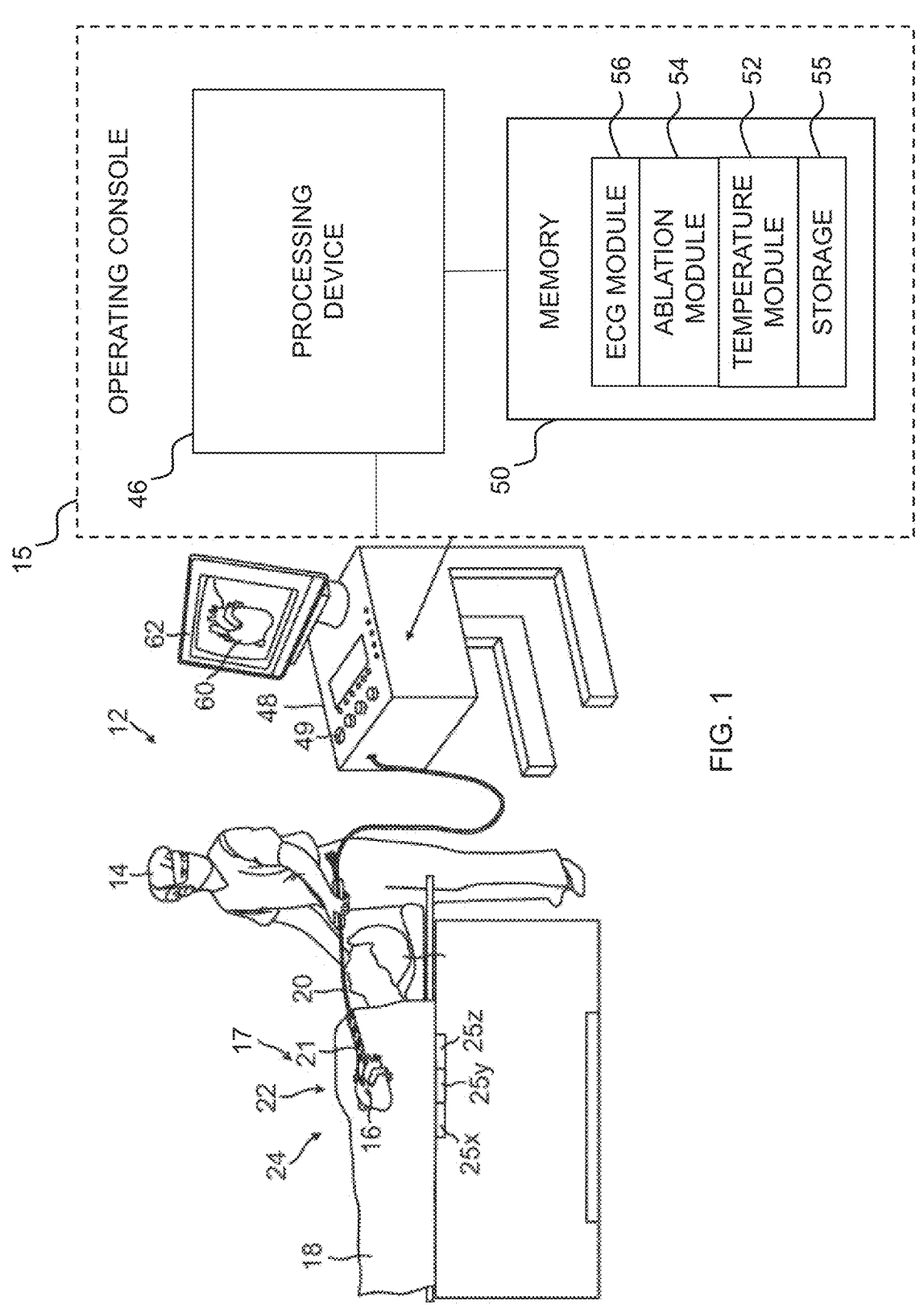
FIG. 1 is a schematic illustration of an invasive medical procedure in accordance with a first exemplary embodiment of the present invention including a medical tool having an expandable balloon.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. The phrase "distal" and "proximal" is used to indicate the spatial relationship of various components to the operator. For example, a distal component indicates that such component is further away in relation to the operator and a proximal component indicates that it is closer to the operator. In addition, as used herein, the terms "patient," "host," "user," and "subject" refer to any human or animal subject and are not intended to limit the systems or methods to human use, although use of the subject invention in a human patient represents a preferred embodiment.

Under the first exemplary embodiment, the system for occlusion detection may include a sheath having a tube defined by a sheath wall, the sheath extending a length in a proximal-distal direction. The system may also include a delivery system including a catheter extending between proximal and distal ends, and a handle coupled to the proximal end of the catheter, the catheter comprising an inner lumen. The system also includes a medical tool comprising an expandable balloon that may be coupled to the sheath. The expandable balloon may include distal and proximal ends defining a longitudinal axis. At least one sensor configured to sense at least one characteristic of blood located of the target cavity, and at least one processor is configured to process the blood characteristic data acquired from the at least one sensor.

Under the first exemplary embodiment, the at least one sensor may be a temperature sensor. The at least one temperature sensor may be located one or more of the distal end of the balloon, the proximal end of the balloon, or the distal end of the catheter and the proximal end of the catheter. The at least one temperature sensor may comprise a first temperature sensor and a second temperature sensor, the first temperature sensor being located on the distal end of the balloon and the second temperature sensor being located on the proximal end of the balloon. The distal end of the catheter may comprise a lasso portion that extends through the distal portion of the balloon, and the at least one temperature sensor may be located on one or more of the distal end of the balloon, the proximal end of the balloon and the lasso portion of the catheter. The distal end of the catheter may comprise a lasso portion that extends through the distal portion of the balloon, and the at least one temperature sensor may comprise a first temperature sensor and a second temperature sensor, the first temperature sensor being located on the proximal end of the balloon and the second temperature sensor being located on the lasso portion of the catheter.

The at least one sensor may be at least two electrodes. The at least two electrodes may be located on one or more of the distal end of the balloon and the proximal end of the balloon. The at least two electrodes may be located on one or more of a distal end of the balloon, a proximal end of the balloon, the distal end of the catheter and the proximal end of the catheter. The distal end of the catheter may comprise a lasso portion that extends through the distal portion of the balloon, and the at least two electrodes are located on one or more of a distal end of the balloon, a proximal end of the balloon, and the lasso portion of the catheter. The distal end of the catheter may comprise a lasso portion that extends through the distal portion of the balloon, and the at least one sensor may comprise a first electrode and a second electrode, the first electrode being located on one of a distal end of the balloon, a proximal end of the balloon or the lasso portion of the catheter, and the a second electrode being a reference electrode.

The at least one sensor may be a pH sensor.

The processor may be further configured to record measurements of the at least one characteristic of blood over time. The system may further comprise a memory configured to store the measurements of the at least one characteristic of blood over time. The system may further comprise a display configured to display a baseline characteristic of blood next to, or on top of, the at least one characteristic of blood over time.

The processor may be further configured to determine whether an occlusion is present by comparing at least one blood characteristic data over time to a baseline of the at least one characteristic of blood. Additionally or alternatively, the processor may be further configured to determine whether an occlusion is present in the target cavity based on how quickly the at least one characteristic of blood returns to its original value after the fluid is injected.

Under the method of the first exemplary embodiment, the medical tool, coupled to a distal portion of a distal end of a catheter, may be positioned at a target location within a portion of an organ of a patient. The method may include expanding the expandable balloon when the balloon is positioned at the target location, injecting a fluid through an inner lumen of the delivery catheter, and detecting, via the at least one sensor, at least one characteristic of blood in the target cavity, processing, via a processor, the at least one characteristic of blood, wherein the presence or absence of an occlusion is determined by the at least one characteristic of blood.

The target cavity is one of a pulmonary vein or left atrium. The fluid that is injected may be a coolant, such as saline or glucose at low temperature. The at least one sensor may be a temperature sensor and the at least one characteristic of blood is temperature. The at least one sensor may be a first electrode and a second electrode and the at least one characteristic is bipolar electrical impedance. The at least one sensor may be a first electrode and a second electrode, the second electrode being a reference electrode, and the at least one blood measurement is unipolar electrical impedance. The at least one sensor may be a pH sensor, and the at least one characteristic of blood may be pH.

A baseline pressure of the at least one characteristic of blood may be determined by positioning the medical tool at a target location within a portion of an organ of a patient, expanding the expandable balloon when the balloon is positioned at the target location, injecting a fluid into a target cavity without an occlusion through an inner lumen of the delivery catheter, and detecting, via the at least one sensor, at least one characteristic of blood in the target cavity, and processing, via a processor, the at least one characteristic of blood data and establishing the data as a baseline measurement.

The method may further comprise recording, via the processor, the at least one characteristic of blood over time. The method may further comprise storing, in a memory, measurements of the at least one blood characteristic over time. The presence or absence of an occlusion may be determined by comparing the baseline of the at least one baseline blood measurement and the at least one blood measurement detected by the at least one sensor over time. The method may further comprise determining, via a processor, the presence or absence of an occlusion by comparing the baseline of the at least one characteristic of blood and the detected at least one characteristic of blood over time. Additionally or alternatively, the processor may be further configured to determine whether an occlusion is present in the target cavity based on how quickly the at least one characteristic of blood returns to its original value after the fluid is injected.

The present invention discloses a system and method for detecting occlusion within the pulmonary vein, within the left atrial appendage, or within other cardiac cavities or other areas of the human body. The occlusions to be detected may be the result of positioning a medical tool within a cardiac cavity for the purpose of achieving an occlusion, or may be the result of coronary artery blockages, or blood clots in the brain. A method is disclosed where a coolant, e.g. a saline or glucose maintained at a low temperature, is injected, while a balloon catheter is positioned in the pulmonary vein ostium and temperature change is monitored inside the pulmonary vein or other cavity, using a temperature sensor located on the balloon distal or proximal location, and/or on a diagnostic guide wire, e.g., lasso, extending from the balloon, to identify whether occlusion has been achieved or discovered. Instead of a coolant, any fluid that changes blood characteristics may be used. For example, impedance, pH or chemical composition of the blood may be measured instead of the temperature. Alternatively or additionally, any two electrodes located on the balloon distal part and/or proximal part and/or the diagnostic guide wire, e.g., lasso, may be used for measuring impedance (bipolar or unipolar). Alternatively or additionally, a pH sensor or some other sensor to detect changes in the chemical composition of the blood could be employed for measuring changes in these blood characteristics. Also disclosed is a method to inject the coolant fluid without occlusion in order to measure a baseline of a specific patient at the relevant anatomical location (for example inside the pulmonary vein), and then to use the baseline as a reference for full/partial occlusion identification. Also disclosed is a method to show the baseline of thermal dilution and the current thermal dilution, side-by-side, or one on top of the other, to enable the physician to understand whether an occlusion exists. Also disclosed is a method to automatically compare the baseline of thermal dilution and the current thermal dilution, to identify occlusion. Also disclosed is a method to identify occlusion automatically by analyzing the dilution pattern of the temperature (without any baseline). If the temperature is increasing steadily, occlusion may be assumed. While, if temperature is increasing in waves synchronized with the heart-beats, occlusion may not necessarily be assumed. FIG. 1 is a schematic illustration of an invasive medical procedure using apparatus 12, according to a first exemplary embodiment. The procedure is performed by a medical professional 14, and, by way of example, the procedure in the description hereinbelow is assumed to comprise ablation of a portion of a myocardium 16 of the heart of a human patient 18. However, it is understood that embodiments disclosed herein are not merely applicable to this specific procedure, and may include substantially any procedure on biological tissue or on non-biological materials.

Figure 2:
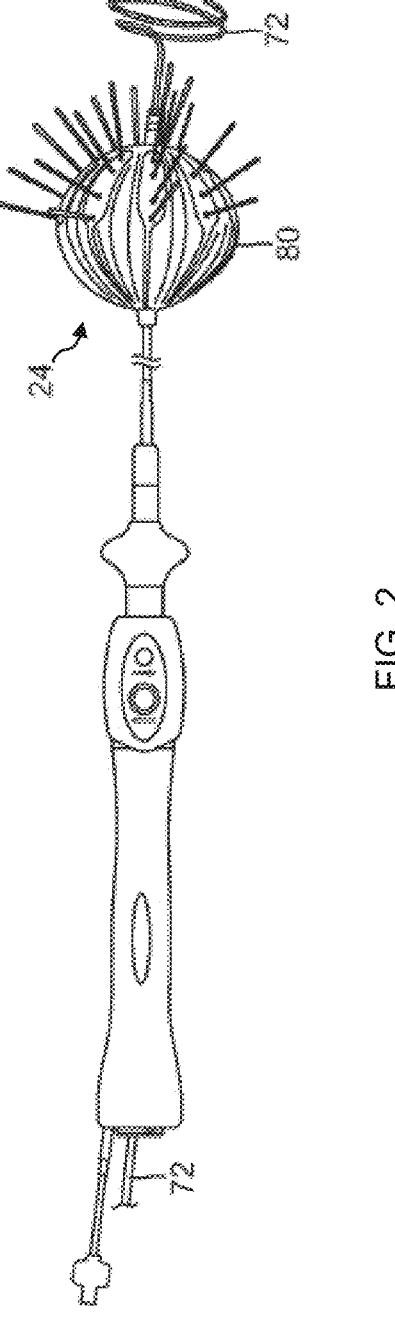
FIG. 2 is a top view of a catheter with the balloon of the first exemplary embodiment in an expanded state, in use with a lasso catheter extending from the distal portion of the balloon.

To perform the ablation, medical professional 14 inserts a probe 20 into a sheath 21 that has been pre-positioned in a lumen of the patient. The sheath 21 may include a tube defined by a sheath wall, the sheath extending a length in a proximal distal direction. Sheath 21 is positioned so that a distal end 22 of probe 20 enters the heart of the patient. A medical tool 24, which is described in more detail below with reference to FIG. 2, is deployed through a lumen 17 of the probe 20, and exits from a distal end of the probe 20.

As shown in FIG. 1, apparatus 12 is controlled by a processing device 46, which is in an operating console 15 of the apparatus. The apparatus console 15 may include controls 49 which are used by professional 14 to communicate with the processing device 46. During the procedure, the processing device 46 typically tracks a location and an orientation of the distal end 22 of the probe 20, using any method known in the art. For example, the processing device 46 may use a magnetic tracking method, wherein magnetic transmitters 25X, 25Y and 25Z external to the patient 18 generate signals in coils positioned in the distal end of the probe 20. The CARTO® system (available from Biosense Webster, Inc. of Irvine, California) uses such a tracking method.

The software for the processing device 46 may be downloaded to the processing device 46 in electronic form, over a network, for example. Additionally or alternatively, the software may be provided on non-transitory tangible media, such as optical, magnetic, or electronic storage media. The tracking of the distal end 22 may be displayed on a three-dimensional representation 60 of the heart of the patient 18 on a display device 62. However, it may be displayed two-dimensionally, e.g., by fluoroscopy or MRI.

Figure 3:
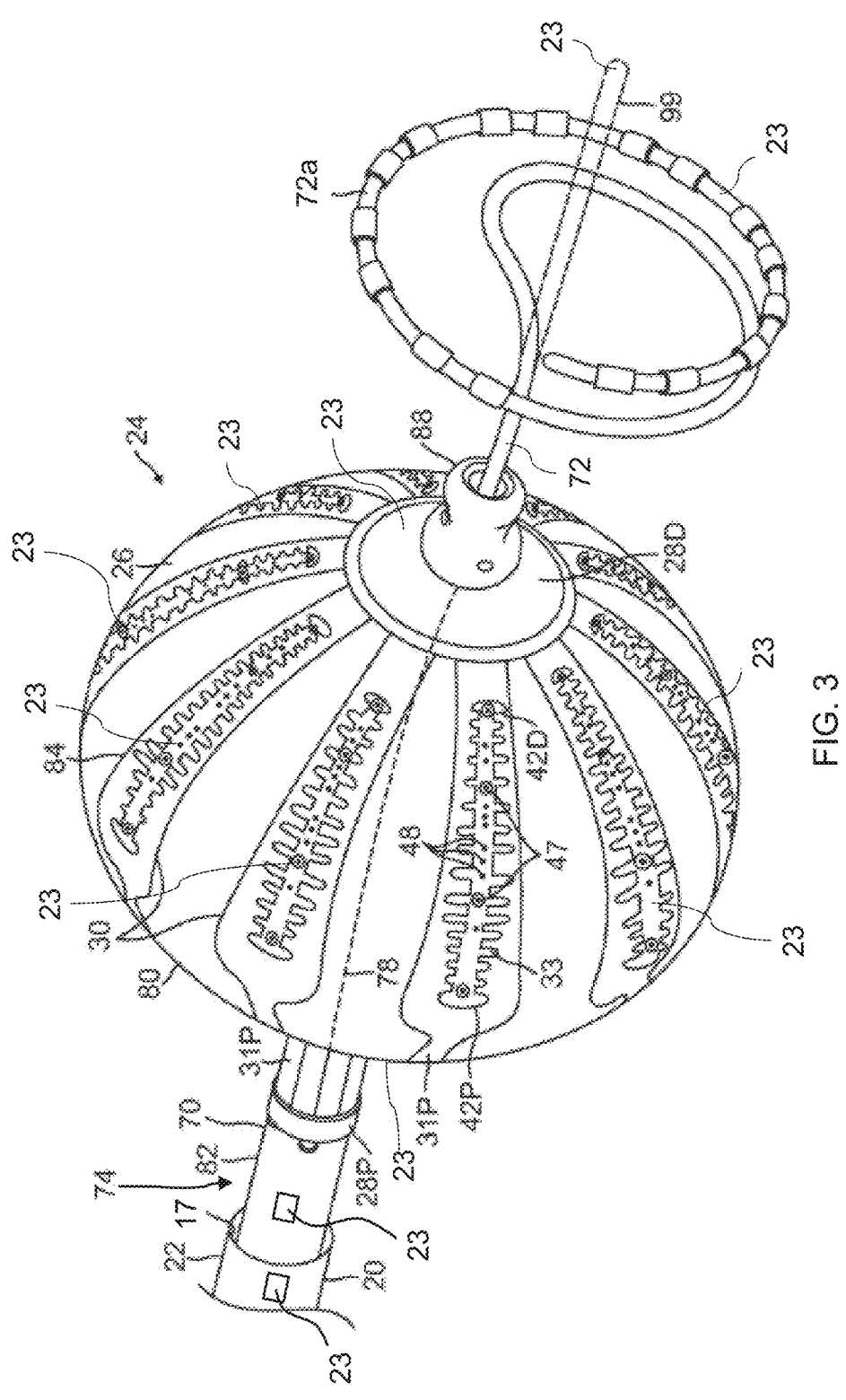
FIG. 3 is a perspective view of a balloon of FIG. 2, along with the lasso catheter extending from the distal portion of the balloon.
Figure 4:
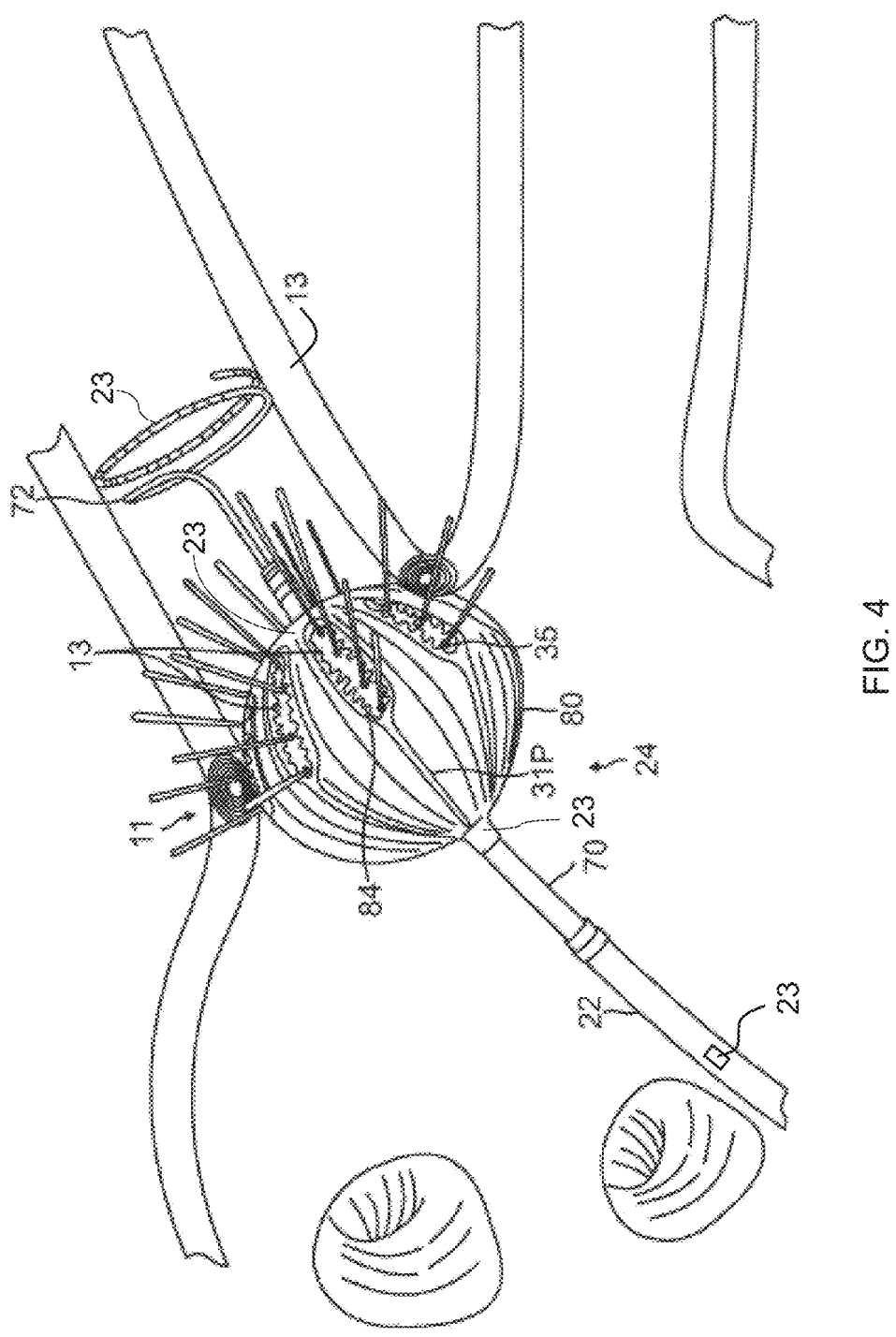
FIG. 4 is a side view of a distal end of the catheter of FIG. 2 deployed in the region of a pulmonary vein and its ostium.
Figure 5:
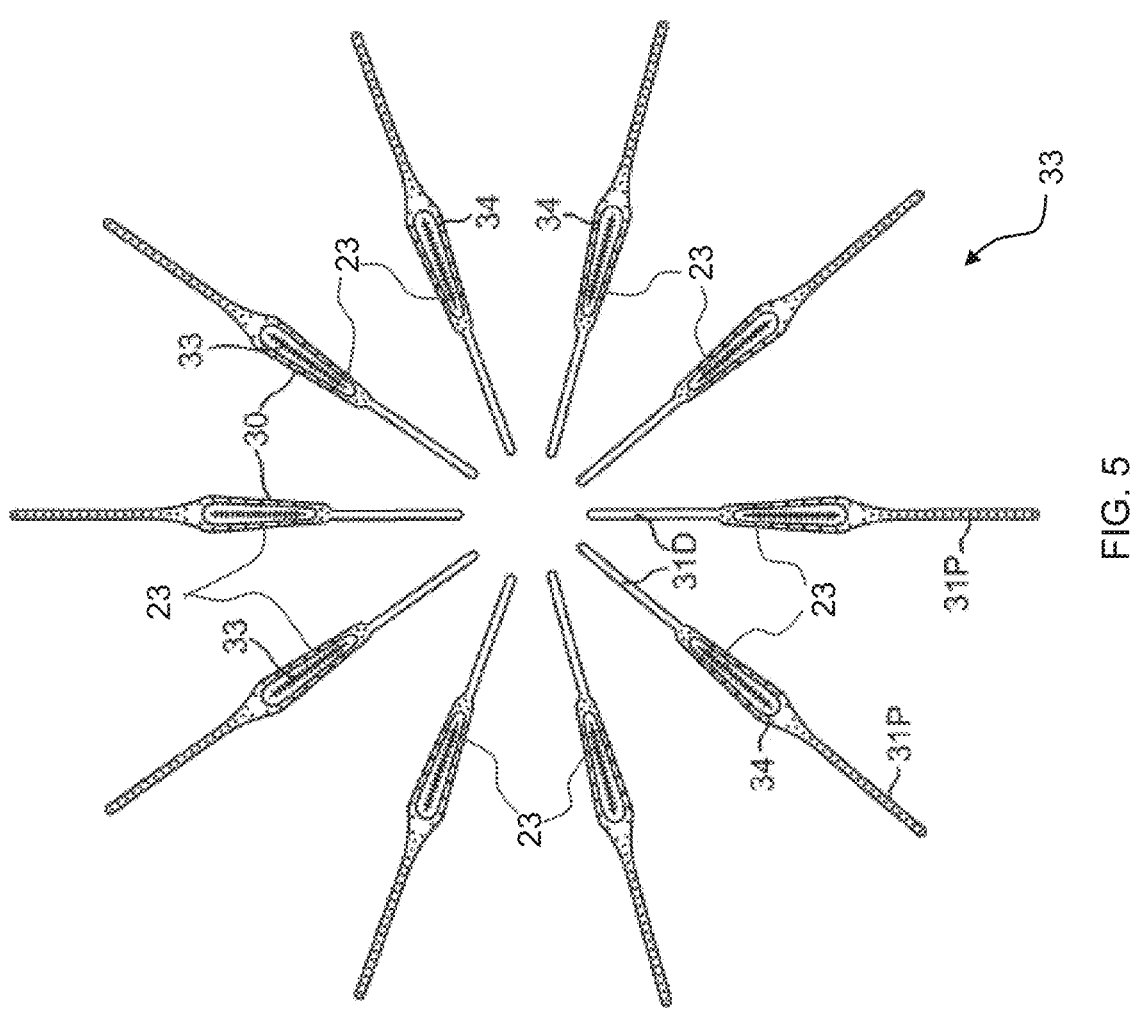
FIG. 5 is a top plan view of a plurality of flex circuit electrode assemblies prior to being assembled onto the balloon of FIG. 3, with the electrode of each assembly including a sensor for sensing a blood characteristic such as temperature, impedance, or pH, the sensor located in the center of each electrode.

To operate apparatus 12, the processing device 46 communicates with a memory 50, which has many modules used by the processor to operate the apparatus. Thus, the memory 50 may include a temperature module 52, an ablation module 54, and an electrocardiograph (ECG) module 56, the functions of which are described below. The memory 50 typically may include other modules, such as a force module for measuring the force on the distal end 22, a tracking module for operating the tracking method used by the processing device 46, and an irrigation module allowing the processor to control irrigation provided for the distal end 22. For simplicity, such other modules are not illustrated in FIG. 1. The modules may comprise hardware as well as software elements. For example, module 54 may include a radio-frequency generator with at least one output or output channel, e.g., ten outputs or ten output channels. Each of the outputs may be separately and selectively activated or deactivated by a switch. That is, each switch may be disposed between the signal generator and a respective output. Thus, a generator with ten outputs would include ten switches. These outputs may each be individually coupled to electrodes on an ablation catheter, e.g., the ten electrodes 33 on balloon 80, described in further detail below. Such an electrical connection may be achieved by establishing an electrical path between each output and each electrode. For example, each output may be connected to a corresponding electrode by one or more wires or suitable electrical connectors. Thus, in some embodiments, an electrical path may include at least one wire. In some embodiments, the electrical path may further include an electrical connector and at least a second wire. Thus, electrodes 33 may be selectively activated and deactivated with the switches to receive radiofrequency energy separately from each of the other electrodes. As best illustrated in FIG. 5, at the center of each electrode 33 there may be located a sensor 23 for sensing parameters such as temperature, impedance and/or pH. It should be understood that the center of the electrode 33 is merely an exemplary location, and the sensor 23 may be located at any location on the surface of the electrode 33. For example, the sensor 23 may be a thermocouple for sensing temperature. Memory 50 may further comprise storage 55 for storing data. The memory 50 may include any volatile and/or non-volatile memory, such as random-access memory or a hard disk drive FIG. 3 is a schematic perspective view of the medical tool 24 in an expandable configuration in the form of a balloon 80 in its expanded configuration. The medical tool 24 is used to ablate an ostium 11 of a lumen, such as a pulmonary vein 13, as shown in FIG. 4, and the medical tool 24 is supported by a tubular shaft 70 having a proximal shaft portion 82 and a distal shaft end 88. The shaft 70 includes a hollow central tube 74, which permits a delivery catheter 72 to pass therethrough and past the distal shaft end 88. The delivery catheter 72 may be a focal linear catheter 99 (shown in broken lines in FIG. 3) or a lasso catheter 72, as illustrated in solid lines in FIG. 3. The lasso catheter 72 may be inserted into the pulmonary vein 13 to position the medical tool 24 correctly with respect to the ostium 11 (FIG. 4) prior to ablation of the ostium 11 (FIG. 4). The distal lasso portion 72a of the catheter 72 is typically formed of shape-memory retentive material such as nitinol. It is understood that the medical tool 24 may also be used with a linear or focal catheter 99 (as shown in broken lines in FIG. 3) in the pulmonary vein or elsewhere in the heart. The focal catheter 99 may include a force sensor (not shown) at its distal tip. As such, a delivery system may include a delivery catheter coupled to a handle with the medical tool 24 operatively coupled to the handle at a distal end of the delivery catheter. The delivery catheter may comprise an inner lumen through which fluid, such as saline, may flow. Any catheter used in conjunction with the diagnostic/therapeutic catheter may have features and functions, including, for example, pressure sensing, ablation, diagnostic, e.g., navigation and pacing.

The balloon 80 of the medical tool 24 has an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed configuration, via the lumen 17 of the probe 20, and may be expanded after exiting from the distal end 22. The membrane 26 of the balloon 80 is formed with irrigation pores or apertures 27 (shown in FIG. 6) through which the fluid (e.g., saline) can exit from the interior of the balloon 80 to outside the balloon for cooling the tissue ablation site at the ostium 11. While FIG. 2 and FIG. 4 show fluid exiting the balloon 80 as jet streams, it is understood that the fluid may exit the balloon with any desired flow rate or pressure, including a rate where the fluid is seeping out of the balloon.

Figure 5A:
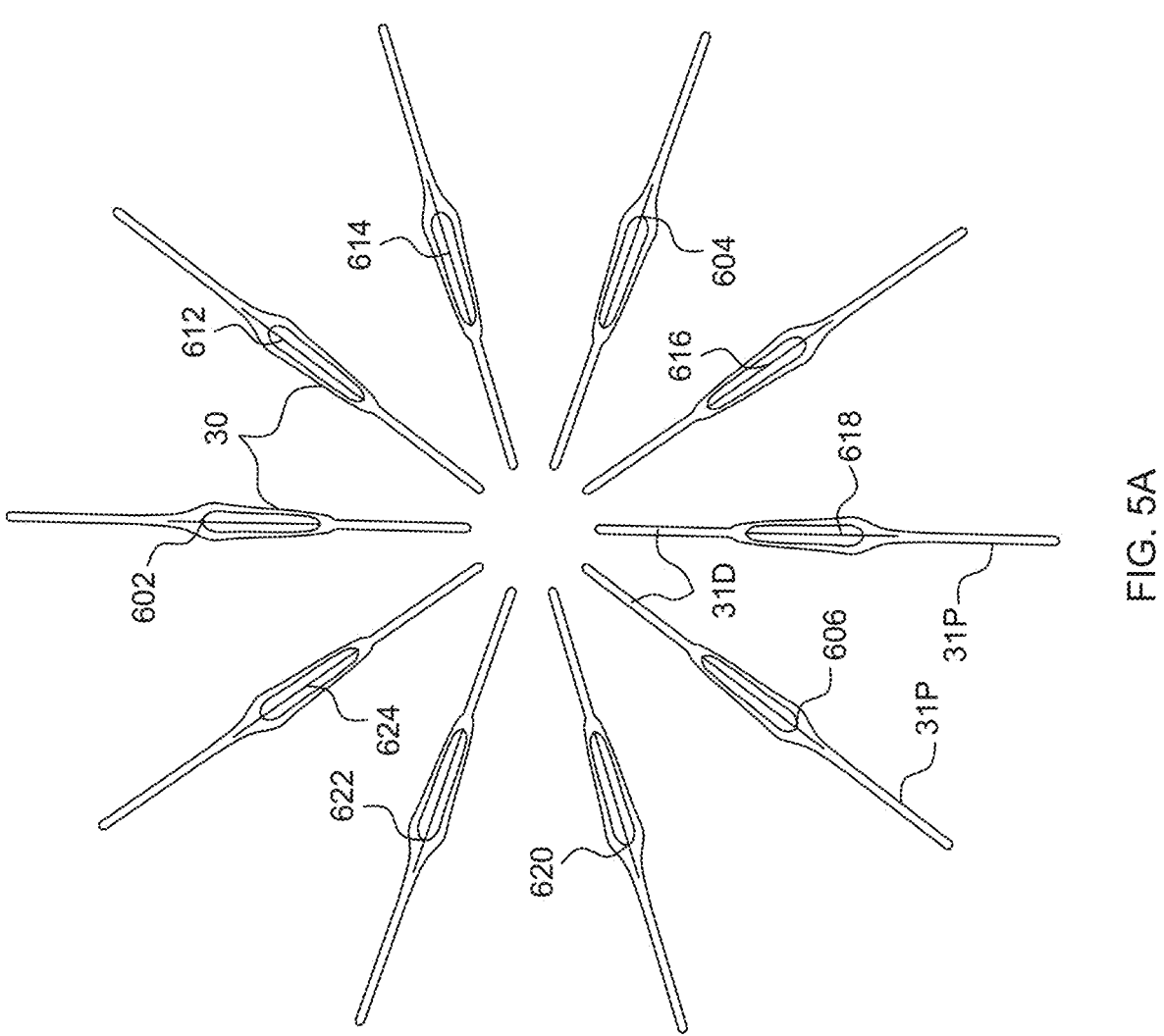
FIG. 5A is a top plan view of a plurality of flex circuit electrode assemblies that includes radiopaque markers prior to being assembled onto the balloon of FIG. 3.
Figure 5B:
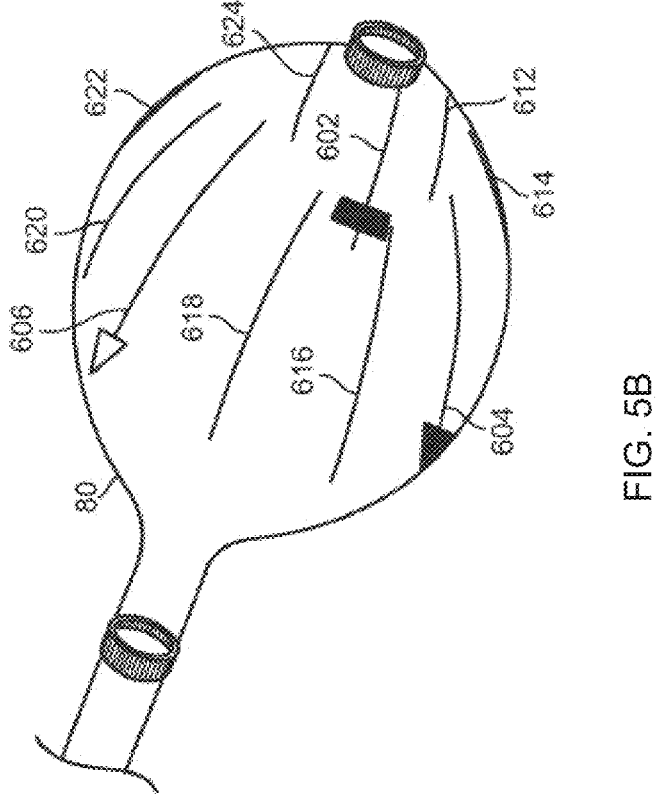
FIG. 5B is a representation of a fluoroscopic image of the balloon of FIG. 3 that includes the flex circuit electrode assemblies of FIG. 5A.

The membrane 26 supports and carries a combined electrode and a multi-layer flexible circuit electrode assembly 84. The "flex circuit electrode assembly" 84 may have many different geometric configurations. As best seen in FIG. 5, the flex circuit electrode assembly 84 has a plurality of radiating substrates or strips 30 on which electrodes 33 are disposed. In the center of each electrode 33 a sensor 23 may be positioned. The substrates 30 are evenly distributed about the distal end 88 and the balloon 80. Each substrate 30 has wider proximal portion that gradually tapers to a narrower distal portion. Alternatively or additionally, as shown in FIG. 5A the substrates 30 of flex circuit electrode assembly 84 may incorporate radiopaque markers (e.g., 602, 604, 606), which will be described in greater detail below. In FIG. 5A, electrodes 33 and other details shown in FIG. 5A have been hidden for clarity.

With reference to FIGS. 3, 5, and 5A, each substrate 30 has a proximal tail 31P and a distal tail 31D. The proximal tail 31P is tucked under and fastened to the medical tool 24 by a proximal ring 28P mounted on the proximal shaft portion 82 of the shaft 70. The distal tail 31D is tucked under and fastened to the medical tool 24 by a distal ring (not shown). Either or both sets of tails 31D and 31P may be further covered by a respective semispherical cap, such as distal cap 28D. One or more electrodes 33 on each substrate come into galvanic contract with the ostium 11 during an ablation procedure, during which electrical current flows from the electrodes 33 to the ostium 11, as shown in FIG. 4.

Figure 6:
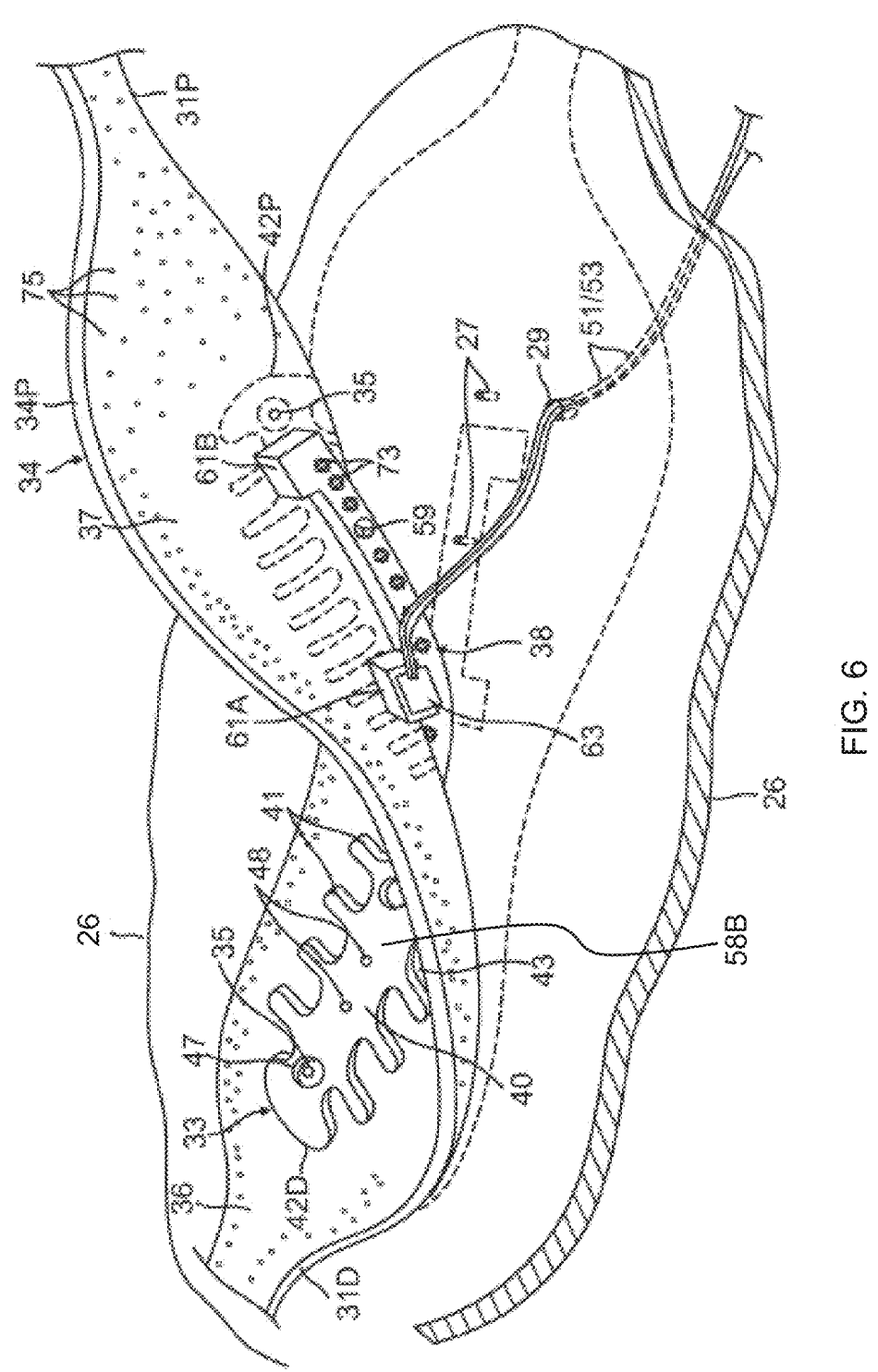
FIG. 6 is a perspective detail view of a flex circuit electrode assembly after being assembled on the balloon of FIG. 3.

For simplicity, the flex circuit electrode assembly 84 (FIG. 3) is described with respect to one of its substrates 30 as shown in FIG. 6, although it is understood that following description may apply to each substrate 30 of the assembly 84. Referring now to FIG. 6, the flex circuit electrode assembly 84 includes a flexible and resilient sheet substrate 34, constructed of suitable bio-compatible materials, for example, polyimide. The sheet substrate 34 may have a greater heat resistance (or a higher melting temperature) compared to that of the balloon membrane 26. Alternatively or additionally, the substrate 34 may be constructed of a thermoset material having a decomposition temperature that is higher than the melting temperature of the balloon membrane 26 by approximately 100 degrees Celsius or more.

The substrate 34 is formed with one or more irrigation pores or apertures 35 that are in alignment with the irrigation apertures 27 of the balloon member 26 so that fluid passing through the irrigation apertures 27 and 35 can pass to the ablation site on the ostium.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium 11. On its inner surface 37, the substrate 34 supports and carries a wiring electrode 38. The contact electrode 33 delivers RF energy to the ostium 11 during ablation or is connected to a thermocouple junction for temperature sensing of the ostium 11. In the illustrated first exemplary embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 may resemble a "fishbone" but it should be noted that the invention is not limited to such configuration. In contrast to an area or "patch" ablation electrode, the fingers 41 of the contact electrode 33 advantageously increase the circumferential or equatorial contact surface of the contact electrode 33 with the ostium 11 while void regions 43 between adjacent fingers 41 advantageously allow the balloon 80 to collapse inwardly or expand radially as needed at locations along its equator. In the illustrated first exemplary embodiment, the fingers 41 have different lengths, some being longer, others being shorter. For example, the plurality of fingers 41 includes a distal finger, a proximal finger and fingers therebetween, where each of the fingers 41 in between has a shorter adjacent finger. For example, each finger 41 has a length different from its distal or proximal immediately adjacent neighboring finger(s) 41 such that the length of each finger generally follows the tapered configuration of each substrate 30.

In the illustrated first exemplary embodiment, there are 22 fingers extending across (past each lateral side of) the elongated portion 40, with the longest finger being the third finger from the enlarged proximal end 42P. The contact electrode 33 may include gold 58B with a seed layer between the gold 58B and the membrane 26. The seed layer may include titanium, tungsten, palladium, silver, or combinations thereof.

Formed within the contact electrode 33 are one or more exclusion zones 47, each surrounding an irrigation aperture 35 formed in the substrate 34. The exclusion zones 47 are voids purposefully formed in the contact electrode 33, as explained in detail further below, so as to avoid damage to the contact electrode 33 during construction of the electrode assembly 84 in accommodating the irrigation apertures 35 at their locations and in their function.

Also formed in the contact electrode 33 are one or more conductive blind vias 48 which are conductive or metallic formations that extend through through-holes in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

In the illustrated first exemplary embodiment, the contact electrode 33 measures longitudinally between about 0.1 inch and 1.0 inch, and preferably between about 0.5 inch and 0.7 inch, and more preferably about 0.57 inch, and has four exclusion zones 47 and nine blind vias 48.

On the inner surface 37 of the substrate 34, the wiring electrode 38 is generally configured as an elongated body generally similar in shape and size to the elongated portion 40 of the contact electrode 33. The wiring electrode 38 loosely resembles a "spine" and also functions as a spine in terms of providing a predetermined degree of longitudinal rigidity to each substrate 30 of the electrode assembly 84. The wiring electrode 38 is positioned such that each of the blind vias 48 is in conductive contact with both the contact electrode 33 and the wiring electrode 38. In the illustrated first exemplary embodiment, the two electrodes 33 and 38 are in longitudinal alignment with other, with all nine blind vias 48 in conductive contact with both electrodes 33 and 38. The wiring electrode 38 may have an inner portion of copper 57 and an outer portion of gold 58.

The wiring electrode 38 is also formed with its exclusion zones 59 around the irrigation apertures 35 in the substrate 34. The wiring electrode 38 is further formed with solder pad portions 61, at least one active 61A, and there may be one or more inactive solder pad portions 61B. The solder pad portions 61A and 61B are extensions from a lateral side of the elongated body of the wiring electrode 38. In the illustrated first exemplary embodiment, an active solder pad portion 61A is formed at about a mid-location along the elongated body, and a respective inactive solder pad portion 61B is provided at each of the enlarged distal end 42D and the enlarged proximal end 42P.

Attached, e.g., by a solder weld 63, to the active solder pad portion 61A are the wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63. The wire pair 51/53 are passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28.

The flex circuit electrode assembly 84, including the substrates 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26. The irrigation apertures 35 in the substrate 34 are aligned with the irrigation apertures 27 in the balloon membrane 26. The exclusion zones 59 in the wiring electrode 38 and the exclusion zones 47 in the contact electrode 33 are concentrically aligned with each other, as well as with the irrigation apertures 27 and 35 in balloon 26 and substrate 34, respectively.

Figure 7:
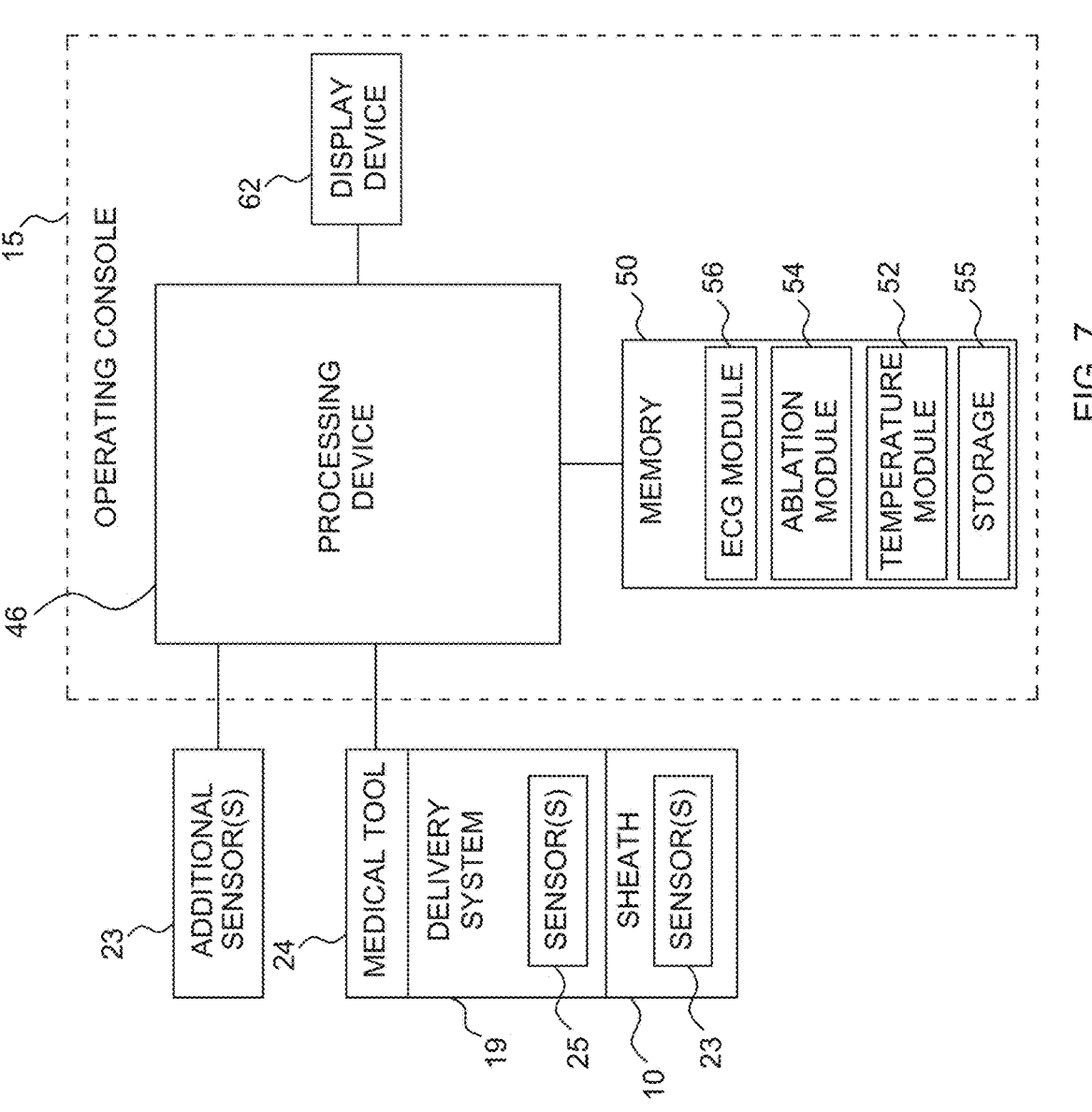
FIG. 7 is a block diagram illustrating example components of a medical tool for occlusion detection of the first exemplary embodiment of the invention.
Figure 8:
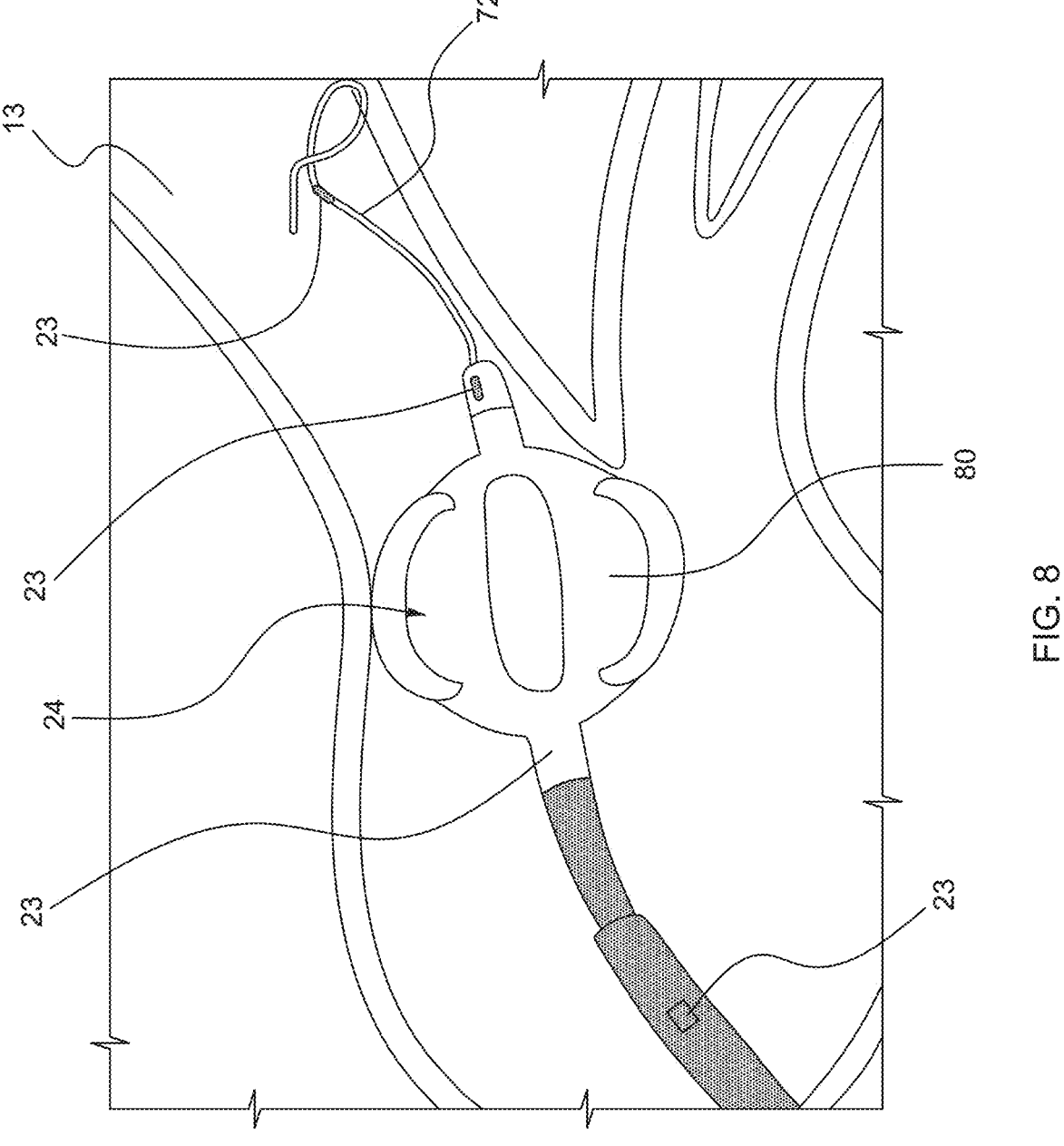
FIG. 8 is a side view of a medical tool of the first exemplary embodiment of the invention located in proximity to the pulmonary vein.

With reference to FIGS. 7 and 8, a system 700 for occlusion detection may comprise a sheath 102, a delivery system 19, a medical tool 24 including a balloon 80 and a processing device 46, as described above, and at least one sensor 23. The system may further comprise a memory 50 and a display device 62, as described above. The processing device 46, memory 50 and display device 62 may be part of operating console 15. The system may optionally comprise additional sensors 23 located throughout the system 700, as described below. The operating console 15 may also include an I/O interface.

The at least one sensor 23 may be configured to detect at least one physical characteristic of blood. As an example, the at least one sensor 23 may be a temperature sensor 23, e.g., a thermocouple. Referring now to FIGS. 3, 4 and 8, under the first exemplary embodiment, the at least one temperature sensor 23 may be located one or more of the distal end of the balloon 80, the proximal end of the balloon 80, the distal end of the catheter 72 and the proximal end of the catheter 72 or on the center of each electrode 33. The at least one temperature sensor 23 may comprise a first temperature sensor 23 and a second temperature sensor 23, the first temperature sensor 23 being located on the distal end of the balloon 80 and the second temperature sensor 23 being located on the proximal end of the balloon 80. The distal end of the catheter 72 may comprise a lasso portion 72a that extends through the distal portion of the balloon 80, as described above, and the at least one temperature sensor 23 may be located on one or more of the distal end of the balloon 80, the proximal end of the balloon 80 and the lasso portion 72a of the catheter 72. The distal end of the catheter 72 may comprise a lasso portion 72a that extends through the distal portion of the balloon 80, as described above, and the at least one temperature sensor 23 may comprise a first temperature sensor 23 and a second temperature sensor 23, the first temperature sensor 23 being located on the proximal end of the balloon 80 and the second temperature sensor 23 being located on the lasso portion 72a of the catheter 72, as shown in FIG. 8. Alternatively or additionally, under the first exemplary embodiment, the at least one sensor 23 may be at least two electrodes. The at least two electrodes may be located on one or more of the distal end of the balloon 80 and the proximal end of the balloon 80. Alternatively or additionally, the at least two electrodes may be located on one or more of a distal end of the balloon 80, a proximal end of the balloon 80, the distal end of the catheter 72a and the proximal end of the catheter 72. The distal end of the catheter 72 may comprise a lasso portion 72a that extends through the distal portion of the balloon 80, and the at least two electrodes may be located on one or more of a distal end of the balloon 80, a proximal end of the balloon 80, and the lasso portion 72a of the catheter 72. Alternatively or additionally, the distal end of the catheter 72 may comprise a lasso portion 72a that extends through the distal portion of the balloon 80, and the at least one sensor 23 may comprise a first electrode and a second electrode, the first electrode being located on one of a distal end of the balloon 80, a proximal end of the balloon 80 or the lasso portion 72a of the catheter 72, and the a second electrode being a reference electrode.

Alternatively or additionally, the at least one sensor 23 may be a pH sensor.

The processing device 46 may be further configured to record measurements of the at least one characteristic of blood over time. The system 700 further may include memory 50 configured to store the measurements of the at least one characteristic of blood.

Figure 8A:
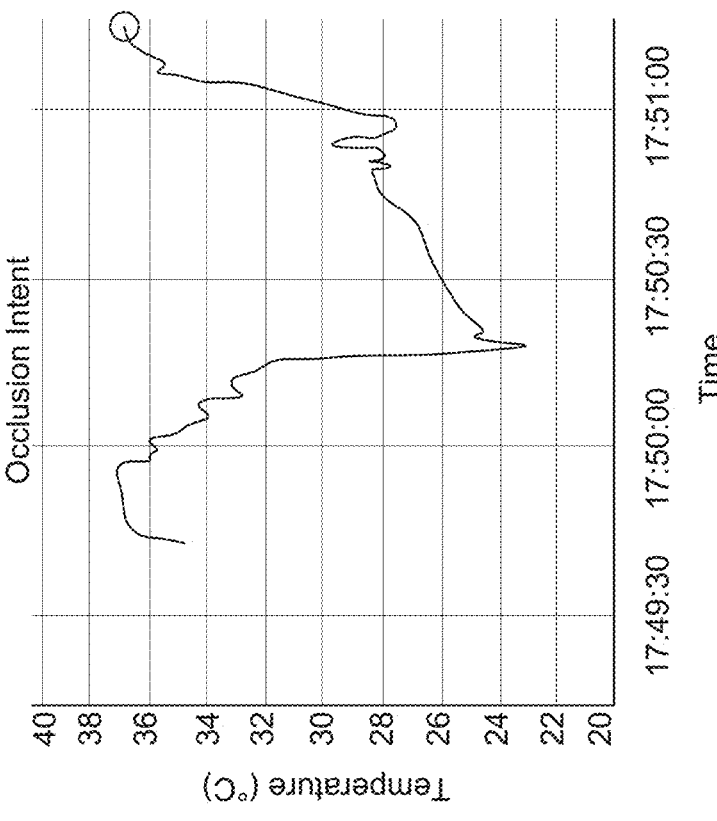
FIG. 8A sets forth in graphical form the results of experiments utilizing the first exemplary embodiment on a model simulating the pulmonary vein.
Figure 8A:
Figure 8A:
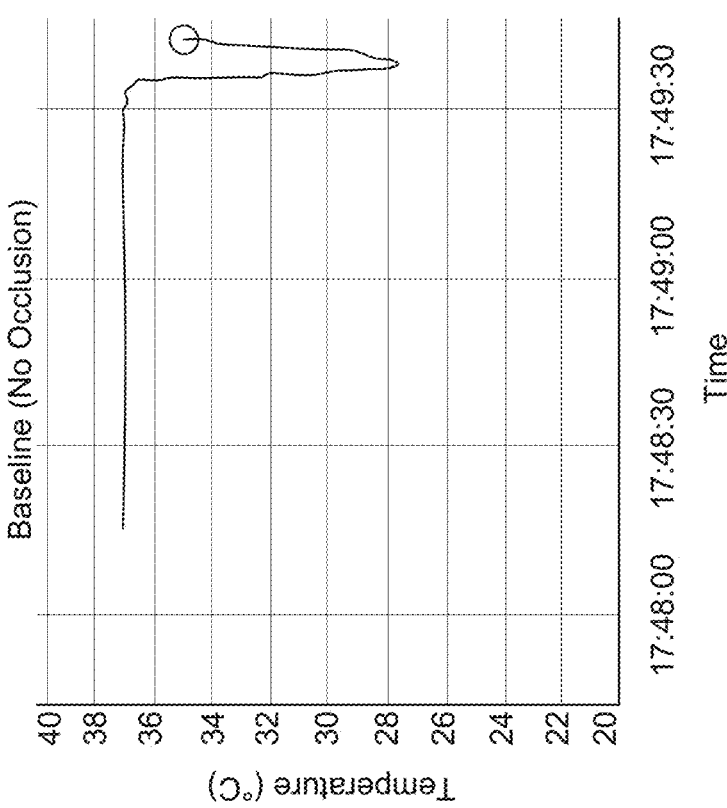

Referring now to FIG. 8A, the display device 62 may be configured to display the at least one characteristic of blood over time. The display device 62 may display the at least one characteristic of blood over time in a meaningful way such as a chart or a graph as shown in FIG. 8A. The display device 62 may be further configured to display a baseline characteristic of blood next to, or on top of, the at least one characteristic of blood over time. In FIG. 8A, two graphs are shown demonstrating results of experiments using a model simulating the pulmonary vein. In each graph, temperature is plotted against time. The model includes a heater to heat water to a baseline temperature, e.g., approximately 37° C., a circulator and two pulmonary veins, the model providing the ability to control the flow rate of water through the model pulmonary veins to simulate the flow of blood through a human pulmonary vein. In one of the models, represented by the left-most graph of FIG. 8A, labeled "Baseline (No Occlusion)", the PV is maintained with no occlusion, while in the other model, represented by the right-most graph of FIG. 8A labeled "Occlusion Intent", representing the PV being fully occluded by the medical tool 24 placed therein. Both graphs show temperature change over time with the introduction of a coolant, e.g., saline. Under both scenarios (no occlusion and full occlusion), the coolant is injected through an inner lumen of the delivery catheter and through the hub of the medical tool 24 into the model pulmonary vein while monitoring temperature change therein using a temperature sensor 23 located on the distal portion of the balloon 80, and/or on the distal portion of the catheter, e.g., the lasso 72*a*. The left-hand graph demonstrates that in the absence of any occlusion, upon injecting the coolant into the model cavity, blood temperature decreases rapidly from a steady-state baseline temperature of approximately 37° C. to approximately 27.5° C., followed by a rapid approach or return to the baseline temperature due to coolant being rapidly flushed from the model PV in the absence of an occlusion. By contrast, in the right-hand graph, where a full occlusion is present, upon injection of the coolant, temperature falls rapidly from the baseline to a significantly lower temperature (approximately 23° C.) and returns to the steady-state baseline temperature over a greater period of time. It should be understood that saline is an exemplary coolant, and that other suitable coolants could be employed in this application in the human pulmonary vein. As alternatives to a coolant, fluid materials having a pH or impedance that differs from blood could be substituted for the coolant and measured to determine the presence or absence of an occlusion. For example, saline, which has a lower impedance than blood could be measured for impedance, rather than temperature. In this manner, the absence or presence of an occlusion may be determined based upon the profile of the curve. The processing device 46 may be further configured to monitor the at least one blood characteristics curve for the effects of heartbeats that can be correlated to the occlusion level.

Figure 8B:
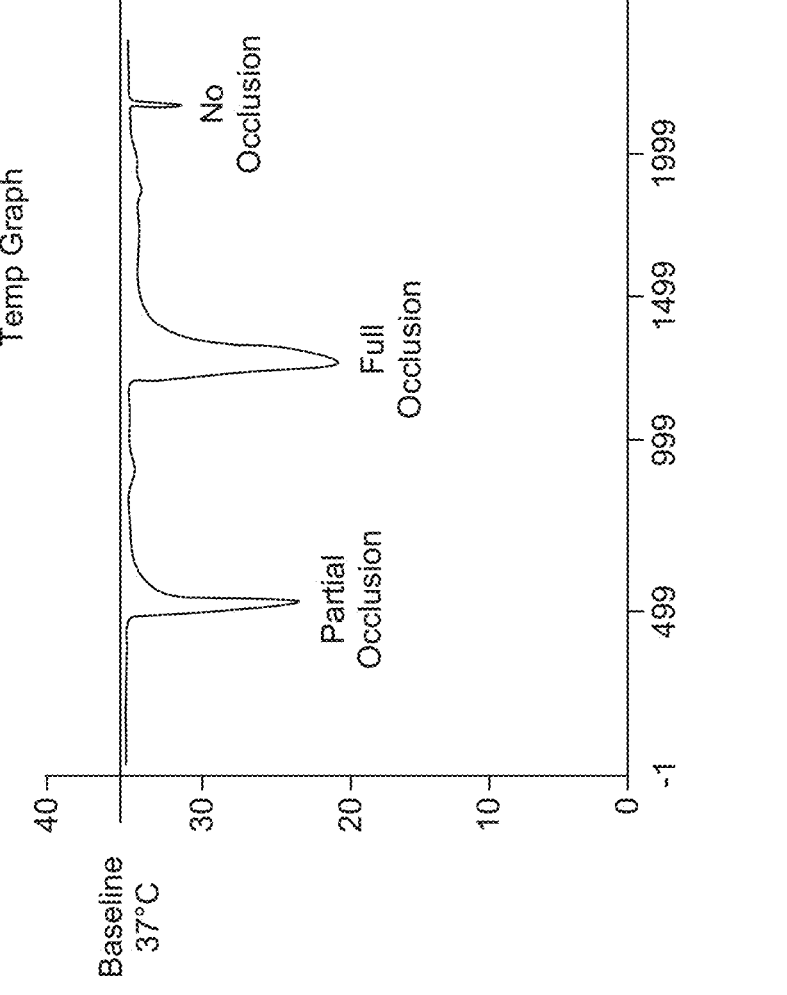
FIG. 8B sets forth in graphical form the results of experiments conducted utilizing the first exemplary embodiment.

Referring now to FIG. 8B there is set forth therein a summary of results of an experiment wherein the medical tool 24 of the first exemplary embodiment is inserted into a superior vena cava to create no occlusion, partial occlusion and full occlusion conditions within the cavity. Sensors 23, e.g., thermocouples, are placed on the distal end of the balloon 80 and/or on the loop of the lasso 72*a*, but could be placed anywhere inside the cavity to detect changes in temperature. The graph summarizes the results of the experiment conducted with no occlusion, partial occlusion, and full occlusion conditions within the cavity. For example, saline is introduced as a coolant into the cavity, first through the irrigation pores 27 (FIG. 6) of the balloon 80 during inflation of the balloon within the cavity, and then by injection of a predetermined amount of saline through the hub of the medical tool 24 over a predetermined period of time, e.g., 10 or 20 ml over a time period of 4 seconds.

As shown in the graph of FIG. 8B, the results of the experiment demonstrate that where no occlusion is present, upon introduction of a coolant as described above into the cavity, there is a slight departure and an almost immediate return to the baseline or steady state temperature of approximately 37° C. Where the medical tool 24 is placed to create a partial occlusion within the cavity, upon introduction of the same coolant in the manner described above, temperature falls rapidly from the baseline to a lower temperature, i.e., approximately 24° C., and takes a greater period of time to recover to the baseline temperature of approximately 37° C., as compared with the no occlusion results. Finally, where the medical tool 24 is placed within the cavity to create a full occlusion, upon introduction of the same coolant in the manner described above, temperature falls rapidly from the baseline to an even lower temperature, i.e., approximately 22°, and includes a greater recovery period to return to the steady state or baseline temperature when compared with the non-occlusion and partial occlusion results. Using such temperature/time profiles or curves, one can determine the existence and sufficiency of occlusion.

Figure 8C:
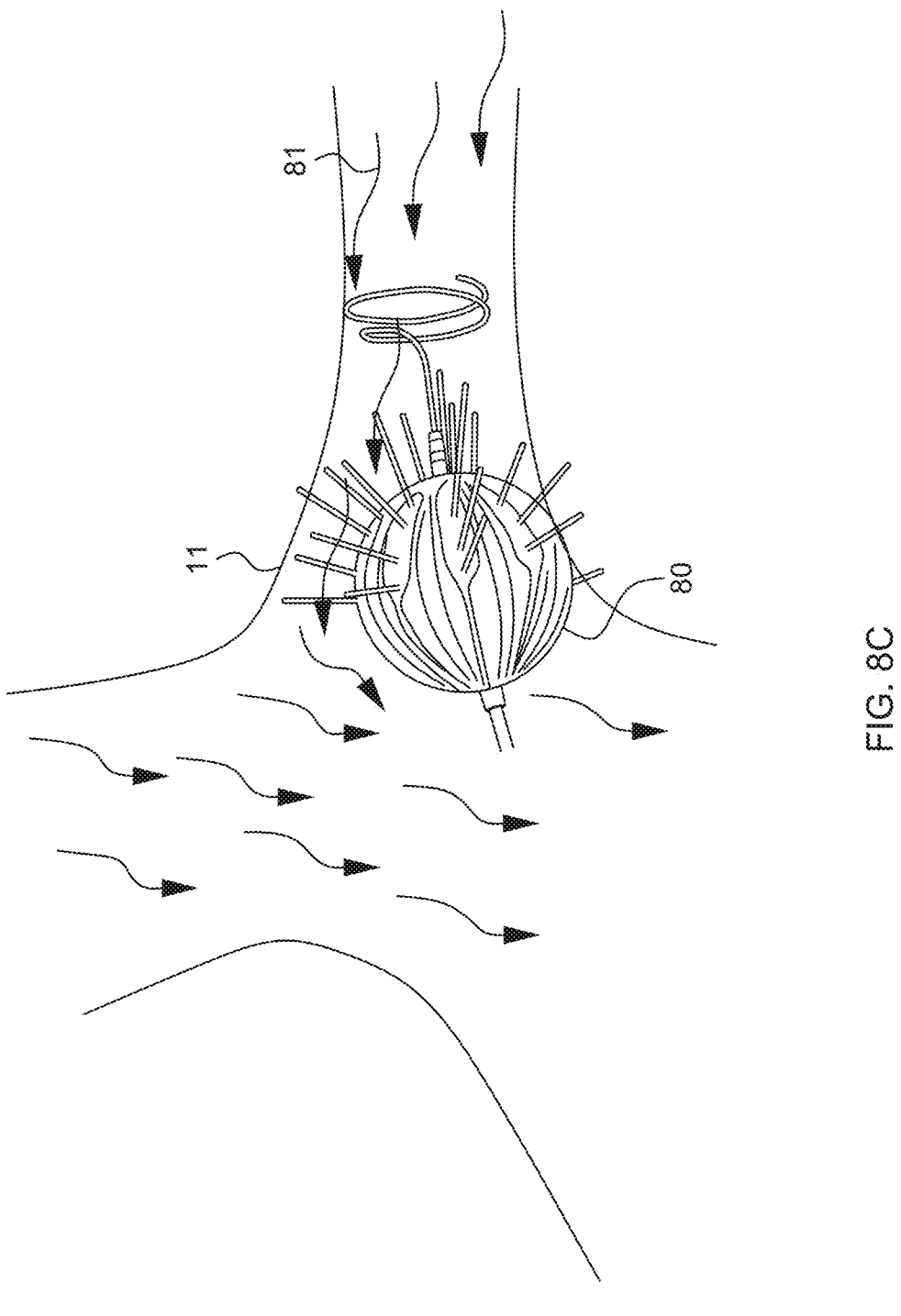
FIG. 8C is a side view of an expandable balloon of the first exemplary embodiment deployed in proximity to the pulmonary vein and its ostium.
Figure 8D:
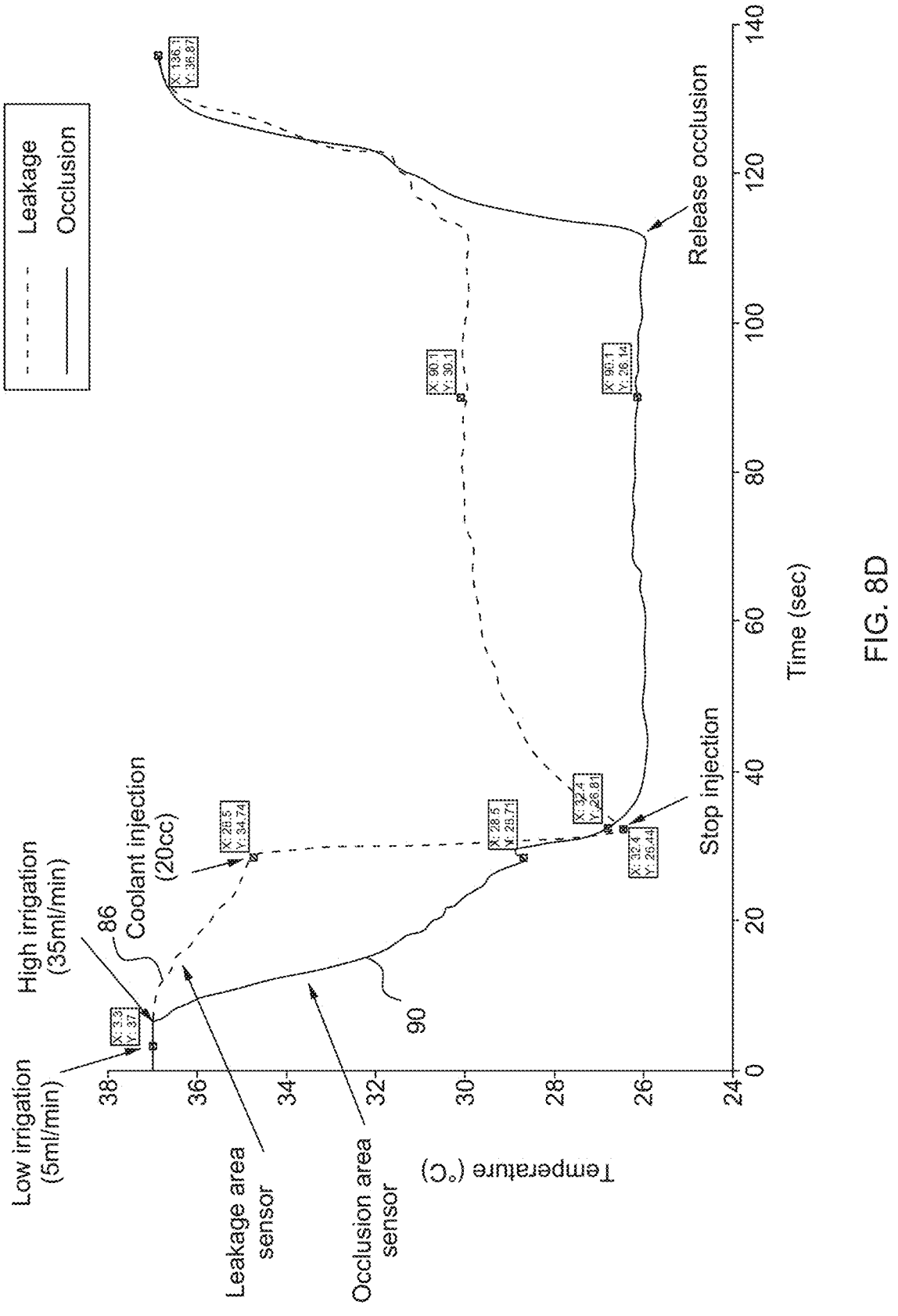
FIG. 8D sets forth the results in graphical form of an experiment.

Referring now to FIGS. 8C and 8D, an experiment was conducted wherein the balloon 80 was inserted within the opening 11 of the superior vena cava in a position to create a partial occlusion to include an occluded area where the balloon 80 touches the interior wall of the cavity and a leakage area indicated by arrows 81 (FIG. 8C) where blood may flow past the balloon 80. Temperature sensors 23 are located at the center of each electrode 33 positioned over the circumference of the balloon 80 (FIGS. 3 and 5). Thus, most of the sensors 23 are positioned touching the cavity wall in the occluded area, and one or two sensors 23 are positioned away from the cavity wall in the leakage area. By positioning of the sensors 23 in this manner, one can detect temperature changes in the leakage area and in the occluded area and compare them. As shown in FIG. 8D, the line 86 indicates temperature sensed in the blood leakage area. By contrast, the line 90 indicates temperature sensed in the occluded area. Upon the introduction of the coolant, e.g., saline, into the cavity through the irrigation pores 27 during inflation of the balloon 80 (at the rate of 35 ml/min, a more rapid temperature drop is detected in the occlusion area 90 than in the leakage area 86. Further, upon the introduction of a coolant by injection (indicated at "coolant injection 20 cc"), the rate of temperature drop in the leakage area 86 accelerates. As illustrated in FIG. 8D, upon the completion of coolant injection, temperature recovery in the leakage area 86 differs from the occlusion area 90. Upon removal of the occlusion or "release occlusion" from within the cavity, temperature in both areas eventually returns to the baseline temperature as indicated at lines 86 and 90. Alternatively or additionally, the coolant could be introduced into the cavity solely through the irrigation pores 27 during inflation of the balloon, without any injection through the hub of the medical tool 24.

Alternatively or additionally, the processing device 46 may be further configured to determine whether an occlusion is present by comparing at least one blood characteristic data over time to a baseline of the at least one characteristic of blood. The processing device 46 may be configured to execute an algorithm based on the at least one blood characteristic to determine the presence or absence of an occlusion, or to calculate a number indicating the extent of occlusion. The at least one blood characteristic can be any physical or chemical characteristics of blood measured prior to the procedure to establish a baseline such that any change over time over a predetermined threshold subsequent to the expansion of the balloon can be used to infer that occlusion is ongoing or being achieved.

Figure 9:
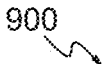
FIG. 9 is a flowchart illustrating a method of occlusion detection of the first exemplary embodiment of the invention.
Figure 9:
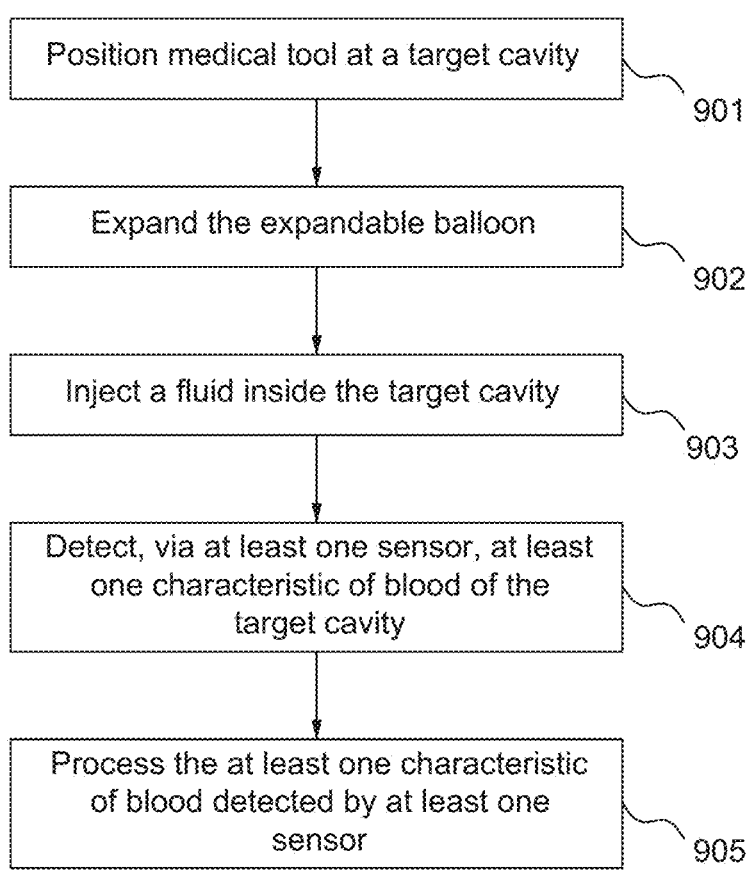

With reference to FIG. 9, a method for occlusion detection is disclosed. The method may be performed with the system for occlusion detection disclosed above. At step 901, the medical tool 24 is positioned at a target location within a portion of an organ of a patient such that occlusion will be established. The medical tool 24 is positioned via delivery catheter 72. The delivery catheter 72 may be a focal linear catheter 99 or a lasso catheter 72a. The medical tool 24 is coupled to the distal portion of the distal end of the delivery catheter 72, as discussed above. The medical tool 24 may comprise an expandable balloon 80 and at least one sensor 23, as described above. At step 902, the expandable balloon 80 is expanded when the balloon 80 is positioned at the target location. The expandable balloon 80 has a distal end and a proximal end defining a longitudinal axis 78, as described above. At step 903, a fluid is injected into a target cavity through the inner lumen of the delivery catheter 72. Additionally or alternatively, the expandable balloon 80 may comprise irrigation pores 27, as described above, and the fluid may be injected into the target cavity through the delivery catheter 72 and through one or more of the irrigation pores 27 of the expandable balloon 80. The target cavity may be one of a pulmonary vein or a left atrium of the heart. The fluid may be a coolant, such as saline or glucose at a low temperature. At step 904, the at least one characteristic of blood is detected via at least one sensor 23. At step 905, the processing device 46 processes the at least one characteristic of blood. The presence or absence of an occlusion is determined by the at least one characteristic of blood. Injecting a fluid, such as saline, may change the at least one characteristic of blood inside the target cavity. Therefore, changes in the at least one characteristic of blood may indicate the presence or absence of an occlusion The at least one sensor 23 may be a temperature sensor and the at least one characteristic of blood may be temperature. Alternatively or additionally, the at least one sensor 23 may be a first electrode and a second electrode and the at least one characteristic may be bipolar electrical impedance. Alternatively or additionally, the at least one sensor 23 may be a first electrode and a second electrode, the second electrode being a reference electrode, and the at least one blood measurement may be unipolar electrical impedance. Alternatively or additionally, the at least one sensor 23 may be a pH sensor, and the at least one characteristic of blood may be pH.

Figure 10:
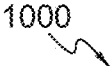
FIG. 10 is a flowchart illustrating a method of determining a baseline measurement of a patient for occlusion detection in accordance with the first exemplary embodiment of the invention.
Figure 10:
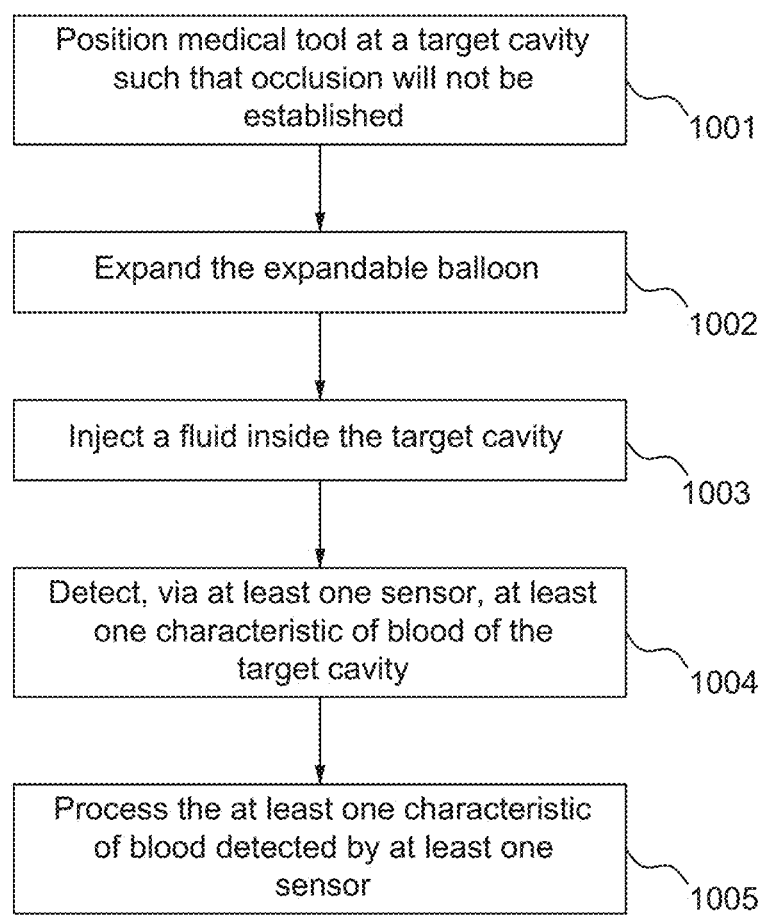

With reference to FIG. 10, a baseline pressure of the at least one characteristic of blood may be determined. At step 1002, the medical tool 24 may be positioned at a target location within a portion of an organ of a patient such that occlusion will not be established. At step 1002, the expandable balloon 80 may be expanded when the balloon 80 is positioned at the target location. At step 1003, a fluid is injected through an inner lumen of the delivery catheter. Additionally or alternatively, the expandable balloon 80 may comprise irrigation pores 27, as described above, and the fluid may be injected into the target cavity through the delivery catheter 72 and through one or more of the irrigation pores 27 of the expandable balloon 80. At step 1004, at least one characteristic of blood in the target cavity is detected via at least one sensor 23. At step 1005, the processing device 46 processes the at least one characteristic of blood data and establishing the data as a baseline measurement.

The method may further comprise recording, via the processing device 46, the at least one characteristic of blood over time. The method may further comprise storing, in the memory 50, measurements of the at least one blood characteristic over time. The presence or absence of an occlusion may be determined by comparing the baseline of the at least one baseline blood measurement and the at least one blood measurement detected by the at least one sensor 23 over time. The method may further comprise determining, via the processing device 46, the presence or absence of an occlusion by comparing the baseline of the at least one characteristic of blood and the detected at least one characteristic of blood over time. Additionally or alternatively, the processing device 46 may be further configured to determine whether an occlusion is present in the target cavity based on how quickly the at least one characteristic of blood returns to its original value after the fluid is injected. The method may further comprise executing an algorithm, via the processing device 46, to detect the presence or absence of an occlusion, or to calculate a number indicating the extent of occlusion. The method may further comprise monitoring, via the processing device 46, the curve of the at least one characteristic of blood over time for the effects of heartbeats that may be correlated to the occlusion level.

The methods described and illustrated in relation to FIGS. 9 and 10 are also algorithms that can be utilized by a skilled software engineer to generate the requisite step-by-step computer codes for implementation of the overall method in a computer system (e.g., a general-purpose computer or a special purpose computer such as the Carto system) so that embodiments described herein can be used to detect occlusion.

Under a second exemplary embodiment, a medical tool system for occlusion detecting in a left atrial appendage ("LAA") of a heart is provided.

A method for occlusion detection in accordance with the present disclosure comprises positioning a medical tool coupled to a distal end of a delivery catheter at a target location within a portion of an organ of a patient, the medical tool comprising an occluder portion, an anchor portion, a tissue growth member and a hub; deploying the occluder portion of the medical tool and, upon the occluder portion being in an expanded, deployed position, actuating the anchor portion from a retracted position to an anchor deployed position; injecting a fluid through the delivery catheter and through the hub of the medical tool, into a target cavity, wherein the tissue growth member prevents the fluid from exiting the cavity; detecting, via at least one sensor, at least one characteristic of blood in the target cavity; and processing, via a processor, the at least one characteristic of blood data, wherein the presence or absence of an occlusion is determined by the at least one characteristic of blood.

Under the second exemplary embodiment, the fluid may comprise a coolant, such as, for example, saline. Additionally or alternatively, the fluid may comprise glucose at a low temperature.

The at least one sensor may comprise a temperature sensor and the at least one characteristic comprises temperature. Alternatively or additionally, the at least one sensor comprises a first electrode and a second electrode and the at least one characteristic may comprise bipolar electrical impedance. Alternatively or additionally, the least one sensor may comprise a first electrode and a second electrode and the second electrode may a reference electrode, and the at least one characteristic may comprise unipolar electrical impedance. Alternatively or additionally, the at least one sensor may comprise a pH sensor and the at least one characteristic may comprise pH.

Alternatively or additionally, under the second exemplary embodiment, the method may further comprise determining a baseline of the at least one characteristic of blood by: positioning the medical tool at a target location within a portion of an organ of a patient such that occlusion will not be established; deploying the occluder portion of the medical tool and, upon the occluder portion being in an expanded, deployed position, actuating the anchor portion from a retracted position to an anchor deployed position having tines without establishing complete occlusion; injecting a fluid through the delivery catheter and through the hub of the medical tool into a target cavity; detecting, via the at least one sensor, at least one characteristic of blood in the target cavity, and processing, via a processor, the at least one characteristic of blood data and establishing the data as a baseline measurement.

The method of the second exemplary embodiment may further comprise recording, via the processor, measurements of the at least one characteristic of blood over time. The method may further comprise storing, in a memory, measurements of the at least one characteristic of blood over time.

Under the second exemplary embodiment, the presence or absence of an occlusion may be determined by comparing the baseline measurement to the detected at least one characteristic of blood over time. The method may further comprise determining, via a processor, the presence or absence of an occlusion by comparing the baseline measurement to the detected at least one characteristic of blood over time.

Under the second exemplary embodiment, the target cavity may be the LAA and the tines of the anchor portion may be configured to engage tissue with the LAA. The processor may be further configured to determine whether an occlusion is present in the LAA based on how quickly the at least one characteristic of blood returns to its original value after the fluid is injected.

Under the second exemplary embodiment, the tines of the anchor portion may be configured to engage tissue with the LAA and the left atrium. The method may be performed twice, once on the LAA and once on the left atrium. The processor may be further configured to record the at least one blood characteristic of the LAA and the at least one characteristic of blood of the left atrium over time, and then compare the at least one characteristic of blood of the LAA and the at least one characteristic of blood of the left atrium. Alternatively or additionally, the processor may be further configured to determine whether an occlusion is present in the LAA using the comparison of the at least one characteristic of blood of the LAA and the at least one characteristic of blood of the left atrium, and determine whether an occlusion is present in the left atrium using the comparison of the at least one characteristic of blood of the LAA and the at least one characteristic of blood of the left atrium.

A system for occlusion detection in accordance with the present disclosure comprises a sheath, a delivery system, a medical tool, at least one sensor and a processor. The sheath has a length and a sheath lumen extending through the length of the sheath. The delivery system comprises a delivery catheter extending between a proximal end and a distal end, and a handle coupled to the proximal end of the delivery catheter. The medical tool is coupled to a distal end of the delivery catheter at a target location within a portion of an organ of a patient. The medical tool comprises a hub including a bore defining an axis; an occluder portion coupled to the hub, the occluder portion configured to be moved to an occluder non-deployed position with the occluder portion within a distal portion of the sheath, and the occluder portion configured to be moved to an occluder deployed position upon the sheath being moved proximally relative to the occluder portion; and an anchor portion extending between a first end and a second end, the anchor portion having tines configured to engage tissue, the first end being coupled to the handle, the second end being pivotable coupled to a distal end portion of the occluder portion, wherein, upon the occluder portion maintaining the occluder deployed position, the anchor portion is pivotable relative to the occluder portion between an anchor non-deployed position and an anchor deployed position. The at least one sensor is configured to detect at least one physical characteristic of blood. The at least one processor is configured to process the blood characteristic data acquired from the at least one sensor.

In the second exemplary embodiment, the at least one sensor may comprise a temperature sensor. The at least one sensor may comprise at least two electrodes. One electrode may comprise a reference electrode. Alternatively or additionally, the at least one sensor may comprise a pH sensor.

The at least one sensor may be located on a distal portion of the sheath. Alternatively or additionally, the at least one sensor may be located on the distal end of the delivery catheter or may be located on a proximal end of the delivery catheter.

In the second exemplary embodiment, the tines of the anchor portion may be configured to engage tissue within a LAA. Alternatively or additionally, the tines of the anchor portion may be configured to engaged tissue within a left atrium.

In the second exemplary embodiment, the processor may be further configured to compare the blood characteristic data acquired from the at least one sensor to a baseline blood characteristic. Alternatively or additionally, the processor may be further configured to record measurements of the at least one characteristic of blood over time. The system may further comprise a memory configured to store the measurements of the at least one characteristic of blood. The system may further comprise a display configured to display the at least one characteristic of blood over time. The display may be further configured to display a baseline characteristic of blood next to, or on top of, the at least one characteristic of blood over time. The processor may be further configured to determine whether an occlusion is present in the LAA based on how quickly the at least one characteristic of blood returns to its original value after the fluid is detected.

Under the second exemplary embodiment, the tines of the anchor portion may be configured to engage tissue with the LAA and the left atrium. The processor may be further configured to record the at least one blood characteristic of the LAA and the at least one characteristic of blood of the left atrium, and then compare the at least one characteristic of blood of the LAA and the at least one characteristic of blood of the left atrium. Alternatively or additionally, the processor may be further configured to: determine whether an occlusion is present in the LAA using the comparison of the at least one characteristic of blood of the LAA and the at least one characteristic of blood of the left atrium; and determine whether an occlusion is present in the left atrium using the at least one characteristic of blood of the LAA and the at least one characteristic of blood of the left atrium.

Figures 11, 11A, 11B:
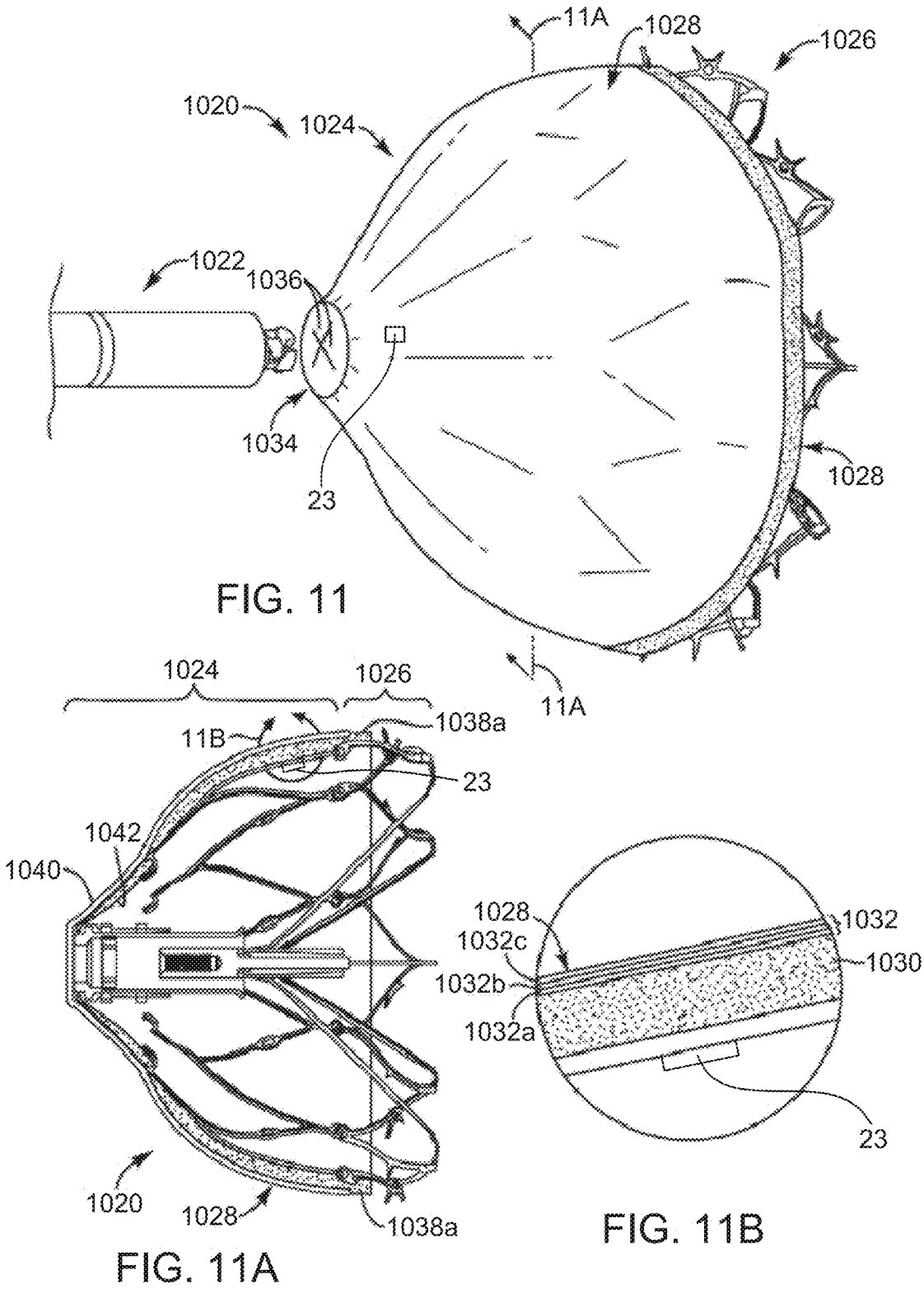
FIG. 11 is a perspective view of a medical tool and a distal portion of a delivery system, in accordance with the second exemplary embodiment of the invention.
FIG. 11A is a partial cross-sectional view of the medical tool, taken along section line 11A of FIG. 11.
FIG. 11B is an enlarged section view of an occluder portion, taken from detail 11B of FIG. 11A, according to the second exemplary embodiment of the present invention.

Referring first to FIGS. 11 and 11A, a medical tool 1020 and a distal end portion of a delivery system 1022 is provided. The medical tool 1020 and delivery system 1022 may be employed in interventional procedures for percutaneously closing and modifying an opening or cavity such as, for example, a LAA within a heart (not shown). The medical tool 1020 may include frame components of an occluder portion 1024 and an anchor portion 1026, the occluder portion 1024 also including a tissue growth member 1028 attached thereto. Further, the anchor portion 1026 may be hingably coupled to the occluder portion 1024 such that the anchor portion 1026 may be actuated, upon deployment of the occluder portion 1024, between a deployed position and a non-deployed position (not shown) via an actuation mechanism at a handle (not shown) of the delivery system 1022. With this arrangement, the medical tool 1020 and delivery system 1022 may provide functionality of separating the steps of deploying the occluder portion 1024 and the anchor portion 1026, thereby, providing additional and enhanced functionality to the physician to properly position and implant the medical tool 1020 in the LAA.

As set forth, the occluder portion 1024 may include an occluder material or a tissue growth member 1028 attached thereto. The tissue growth member 1028 may be a porous material, or other cell attaching material or substrate, configured to promote endothelization and tissue growth thereover. The tissue growth member 1028 may extend over a proximal side of the medical tool 1020 and, particularly, over the occluder portion 1024 and may extend over a portion of the anchor portion 1026 and hinges coupling the anchor portion 1026 to the occluder portion 1024. As such, due to the shape of the frame components of the occluder portion 1024, the tissue growth member 1028 may include a proximal face that is generally convex to form an outer surface 1040. The tissue growth member 1028 may also include an inner surface 1042 on its distal side that is generally concave shaped. Under the second exemplary embodiment, the tissue growth member 1028 may extend primarily over an outside surface of frame components of the occluder portion 1024 with a portion of the tissue growth member 1028 extending on both the outside surface and the inside surface of the frame components of the occluder portion 1024. Alternatively or additionally, the tissue growth member 1028 may extend primarily over both the outside surface and the inside surface of the frame components of the occluder portion 1024 of the medical tool 1020. The tissue growth member 1028 may extend solely over the outside surface of the frame components of the occluder portion 1024.

With respect to FIGS. 11A and 11B, the tissue growth member 1028 may include one or more types of materials and/or layers. The tissue growth member 1028 may include a first material layer 1030 and a second material layer 1032. The first material layer 1030 may primarily be an underside layer or base layer of the tissue growth member 1028. The first material layer 1030 may include porous and conformable structural characteristics. For example, the first material layer 1030 may include a foam type material, such as, a polyurethane foam or any other suitable polymeric material, such as a polymer fabric, woven or knitted. The second material layer 1032 may include one or more layers of, for example, an expanded polytetrafluoroethylene (ePTFE) material. The second material layer 1032 may be attached to an outer surface of the first material layer 1030 with, for example, an adhesive. The second material layer 1032 may include a first layer 1032A, a second layer 1032B, and a third layer 1032C such that the first layer 1032A may be directly attached to the first material layer 1030 and the third layer 1032C may be an outer-most layer covering the proximal side of the medial device 1020 with the second layer 1032B extending therebetween. The various layers of the second material layer 1032 may be bonded together by adhesives and/or by a thermal bonding heat process or other appropriate processes known in the art. In one particular example, the outer-most layers, such as the second and third layers 1032B, 1032C, may be formed of an ePTFE material having an internodal distance (sometimes referred to as pore size) of approximately 70 μm to approximately 90 μm. The first layer 1032A of the second material layer 1032, adjacent the first material layer 1030, may be formed of an ePTFE material having a reduced internodal distance relative to the second and third layers 1032B, 1032C. For example, the internodal distance of the first layer 1032A may be approximately 10 μm. This first layer 1032A may be bonded or adhered to the first material layer 1030 using an adhesive material. Any other suitable sized layers of ePTFE may be employed, such as ePTFE having an internodal distance up to about 250 μm. Further, there may be one or more additional layers, similarly sized to the first layer 1032A, extending over a hub end 1034 with flaps 1036 (outlined with an "X" configuration) where the delivery system 1022 interconnects with the medical tool 1020 (see FIG. 1).

The second material layer 1032 made of ePTFE effectively prevents the passage of blood, due to the small internodal distance and pore size of the first layer 1032A, while the larger internodal distance of other layers (e.g., 1032B and 1032C) enable tissue in-growth and endothelization to occur. Additionally, the first material layer 1030, being formed of a polyurethane foam, enables aggressive growth of tissue from the LAA wall into the tissue growth member 1028 at the inside or concave side of the medical tool 1020. Further, the first material layer 1030 provides an exposed shelf 1038 on the outer surface 1040 around the periphery and distal end portion of the tissue growth member 1028, which promotes aggressive fibroblast and tissue growth to further initiate endothelization over the outer surface 1040 of the second material layer 1032. It is noted that the use of appropriate adhesive materials between the first material layer 1030 and the next adjacent layer 1032A may also serve to fill in the pores of the next adjacent layer 1032A and further inhibit possible flow of blood through the tissue growth member 1028. Additional layers of ePTFE may also be included to the second material layer 1032 of the tissue growth member 1028.

Figures 12, 13:
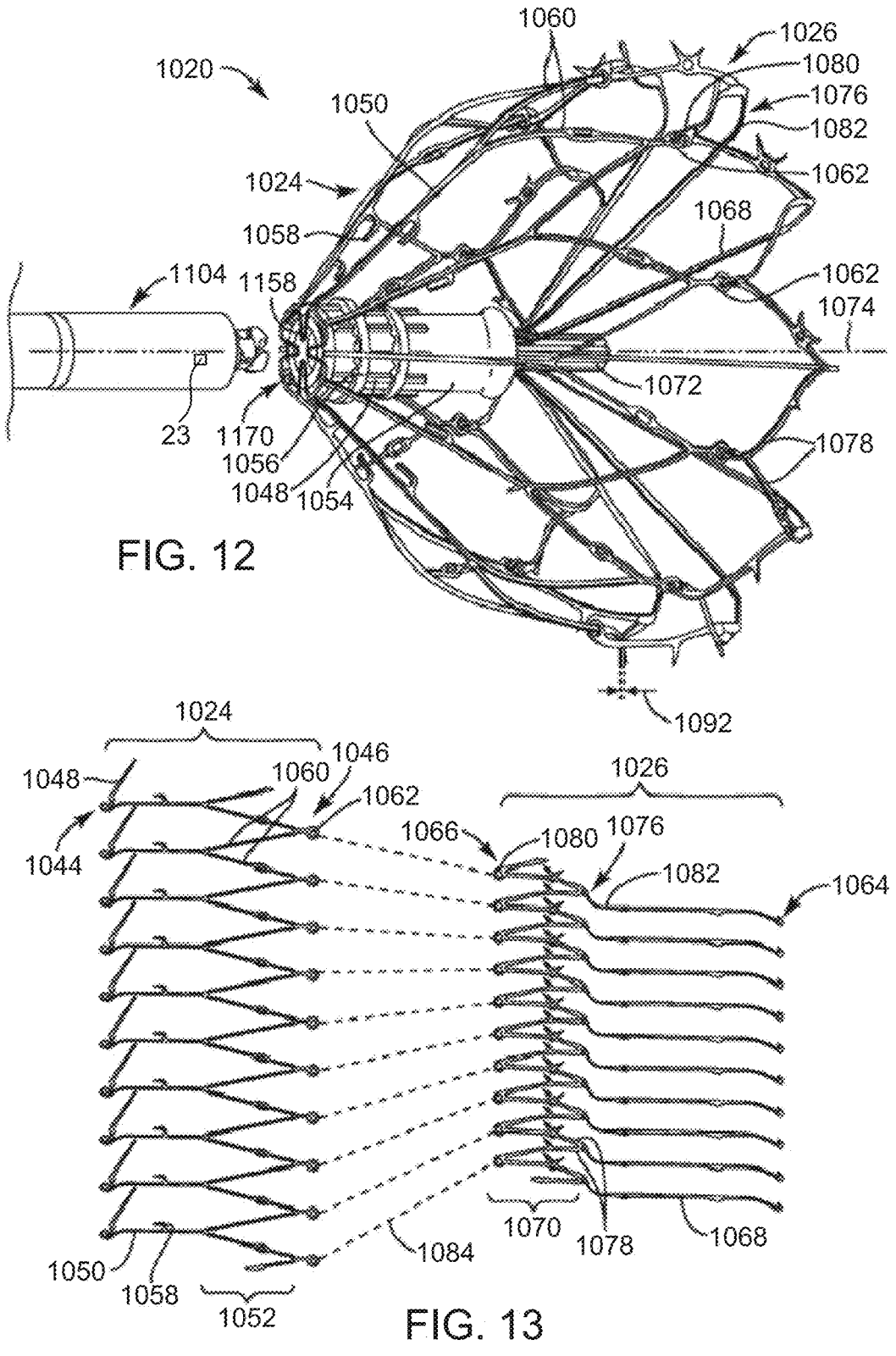
FIG. 12 is a perspective view of the medical tool of FIG. 11, depicting the frame without its tissue growth member, according to the second exemplary embodiment of the present invention.
FIG. 13 is a top view of frame components of the occluder portion and the anchor portion of the medical tool of FIG. 12, depicting frame components laser cut from a flat sheet prior to being assembled.

With reference to FIGS. 12 and 13, description of the medical tool 1020 and its frame components will now be provided. FIG. 12 depicts the frame components in an assembled and fully deployed state and FIG. 13 depicts the frame components as cut from a flat sheet. As previously set forth, the medical tool 1020 includes an occluder portion 1024 and an anchor portion 1026. The occluder portion 1024 may include multiple occluder frame segments that may be interconnected to form the occluder portion 1024. The occluder portion 1024 may extend between a first end 1044 and a second end 1046 with face struts 1050 and an occluder zig-zag portion 1052 therebetween. Further, the occluder portion 1024 includes base extensions 1048 extending from the first end 1044. The base extensions 1048 may be coupled to a hub 1054 via rings 1056 with notches defined at an inner diameter in the rings 1056. Each base extension 1048 may extend from a proximal most portion of the occluder portion 1024 or first end 1044, the first end 1044 being one end of each base extension 1048 and face strut 1050. Each base extension 1048 may be sized and configured to be positioned around the hub 1054 and held by one or more rings 1056. Each base extension 1048, at the first end 1044, may extend to one face strut 1050 of the occluder portion 1054, the face strut 1050 extending radially and distally from the first end 1044. Each face strut 1050 may include an extension 1058 on a back side thereof, the extension 1058 having a hook configuration sized and configured to hold a portion of the tissue growth member (not shown). Further, each face strut 1050 extends to a v-extension 1060 of the occluder zig-zag portion 1052 such that distal ends of each v-extension 1060 may be coupled to distal ends of adjacent v-extensions 1060 (side-by-side) to define the occluder zig-zag portion 1052. The occluder zig-zag portion 1052 may enlarge radially and distally from the face struts 1050 to a distal end or the second end 1046 of the occluder portion 1024. At the second end 1046, the occluder portion 1024 may include an occluder eyelet 1062 sized configured to hingably couple to the anchor portion 1026.

The anchor portion 1026 may include multiple anchor frame segments that may be interconnected to form the anchor portion 1026. The anchor portion 1026 may extend between a first end 1064 and a second end 1066 with anchor actuator arms 1068 and an anchor zig-zag portion 1070 therebetween. The anchor actuator arms 1068 may extend between the first end 1064 and the anchor zig-zag portion 1070. Each anchor actuator arm 1068 may be configured to couple to a collar arrangement or splined sleeve 1072 at the first end 1064 of the anchor portion 1026 such that the anchor actuator arms 1068 are coupled as a unit or together via the splined sleeve 1072. The splined sleeve 1072 may be configured to actuate along an axis 1074 of the medical tool 1020 to move the anchor portion 1026 between the anchor deployed position and anchor non-deployed position (not shown), discussed in more detail hereafter.

Figures 13A, 13B:
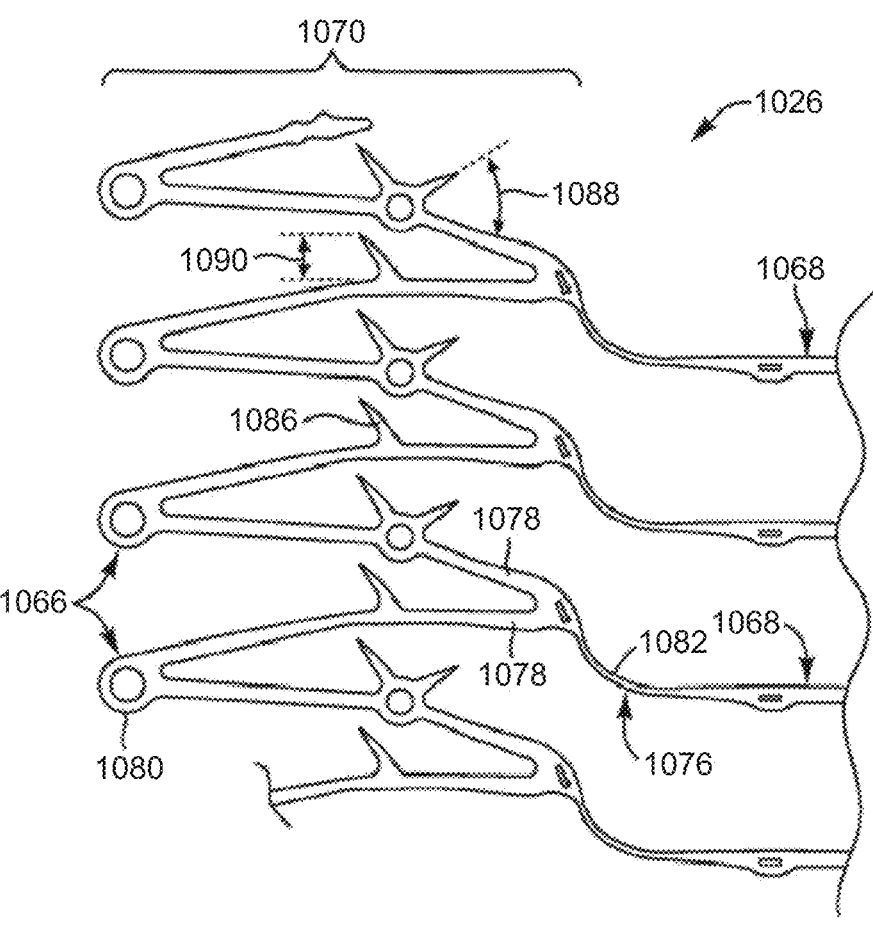
FIG. 13A is a partial enlarged view of the anchor portion depicted in FIG. 13.
FIG. 13B is an enlarged view of a hinged coupling between the occluder portion and the anchor portion of the medical tool.

With reference now to FIGS. 12, 13, and 13A, the anchor actuator arms 1068 may also include a flexure portion 1076. The flexure portion 1076 defines a taper 1082 and radius extending along the radial length of the flexure portion 1076 toward the anchor zig-zag portion 1070 and then widens again at the anchor zig-zag portion 1070. Such taper 1082 along the radial length in the flexure portion 1076 facilitates repetitious movement of the anchor portion 1026 between the deployed position and the non-deployed position while also maintaining structural integrity of the anchor portion 1026, and minimizing the stress and strain in the flexure portion 1076 while facilitating a tight radius or loop. In one embodiment, the anchor actuator arms 1068 may each include a coil (not shown) that may be wound around a portion of the actuator arm and over the flexure portion 1076 with the ends of the coil secured to the anchor actuator arm 1068. Such coil may substantially capture the anchor actuator arm 1068 from extending in undesirable locations in the LAA should there be a facture or break in the anchor actuator arm 1068.

Each flexure portion 1076 of the anchor actuator arms 1068 may extend to anchor v-extensions 1078 such that the proximal ends of each anchor v-extension 1078 may be coupled to proximal ends of adjacent anchor v-extensions 1078 (similar to the occluder zig-zag portion 1052) to form the anchor zig-zag portion 1070. At the interconnection of the proximal ends of the anchor v-extensions 1078 or the second end 1066 of the anchor portion 1026, such proximal ends define an anchor eyelet 1080. The anchor eyelet 1080 may be sized and configured to hingably couple to a corresponding occluder eyelet 1062 of the occluder portion 1024, as shown by dotted lines 1084 (see FIG. 13).

With respect to FIG. 13A, the anchor struts or anchor v-extensions 1078 of the anchor zig-zag portion 1070 may include one or more hooks 1086 or barbs that may extend at an acute angle 1088 from the anchor portion 1026 or anchor v-extensions and remote from the occluder portion 1024. Such acute angle 1088 may range between about forty-five degrees and about sixty degrees. Further, the hooks 1086 may extend from the anchor v-extensions 1078 with a predetermined height 1090 so as to provide effective engagement with a tissue wall within the LAA, but not to the extent of piercing all the way through the tissue wall to cause effusions in the LAA. The hooks also include a thickness 1092 (see FIG. 12). Such thickness 1092 may be similar to the thickness of sheet material from which the frame components (i.e., occluder portion 1024 and anchor portion 1026) of the medical tool 1020 are cut.

With respect to FIG. 13, the occluder portion 1024 and the anchor portion 1026 are depicted in a pre-formed state subsequent to being laser cut from a flat sheet or sheet material of, for example, super elastic material, such as Nitinol. As such, the occluder portion 1024 and the anchor portion 1026, in the pre-formed state, may be substantially planar and flat, after which, the frame components of the occluder portion 1024 and/or the anchor portion 1026 may then be heat-set to a desired shape and configuration, as known to one of ordinary skill in the art, similar to the fully deployed configuration (see FIG. 12). Further, as known to one of ordinary skill in the art, other processes may be employed, such as chemical etching and electro-polishing of the frame components. The occluder portion 1024 may include ten face struts 1050 and ten base extensions 1048 with ten occluder eyelets 1062 extending from the occluder zig-zag portion 1052. Similarly, the anchor portion 1026 may include ten anchor actuator arms 1068 with ten anchor eyelets 1080 extending from the anchor zig-zag portion 1070. It should be noted that the occluder portion 1024 and anchor portion 1026 may include more or less frame components, such as the respective face struts 1050 and anchor actuator arms 1068, as known to one of ordinary skill in the art. As shown by dotted line 1084, occluder eyelets 1062 may be configured to couple to corresponding anchor eyelets 1080 with a hinge-like coupling arrangement. Such may be employed by directly interlocking the occluder eyelets 1062 with the anchor eyelets 1080, as depicted in FIG. 12.

The frame components of the occluder portion 1024 and the anchor portion 1026 may be laser cut from tubular material, rather than a flat sheet. The frame components may be laser cut, and then heat set to the desired configuration, similar to that shown in FIG. 12. Various frame components of the occluder portion 1024 and the anchor portion 1026 may need to be modified as readily understood by one of ordinary skill in the art.

With reference to FIG. 13B, the occluder portion 1024 and the anchor portion 1026 may be hingably coupled together by aligning the occluder eyelets 1062 with the anchor eyelets 1080 and positioning an individual interlocking piece 1094 (shown in outline) within and through each of the respective aligned eyelets 1062, 1080. Such an interlocking piece 1094 may be a polymeric filament or the like. Ends 1096 of the interlocking piece 1094 may be heated to form a bulbous shape (not shown) at the ends 1096 that, upon cooling, harden and maintain the bulbous shape so as to prevent the respective aligned eyelets from de-coupling. In this manner, the occluder and anchor eyelets 1062, 1080 may be interlocked via the interlocking piece 1094 to provide a hinged coupling arrangement for the anchor portion 1026 to pivot relative to the occluder portion 1024 and, more particularly, for the anchor portion 1026 to pivot about the occluder eyelets 1062. The interlocking piece 1094 may be a metallic rivet press fitted through aligned eyelets to provide a hinged coupling arrangement.

Figure 14:
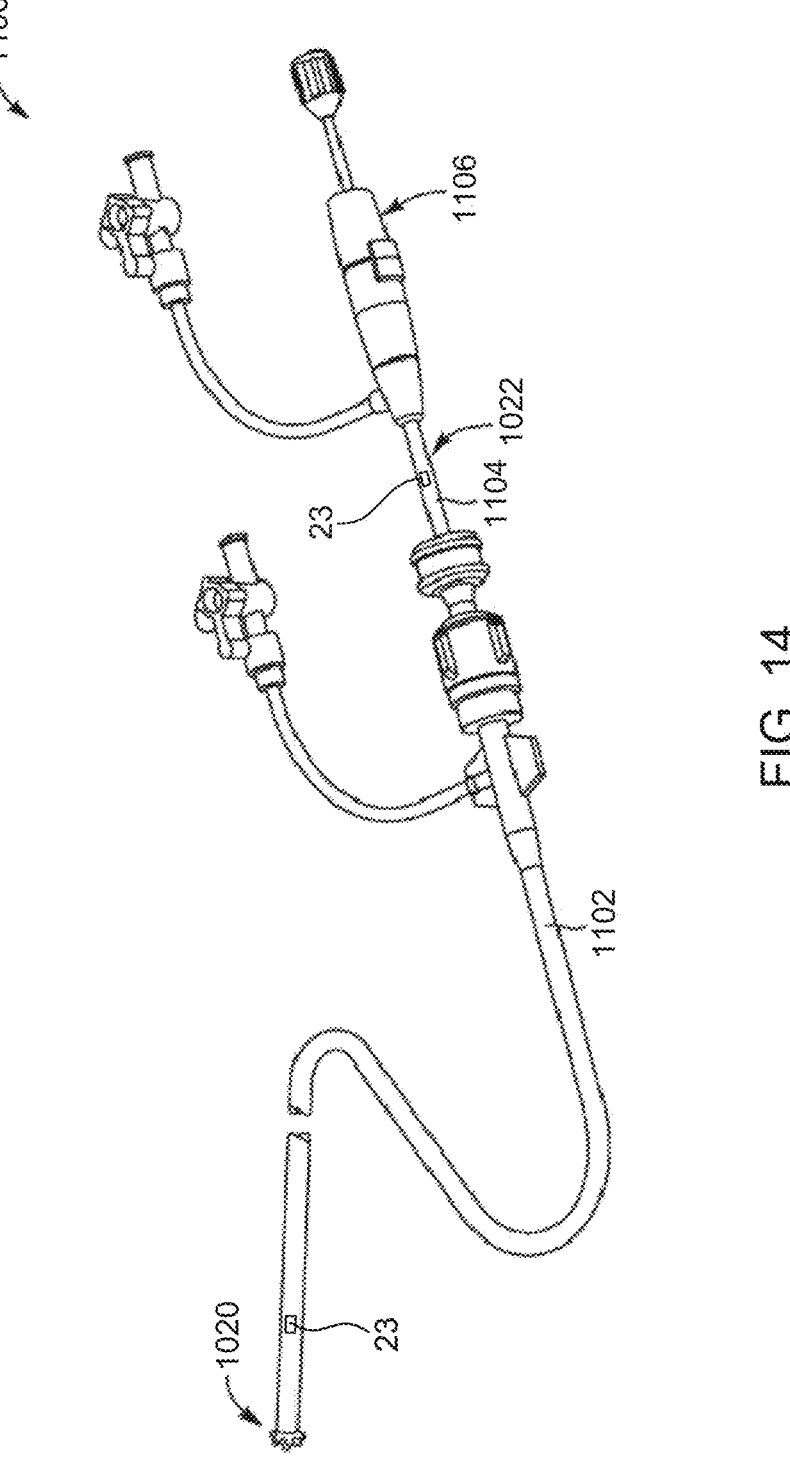
FIG. 14 is a perspective views of a medical tool delivery system, according to the second exemplary embodiment of the present invention.

Now with reference to FIG. 14, a medical tool delivery system 1100 for delivering the medical tool 1020 to, for example, the LAA is provided. The medical tool delivery system 1100 may include the before-mentioned delivery system 1022, the medical tool 1020, and a sheath 1102. The delivery system 1022 may include a delivery catheter 1104 coupled to a handle 1106 with the medical tool 1020 operatively coupled to the handle 1106 at a distal end of the delivery catheter 1104. The delivery catheter 1104 may be sized and configured to be inserted through the sheath 1102 such that the medical tool 1020 may be pushed through the sheath 1102 to the distal end thereof. At least one sensor 23 may be located on the distal end of the sheath 1102. The medical tool 1020 may be partially exposed, at certain stages of delivery, as depicted. The functionality and detail of the various components of the medical tool delivery system 1100 will be described in detail hereafter.

Figure 15:
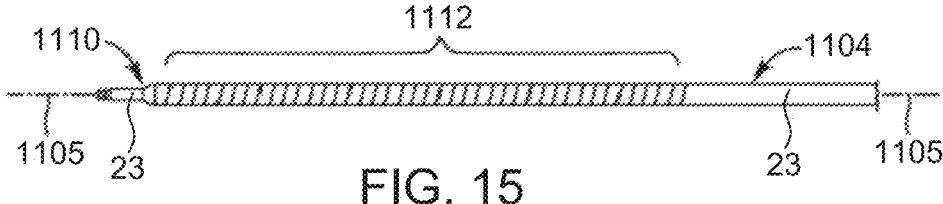
FIG. 15 is a side view of an end portion of a delivery catheter, according to the second exemplary embodiment of the present invention.
Figure 15A:
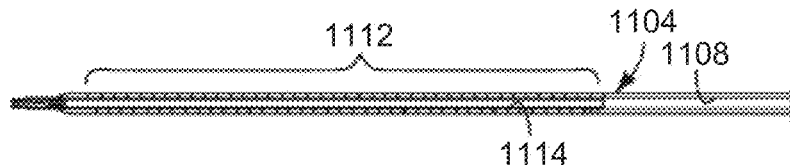
FIG. 15A is a cross-sectional view of the end portion of the delivery catheter, taken along a longitudinal axis of the delivery catheter of FIG. 15.
Figure 15B:
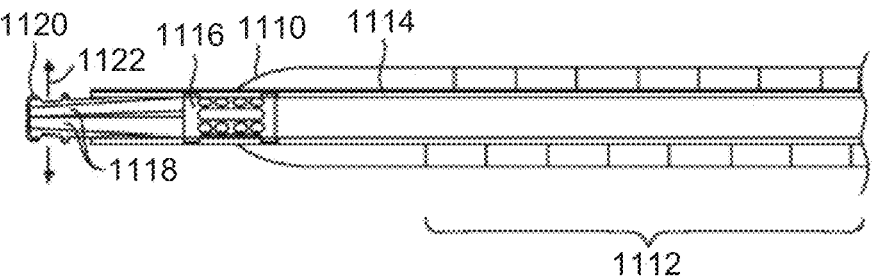
FIG. 15B is an enlarged view of the end portion of the delivery catheter.

With reference now to FIGS. 15, 15A, and 15B, a distal portion of the delivery catheter 1104 will now be described, FIG. 15A being a cross-sectional view of the distal portion of the delivery catheter 1104 along an axis 1105 thereof depicted in FIG. 15 and FIG. 15B being an enlarged cross-sectional view of a portion of the same. The delivery catheter 1104 may define a lumen 1108 extending longitudinally therethrough between a proximal end (not shown) and a distal end 1110 of the delivery catheter 1104. The delivery catheter 1104 may include a shaft (not shown), a spiral cut portion 1112, an inner distal tube 1114, and a collet 1116. The distal portion of the delivery catheter 1104 may include at least one sensor 23. Additionally or alternatively, a proximal portion of the delivery catheter 1104 may include at least one sensor 23. Such distal portion of the delivery catheter 1104 may include enhanced lateral flexibility along the region of the spiral cut portion 1112. That is, the distal portion of the delivery catheter 1104 may be more flexible than portions of the delivery catheter 1104 more proximal than the spiral cut portion 1112. The spiral cut portion 1112 may be formed by spirally or helically cutting a slit into the peripheral structure of the distal portion of the delivery catheter 1104, as depicted. The inner distal tube 1114 may be coupled to the delivery catheter 1104 and within the lumen 1108 of the distal portion of the delivery catheter 1104. The collet 1116 may be positioned and thermally coupled to the distal end 1110 of the delivery catheter 1104 and within the inner distal tube 1114 with collet fingers 1118 extending distally therefrom. The collet fingers 1118 may be sized and configured to latch to the hub of the medical tool (not shown) with nubs 1120 or protrusions extending from free ends of the collet fingers 1118. The collet fingers 1118 are moveable outward, as indicated by arrows 1122, and are biased to an inward position as shown. The collet 1116 and collet fingers 1118 may be made from a metallic material, such as stainless steel or Nitinol, or any other suitable metallic material that can maintain a biasing force. Such inward biasing of the collet fingers 1118 will be discussed in further detail hereafter. With respect to the enhanced flexibility of the delivery catheter 1104 along the spiral cut portion 1112, such enhanced flexibility facilitates the medical tool to self-center upon being deployed in the LAA. In other words, the radial strength of the medical tool (not shown) may be greater than the lateral forces of the delivery catheter 1104 along the spiral cut portion 1112 to, thereby, allow the medical tool to self-center in the LAA in instances where the axis 1105 of delivery catheter cannot be made concentric to the ostium of the LAA during delivery and deployment of the medical tool.

Figures 17, 18, 18A:
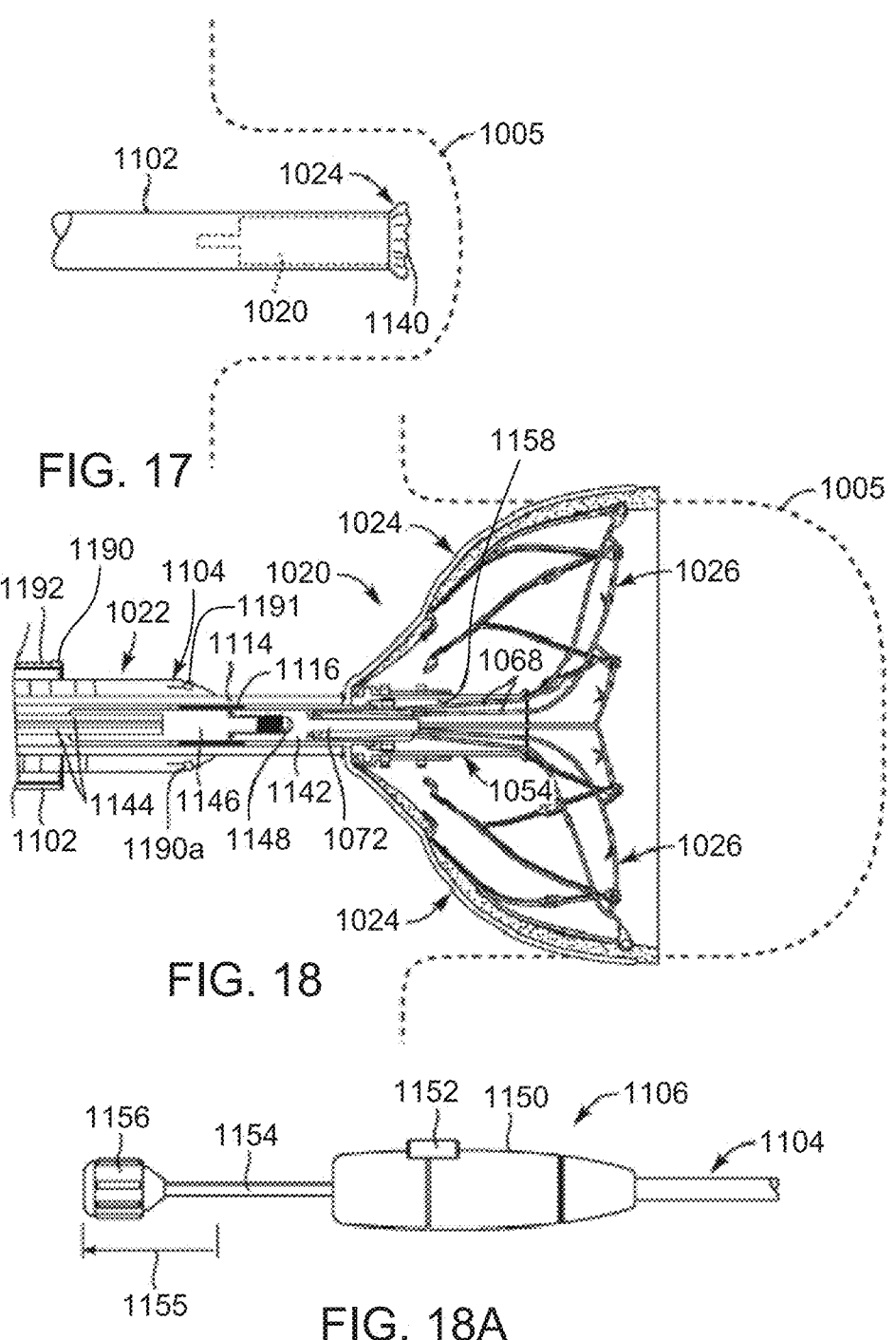
FIG. 17 is a side view of a distal portion of the sheath, depicting a portion of the medical tool exposed at a distal end of the sheath in the LAA, according to the second exemplary embodiment of the present invention.
FIG. 18 is a cross-sectional side view of the distal portion of the delivery system and the medical tool, depicting a sheath withdrawn to deploy the occluder portion of the medical tool in the LAA and depicting the anchor portion in an anchor non-deployed position, according to the second exemplary embodiment of the present invention.
FIG. 18A is a side view of a handle, depicting the handle in a first position corresponding to the anchor non-deployed position, according to the second exemplary embodiment of the present invention.

Now with reference to FIGS. 16A, 16B, and 16C, description of steps that may be employed for loading the medical tool 1020 into the sheath 1102 will now be provided. For example, the delivery catheter 1104 may include a loader 1124 sized and configured to facilitate loading the occluder portion 1024 of the medical tool 1020 into the sheath 1102 so that the delivery catheter 1104 can push the occluder portion 1024 through the sheath 1102 to a distal portion thereof. With reference to FIG. 16A, the loader 1124 may include a tube portion 1126 and a handle portion 1128. The loader 1124 may be slideably positioned over the delivery catheter 1104 such that the delivery catheter 1104 extends through a bore defined through the loader 1124. The loader 1124 may be moved over the distal end of the delivery catheter 1104 and manually moved or forced over the occluder portion 1024 of the medical tool 1020 so that occluder portion 1024 moves to a constricted position enclosed within the tube portion 1126. However, prior to moving the loader 1124 over the occluder portion 1024, the anchor portion should be in a non-deployed position such that an actuator knob and plunger shaft of the handle 1106 should be moved to a proximal position, as depicted in FIGS. 18 and 18A. Referring back to FIG. 16A, once the loader 1124 is moved completely over the occluder portion 1024, the medical tool 1020 may then be advanced through the sheath 1102. The sheath 1102, at this point, has already been advanced through the circulatory system to the heart with a distal portion of the sheath 1102 positioned in the LAA (not shown), employing typical techniques known in the art.

As depicted in FIGS. 16B and 16C, the loader 1124 may be inserted into the sheath 1102 and, more particularly, a sheath hub 1130. The sheath hub 1130 may be coupled at a proximal end of the sheath 1102. The components of the sheath hub 1130 may include a valve 1132 and a sheath fluid port 1134. The valve 1132 may be a rotating hemostasis valve, such as a Touhy Borst valve or the like, configured to constrict or limit back-flow of blood from the sheath 1102 upon rotation of the valve 1132. The sheath fluid port 1134 may extend from the sheath hub 1130 and may be sized and configured to flush or aspirate air from the sheath 1102 that may become trapped upon loading the medical tool 1020 into the sheath 1102. The loader 1124 may also include a valve positioned around the delivery catheter 1104 to maintain hemostasis while inserted into the sheath hub 1130.

As set forth, the loader 1124 may be mated or inserted into the sheath hub 1130 with a snap or click fit via nubs 1136 at the distal end of the tube portion 1126 and a rib (not shown) within a bore 1138 defined in the sheath hub 1130. Once the loader 1124 is positioned within the sheath hub 1130, the delivery catheter 1104 may be advanced through a lumen defined longitudinally in the sheath 1102 such that the distal end of the delivery catheter 1104 moves to a distal portion of the sheath 1102 to expose a distal tip of the occluder portion 1024 of the medical tool 1020 from the distal end of the sheath 1102. With this arrangement, the distal tip of the occluder portion 1024 may be exposed at the distal end of the sheath 1102 and provides, due to the occluder material, a cushioned tip 1140, without any exposed metal frame members, facilitating an atraumatic entry into the LAA, thereby, reducing the potential of effusions in the LAA.

Referring to FIGS. 17 through 21, deployment and detachment of the medical tool 1020 in an LAA 1005 (shown in outline) relative to the delivery system 1022 will now be described. With respect to FIGS. 17 and 18, upon the physician positioning the distal portion of the sheath 1102 in the LAA 1005 with the medical tool 1020 positioned at the distal portion of the sheath 1102 with the cushioned tip 1140 of the occluder portion 1024 exposed at the distal end of the sheath 1102, the physician may atraumatically position the distal portion of the sheath 1102 to a desired location in the LAA 1005. Once the desired location is determined, the physician can deploy the occluder portion 1024 of the medical tool 1020. Such may be employed by simply withdrawing the sheath 1102 or manually moving the sheath 1102 in a proximal direction. As the sheath 1102 is withdrawn, the occluder portion 1024 self-expands to an occluder deployed position with the anchor portion 1026 maintained in an anchor non-deployed position, as depicted in FIG. 18.

With respect to FIG. 18, a distal portion of the delivery catheter 1104 coupled to the medical tool 1020 is shown. The delivery catheter 1104 of this embodiment is coupled to the medical tool 1020 with an occluder hub nut 1142 and collet 1116 arrangement. For example, the distal portion of the delivery catheter 1104 includes the inner distal tube 1114 and an actuator shaft 1144. The actuator shaft 1144 may include a layered coil, such as a speedometer cable, at a distal end portion thereof, which may be coupled to an inner distal connector 1146 moveable within the collet 1116. As previously set forth, the collet 1116 may include collet fingers 1118 extending distally from the collet 1116. The inner distal connector 1146 may include threads sized and configured to couple to the occluder hub nut 1142 and, more particularly, to a threaded screw hole 1148 defined in the occluder hub nut 1142. The occluder hub nut 1142, at a distal end thereof, may include the splined sleeve 1072. As previously set forth, the splined sleeve 1072 may be sized and configured to couple end portions of each of the anchor actuator arms 1068. Alternatively or additionally, the inner distal connector 1146 and occluder hub nut 1142 may be reversed such that the inner distal connector 1146 includes a nut configuration and the occluder hub nut 1142 includes a screw configuration. In either case, the medical tool 1020 may be threadably coupled to the delivery catheter 1104.

With reference to FIG. 18A, one embodiment of the handle 1106 is depicted. The handle 1106 may include a handle housing 1150, an anchor actuator release button 1152, a plunger shaft 1154, and an actuator knob 1156. The handle housing 1150 may be coupled to a proximal portion of the delivery catheter 1104. The plunger shaft 1154 and actuator knob 1156 is shown in a first position that correlates to the anchor portion 1026 being in a non-deployed position (see FIG. 18). The plunger shaft 1154 and actuator knob 1156 may be moved bi-linearly between a first position and a second position while depressing the anchor actuator release button 1152. The functions and various components of the handle 1106 will become apparent to one of ordinary skill in the art as discussed in further detail hereafter.

As depicted in FIGS. 18 and 18A, the anchor portion 1026 of the medical tool 1020 is in an anchor non-deployed position. The actuator knob 1156 and plunger shaft 1154 are moved to the first position, as indicated by arrow 1155 that corresponds to the anchor non-deployed position prior to loading the medical tool 1020 into the loader 1124 and then into the sheath 1102 (see FIGS. 16A and 16B). In the anchor non-deployed position, the inner distal connector 1146 is threadably coupled to the occluder hub nut 1142 and is positioned proximal the hub 1054 with the anchor portion 1026 in a first position or an anchors non-deployed position or, otherwise said, an anchors-in position with a portion of the anchor actuator arms 1068 proximal the hub 1054 and within a bore 1158 defined in the hub 1054. Further, in the anchor non-deployed position, the plunger shaft 1154 and knob 1156 of the handle 1106 may be in a proximal or first position as well. With this arrangement, a physician may determine the most favorable position of the medical tool 1020 within the LAA 1005 with the occluder portion 1024 in the deployed position prior to deploying the anchor portion 1026.

Figure 19:
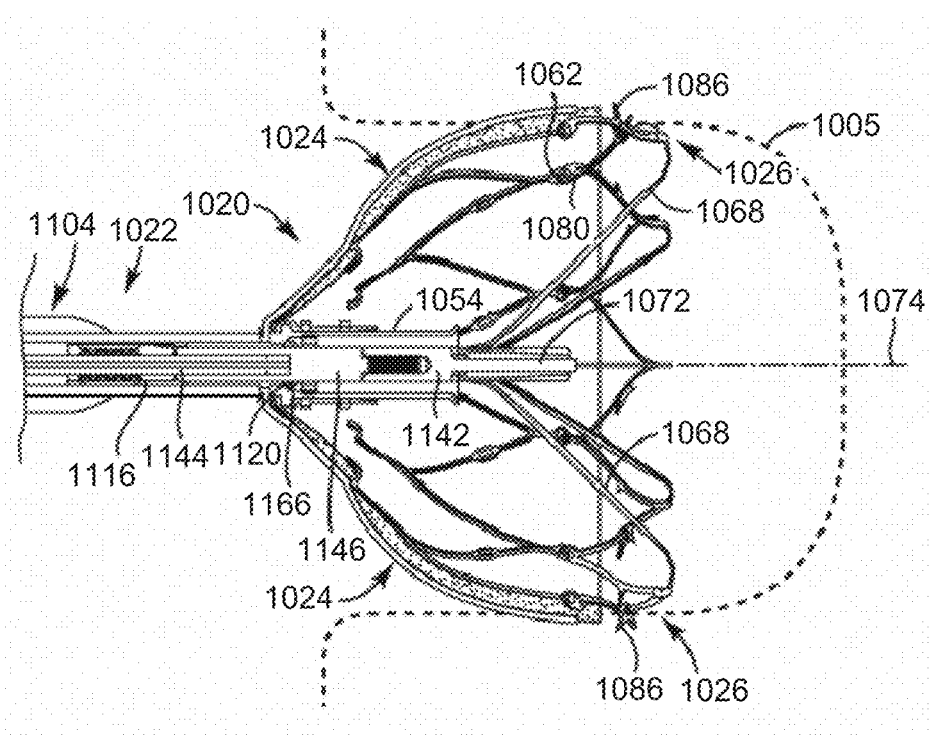
FIG. 19 is a cross-sectional side view of the distal portion of the delivery system and the medical tool, depicting both the occluder portion and the anchor portion in an anchor deployed position in the LAA, according to the second exemplary embodiment of the present invention.
Figure 19A:
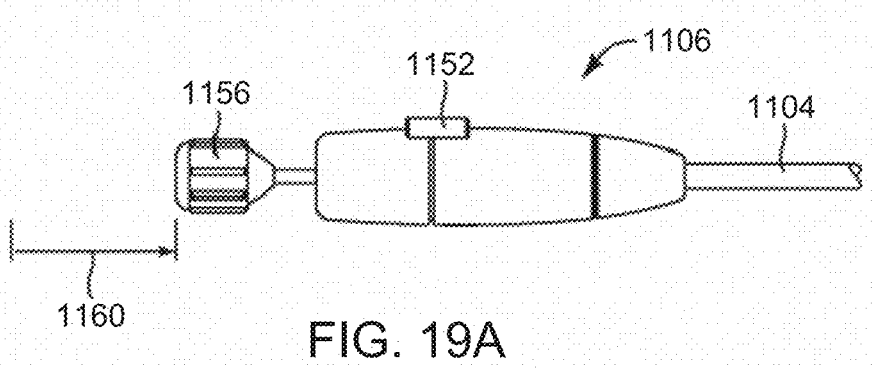
FIG. 19A is a side view of the handle, depicting the handle in a second position corresponding to the anchor deployed position, according to the second exemplary embodiment of the present invention.

Now turning to FIGS. 19 and 19A, the anchor portion 1026 of the medical tool 1020 may be moved to an anchor deployed position or anchor-out or anchor second position once the physician determines the deployed occluder portion 1024 is positioned in the LAA 1005 as desired. Such anchor deployed position may be employed by manually moving the actuator knob 1156 distally, as indicated by arrow 1160, while also depressing the release button 1152. In the anchor deployed position, the inner distal connector 1146 and occluder hub nut 1142 are also moved distally from the collet 1116 and into the hub 1054 or through the hub 1054. Such linear distal movement also moves the anchor actuator arms 1068, coupled to the splined sleeve 1072, from a distal portion of the delivery catheter 1104, through and out of the hub 1054 to an everted, deployed position or an expanded position such that the anchor portion 1026 unfolds and expands radially by pivoting or rotating at the hinged connection (i.e., at occluder and anchor eyelets 1062, 1080) between the occluder portion 1024 and anchor portion 1026. At the anchor deployed position, hooks 1086 or tines of the anchor portion 1026 are sized and configured to grab tissue and prevent movement so as to effectively anchor the medical tool 1020 within the LAA 1005. Additionally or alternatively, the hooks 1086 or tines of the anchor portion 1026 are sized and configured to grab tissue and prevent movement so as to effectively anchor the medical tool 1020 within the left atrium. Once the anchor portion 1026 is deployed, the physician may view the medical tool 1020 through imaging techniques to ensure proper positioning of the medical tool 1020 in the LAA 1005 while also performing stability tests by pulling proximally on the handle 1106 to ensure the medical tool 1020 is effectively engaging the LAA 1005. Such imaging techniques may be enhanced by markers strategically located on the medical tool 1020 and delivery catheter 1104 to provide imaging information to the physician. Such markers may be made from a radiopaque material, such as platinum, gold, tantalum, or alloys thereof, or any other suitable radiopaque materials that are biocompatible.

The hooks 1086 of the anchor portion 1026 may extend both distally and proximally so as to substantially prevent movement of the medical tool 1020 in both the proximal and distal directions relative to the LAA 1005. The hooks 1086 may include an acute angle 1088 (FIG. 13A) relative to the axis 1074 of the medical tool 1020 or the struts of the anchor zig-zag portion 1070. The hooks 1086 are configured to grab and may dig at the tissue of the LAA 1005. Such hooks 1086 may be sized, oriented, and configured to prevent puncture or piercing of the hooks 1086 all the way through the tissue of the LAA 1005, but provide effective and even aggressive engagement with the tissue to provide safe anchoring of the medical tool 1020 in the LAA 1005.

If the physician is dissatisfied with the location or engagement of the medical tool in the LAA, the physician may readily disengage the anchor portion 1026 from the tissue of the LAA by simply moving the actuator knob 1156 in the proximal direction to the first position (FIG. 18A), which simultaneously moves the actuator shaft 1144 proximally and, thus, pivots the anchor portion 1026 to a disengaged or anchor non-deployed position. The physician may then re-position the occluder portion 1024 within the LAA 1005 and, once satisfied with the location of the occluder portion 1024 in the LAA 1005, the physician may readily move the actuator knob 1156 forward or a distal direction to pivot and re-engage the anchor portion 1026 with the tissue of the LAA 1005. The physician may then determine again through imaging and stability tests if the medical tool 1020 is positioned in the LAA 1005 in an effective and safe manner that satisfies the physician. As can be readily understood, the steps of re-positioning the occluder portion 1024 and re-engaging the anchor portion 1026 of the medical tool 1020 can be repeated until the physician is satisfied.

Figure 20:
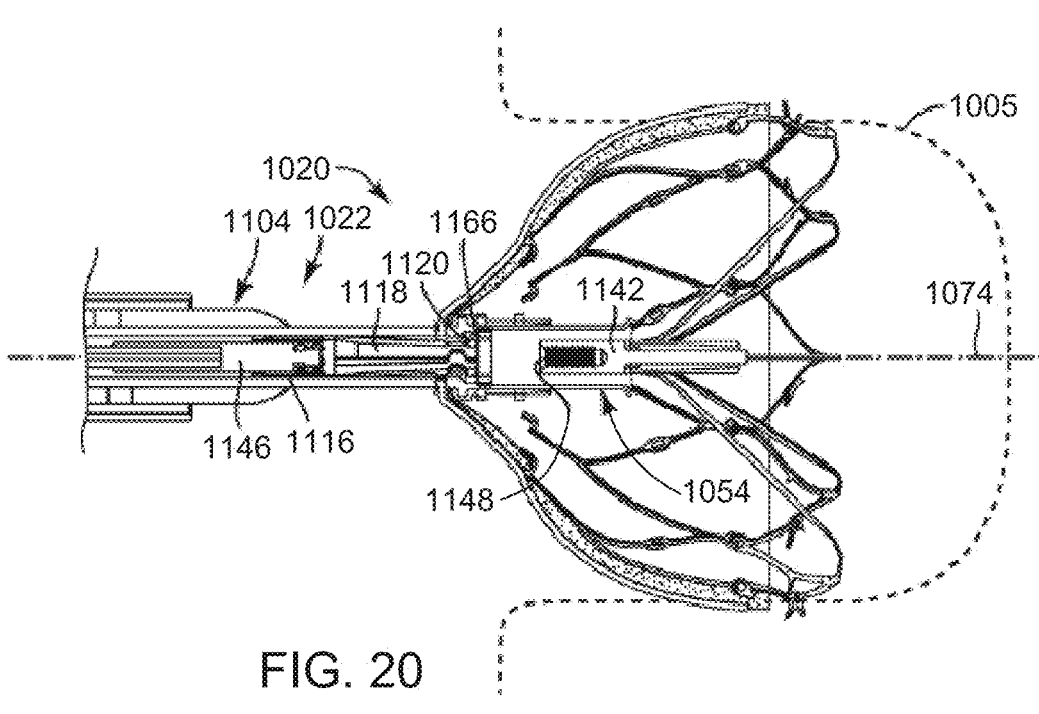
FIG. 20 is a cross-sectional side view of the distal portion of the delivery system and the medical tool, depicting the delivery system in the process of being released from the medical tool in the LAA, according to the second exemplary embodiment of the present invention.
Figure 20A:
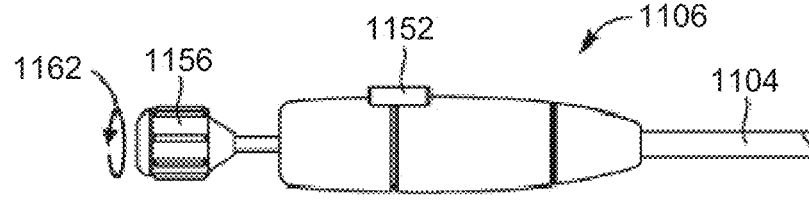
FIG. 20A is a side view of the handle, depicting a portion of the handle being rotated for releasing the medical tool, according to the second exemplary embodiment of the present invention.
Figure 20B:
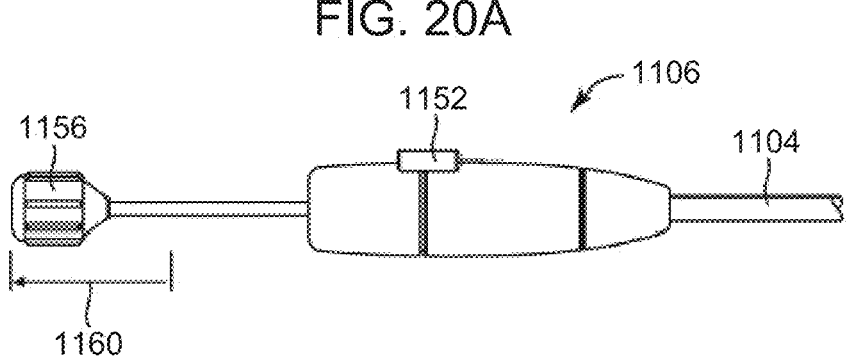
FIG. 20B is a side view of the handle, depicting a portion of the handle actuated from the second position to the first position, according to the second exemplary embodiment of the present invention.
Figure 21:
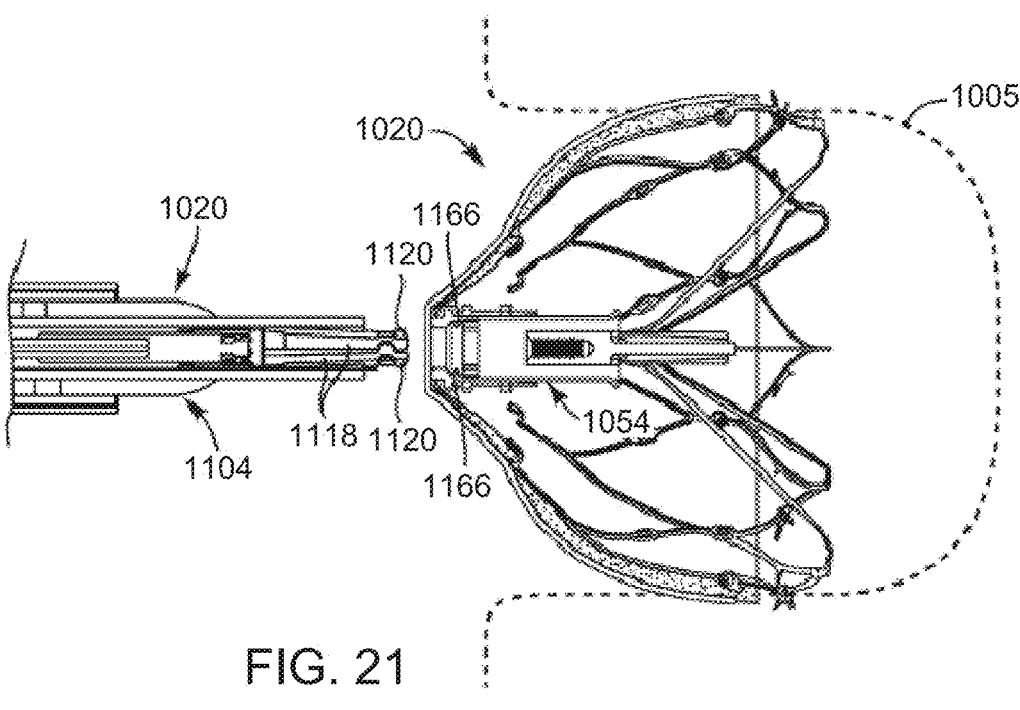
FIG. 21 is a cross-sectional side view of the distal portion of the delivery system and the medical tool, depicting the delivery catheter fully released from the medical tool, according to the second exemplary embodiment of the present invention.

Now referring to FIGS. 20, 20A, and 20B, the functions of releasing the medical tool 1020 will now be described. The medical tool 1020 may be detached or released by unscrewing the inner distal connector 1146 from the screw hole 1148 defined in the occluder hub nut 1142. Such releasing may be employed by rotating the actuator knob 1156 of the handle 1106 counter-clockwise several turns, as indicated by arrow 1162, until the inner distal connector 1146 unwinds from the screw hole 1148 of the occluder hub nut 1142. The actuator knob 1156 may then be pulled proximally back to the first position, as indicated by arrow 1164, while depressing the release button 1152, which facilitates movement of the inner distal connector 1146 in the proximal direction. As the inner distal connector 1146 is moved proximally through or into the collet 1116, the collet fingers 1118 extending distally from the collet 1116 collapse inward since the collet fingers 1118 may be biased toward an inward position. In other words, prior to the inner distal connector 1146 being unwound, the collet fingers 1118 may be held in an outer position substantially concentric with the axis 1074 of the medical tool 1020, which maintains the delivery catheter 1104 locked to the medical tool 1020. The collet fingers 1118 include outward extending nubs 1120 that are held against an abutment 1166 within the hub 1054 (also shown in FIG. 19). In this manner, once the inner distal connector 1146 is unscrewed from the occluder hub nut 1142 and moved to a proximal position away from the collet fingers 1118, the collet fingers 1118 flexibly collapse with a bias to an inward position to move the nubs 1120 away from the abutment 1166 in the hub 1054, thereby, unlocking or unlatching the delivery catheter 1104 from the medical tool 1020. The delivery catheter 1104 may then be removed from the medical tool 1020 with the collet fingers 1118 collapsed and the nubs 1120 moved proximally from the abutment 1166 within the hub 1054 as depicted in FIG. 21.

Figure 22:
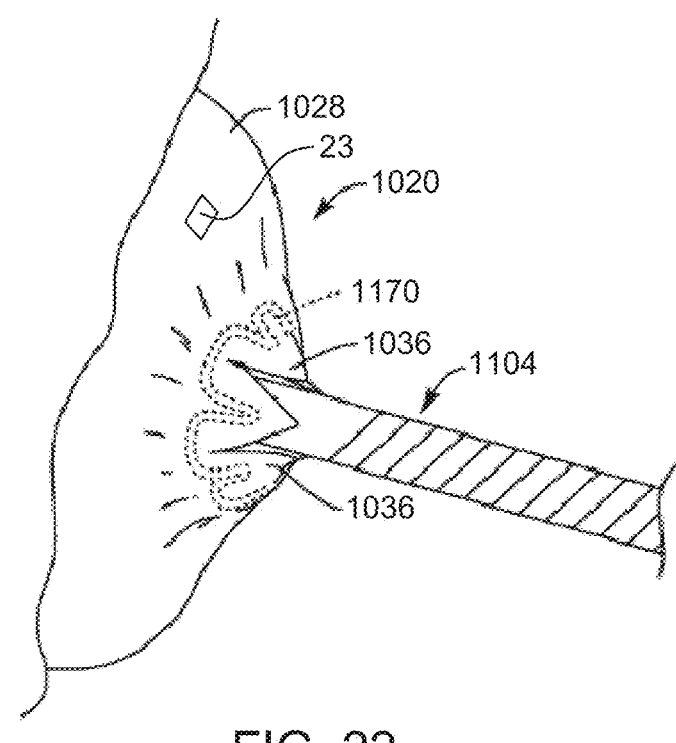
FIG. 22 is a partial perspective view of the proximal side of the medical tool coupled to the delivery system, according to the second exemplary embodiment of the present invention.

With respect to FIGS. 12 and 22, a moveable portion that may include a spring 1170 is depicted. The moveable portion may include a spring 1170 with a polymeric covering in the form of polymeric flaps or occluder flaps 1036. Such moveable portion having the spring 1170 may be sized and configured to close-off the bore 1158 of the hub 1054 once the delivery catheter 1104 is released from the medical tool 1020. The spring 1170 may include a clover configuration or any other suitable configuration to effectively close-off the hub 1054. The spring 1170 may move between a first biased position (or open first position) and a second relaxed position (or closed second position). The first biased position of the spring 1170 (shown in outline form) is depicted in FIG. 22, which is the position of the spring 1170 with the delivery catheter 1104 coupled to the hub 1054. The position of the delivery catheter 1104 attached to the hub 1054 holds the spring 1170 in the biased or open first position. Once the delivery catheter 1104 is removed from the hub 1054, the spring 1170 may automatically move to the closed, second relaxed position (see FIG. 12) with the occluder flaps 1036 (see also FIG. 11) substantially minimizing or eliminating any through hole on the proximal face and adjacent the hub 1054. In the second relaxed position of the spring 1170, the bore 1158 defined in the hub 1054 is substantially closed-off with occluder flaps 1036, leaving only a cross-like slit (as depicted by adjacently extending occluder flaps 1036 in FIG. 11) and substantially eliminating any metal exposed at the hub 1054. In this manner, the occluder flaps 1036, in the closed second position, advantageously provides a surface at the proximal face of the device without exposed metal at the hub 1054 and, further, provides a contiguous surface with the polymeric material of the occluder portion that closes-off the hub 1054.

As previously set forth, the spring 1170 may be embedded in the occluder material or tissue growth member 1028 or attached to an inner occluder material surface such that the spring 1170 may include various layers and/or folds of, for example, ePTFE, with one or more slits defining the flaps 1036 that facilitates interconnection of the delivery catheter 1104 to the hub 1054 when the spring 1170 is in the first biased position but then may substantially close-off the bore 1158 defined in the hub 1054 when in the second relaxed position. Such arrangement is advantageous to substantially prevent blood flow through the hub 1054 or to substantially prevent the potential of migrating emboli or thrombus from the hub 1054 itself once the medical tool 1020 is positioned in the LAA. In this manner, the spring 1170 facilitates closing-off the through hole of the hub 1054 and/or covers any exposed metal at the hub so that emboli or thrombus that may collect on the metal is prevented from escaping from the hub. In other words, the flaps 1036 provide a substantially impassible barrier relative to otherwise potential migrating emboli or thrombus at the hub 1054.

Figure 23A:
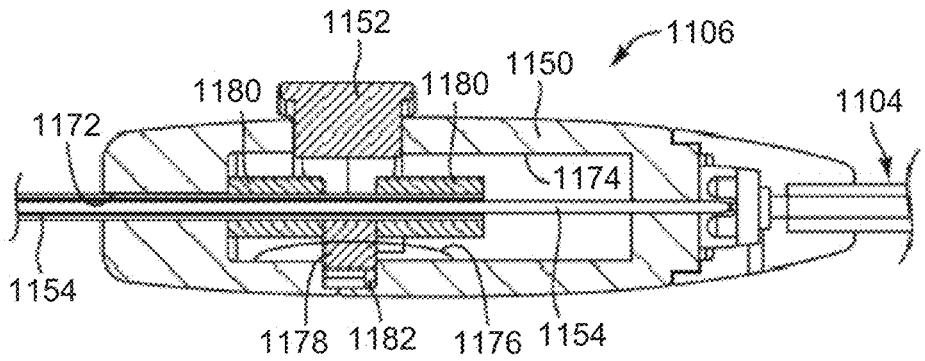
FIGS. 23A and 23B are cross-sectional side views of the handle, depicting a release button in a first and second position, respectively, to facilitate actuation of a plunger shaft, according to the second exemplary embodiment of the present invention.
Figure 23B:
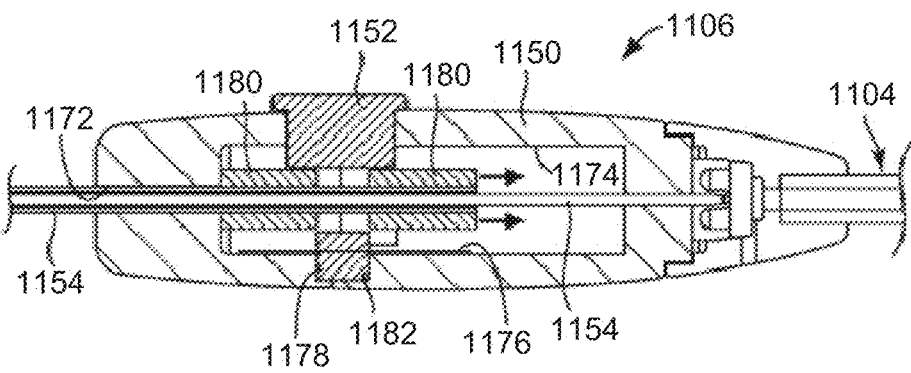

Now referring to FIGS. 23A and 23B, actuation of the release button 1152 of the handle 1106 is depicted. The handle housing 1150 defines a hole 1172 that may extend along a longitudinal axis of the handle housing 1150 and may be sized to hold the plunger shaft 1154 to move bi-linearly therethrough. The handle housing 1150 may also define a hollow portion 1174 therein. The plunger shaft 1154 may extend through the handle housing 1150 and be coupled to components coupled to actuator shaft 1144 and the inner distal connector 1146 at the distal portion of the delivery catheter 1104 (see FIG. 9). The handle 1106 also may include a leaf spring 1176 configured to bias against the release button 1152. The release button 1152 may include a button post 1178. The leaf spring 1176 may be coupled to the button post 1178 to bias the release button 1152 to a non-depressed position or first position. The plunger shaft 1154 may also include two travel stops 1180 fixed thereto. By depressing the release button 1152 to a depressed position or second position, the button post 1178 depresses the leaf spring 1176 and moves within a cavity 1182. Once the button post 1178 is moved within the cavity 1182, the travel stops 1180 coupled to the plunger shaft 1154 may then freely move distally (and then back proximally) past the button post 1178 a predetermined distance gauged by the travel stops 1180 within the hollow portion 1174 defined by the handle housing 1150. In this manner, the plunger shaft 1154 may move the predetermined distance which directly corresponds with the distance or length moved by the actuator shaft 1144 and actuation of the anchor portion of the medical tool 1020 between the anchor non-deployed position and anchor deployed position (see FIGS. 18 and 19).

Referring back to FIG. 18, the sheath 1102 may include an imaging device 1190. The imaging device 1190 may be sized and configured to be positioned at a distal end of the sheath 1102 and may include one or more lines 1192 extending from the imaging device 1190 and proximally toward the sheath hub 1130 (FIG. 15C) for transferring imaging information from the imaging device 1190 to a computer and a display (not shown), as known to one of ordinary skill in the art, and viewable by the physician in real-time. The sheath 1102, upon being withdrawn from the occluder portion 1024, being positioned substantially concentric or proximal of the medical tool 1020, may be at a vantage point and location in the left atrium adjacent the LAA to provide detailed imaging information otherwise not readily available to the physician. The imaging device 1190 may be an ultrasound imaging device or any other suitable imaging device known in the art. The imaging device 1190 a may be positioned proximal a distal end of the delivery catheter 1104 in a similar manner to that described above. The distal end of the delivery catheter 1104 and/or sheath 1102 may include one or more positioning sensors 1191. The positioning sensors 1191 may be configured to sense pressure, flow, and any other cardiac dynamics that may be useful to the physician. In this manner, the positioning sensors 1191 and/or imaging device 1190, may provide additional information to assist the physician to accurately position the medical tool 1020 in the LAA 1005.

Figures 24A, 24B:
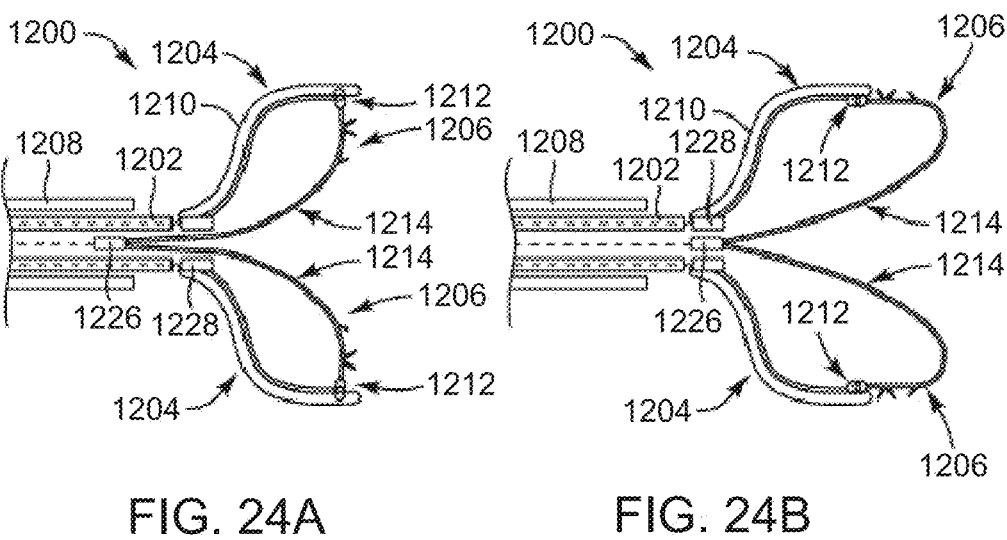
FIGS. 24A and 24B are simplistic side profile views of another embodiment of a medical tool, depicting the medical tool in an anchor non-deployed position and an anchor deployed position, respectively.

Now with reference to FIGS. 24A and 24B, another embodiment of a medical tool 1200 coupled to a distal portion of a delivery catheter 1202, the medical tool 1200 (depicted in a simplistic profile view) in a partially deployed position and fully deployed position, respectively, is provided. As in previous embodiments, the medical tool 1200 may include an occluder portion 1204 and an anchor portion 1206 that may be separately deployed. For example, once a sheath 1208 is positioned in the LAA (not shown) with the medical tool 1200 at a distal end portion thereof, the sheath 1208 is withdrawn to deploy an occluder portion 1204 of the medical tool 1200 or to partially deploy the medical tool 1200. Once the occluder portion 1204 is deployed, then the anchor portion 1206 may be deployed, to fully deploy the medical tool 1200.

In this embodiment, the occluder portion 1204 is substantially similar to the previous embodiment, except the tissue growth member 1210 is attached to an outer surface of the frame components of the occluder portion 1204. The tissue growth member 1210 of this embodiment may include similar layering of one or more materials as set forth for the tissue growth member described in detail relative to FIG. 1B. Further, although the anchor portion 1206 may be hingably coupled to the occluder portion 1204 with a hinge arrangement 1212 and, in many respects functions similar to the previous embodiment, the anchor portion 1206 of this embodiment includes multiple separate and distinct anchor frame segments 1214, best shown in FIG. 25.

Figure 25:
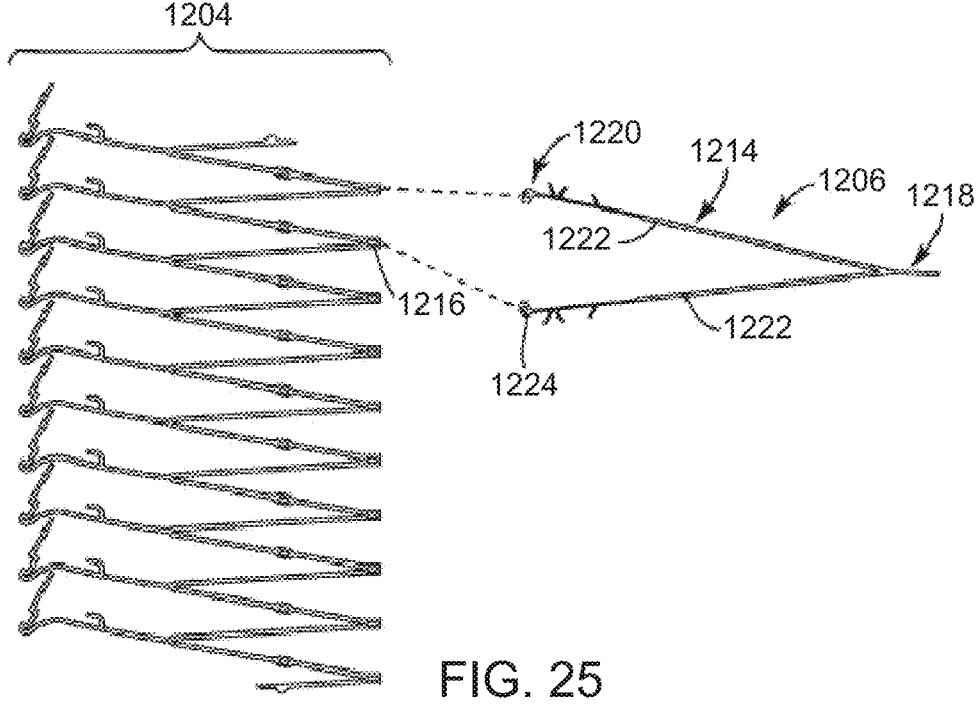
FIG. 25 is a top view of the occluder portion and the anchor portion of the medical tool of FIGS. 24A and 24B, depicting frame components cut from a flat sheet.

With reference to FIG. 25, the frame components of the occluder portion 1204 and the anchor portion 1206 are depicted in, for example, a preformed state subsequent to being laser cut from a flat sheet of super elastic material, such as Nitinol. For simplicity purposes, there is only one anchor frame segment 1214 shown, but in this embodiment, there may be five anchor frame segments 1214 to correspond and couple to, for example, occluder frame apertures 1216 of the occluder portion 1204. As shown, the frame components of the occluder portion 1204 may be substantially similar to the frame components of the occluder portion 1204 described in the previous embodiment relative to FIG. 13.

With respect to the anchor frame segments 1214, each anchor frame segment 1214 may extend between a first end 1218 and second end 1220 with two actuator arms 1222 extending therebetween such that each anchor frame segment 1214 may exhibit a "Y" or "V" configuration in the pre-formed state. Each actuator arm 1222 may include an anchor hinge aperture 1224 at the second end 1220 and, at the first end 1218, the actuator arm 1222 may be coupled to a collar arrangement 1226 or splined sleeve, similar to that of the previous embodiment. With this arrangement, the actuator arms 1222, as depicted in FIGS. 24A and 24B, may pivot about the occluder portion 1204 at the hinge arrangement 1212. Further, the actuator arms 1222 may form a loop configuration or loop extension in the anchor deployed position with the first end 1218 of the actuator arms 1222 moveable or actuatable through the hub 1228 of the medical tool 1200.

Figures 26A, 26B:
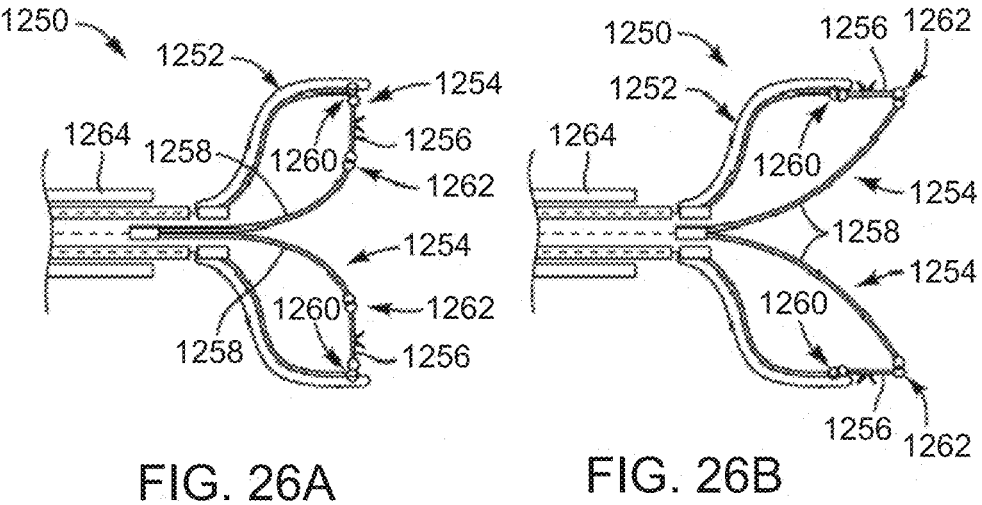
FIGS. 26A and 26B are simplistic side profile views of another embodiment of a medical tool, depicting the medical tool in an anchor non-deployed position and an anchor deployed position, respectively.
Figure 27:
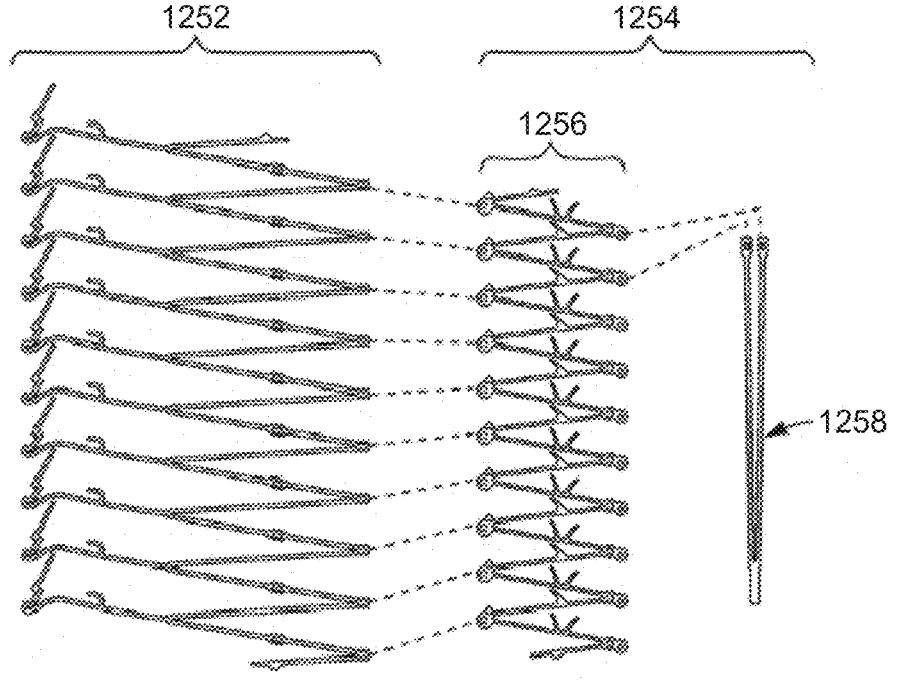
FIG. 27 is a top view of the occluder portion and the anchor portion of the medical tool of FIGS. 26A and 26B, depicting frame components cut from a flat sheet.

Now with reference to FIGS. 26A, 26B, and 27, another embodiment of a medical tool 1250 depicted in a partially deployed position (FIG. 26A) and a fully deployed position (FIG. 26B), similar to previous embodiments, is depicted. In this embodiment, the occluder portion 1252 can be similar to the previous embodiments, but the anchor portion 1254 may include an anchor zig-zag portion 1256 and loop extensions 1258 or actuator arms as separate anchor frame components. In this embodiment, the medical tool 1250 may include a dual hinge arrangement. For example, the occluder portion 1252 may be hingably coupled to an anchor zig-zag portion 1256 with a first hinge arrangement 1260 and the anchor zig-zag portion 1256 may be hingably coupled to the loop extensions 1258 with a second hinge arrangement 1262. The profile and functionality of the medical tool 1250 may be similar to the previous embodiments, except the loop extensions 1258 may take a more direct inward angle from the anchor zig-zag portion 1256 due to the second hinge arrangement 1262 therebetween. Similar to the embodiment of FIG. 25, this embodiment may include ten loop extensions 1258 or actuator arms, though for simplicity purposes only two loop extensions 1258 (as a single loop extension segment) are shown in FIG. 27. It should be noted that the embodiments of FIGS. 24 and 26 also provide the feature to facilitate a cushion tip (not shown) as depicted in FIG. 17 when constricted in the sheath 1264. Further, it should be noted the alternatives depicted and described relative to FIGS. 11, 24 and 26 include similar features and structure and, therefore, the descriptions provided in one embodiment may also be applicable to the other described embodiments.

Figures 28, 28A, 28B:
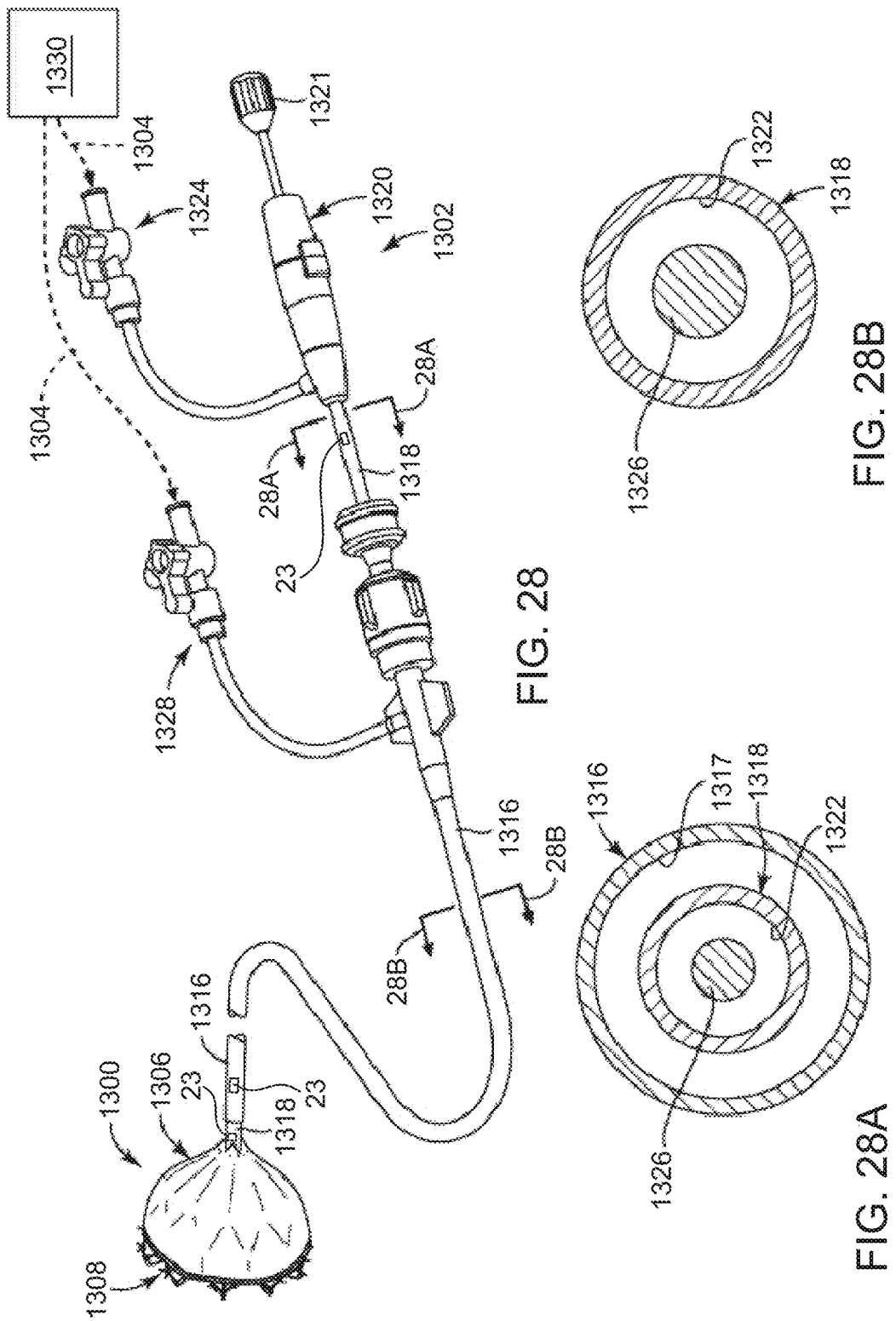
FIG. 28 is a perspective view of a medical tool delivery system, depicting a medical tool attached and deployed at a distal end of the delivery system, according to the second exemplary embodiment of the present invention.
FIG. 28A is a cross-sectional view of section 28A of FIG. 28, depicting a lumen defined in a proximal portion of a catheter of the delivery system, according to another embodiment of the present invention.
FIG. 28B is a cross-sectional view of section 28B of FIG. 28, depicting a sheath lumen of a sheath with the catheter of the delivery system therein, according to another embodiment of the present invention.
Figure 29:
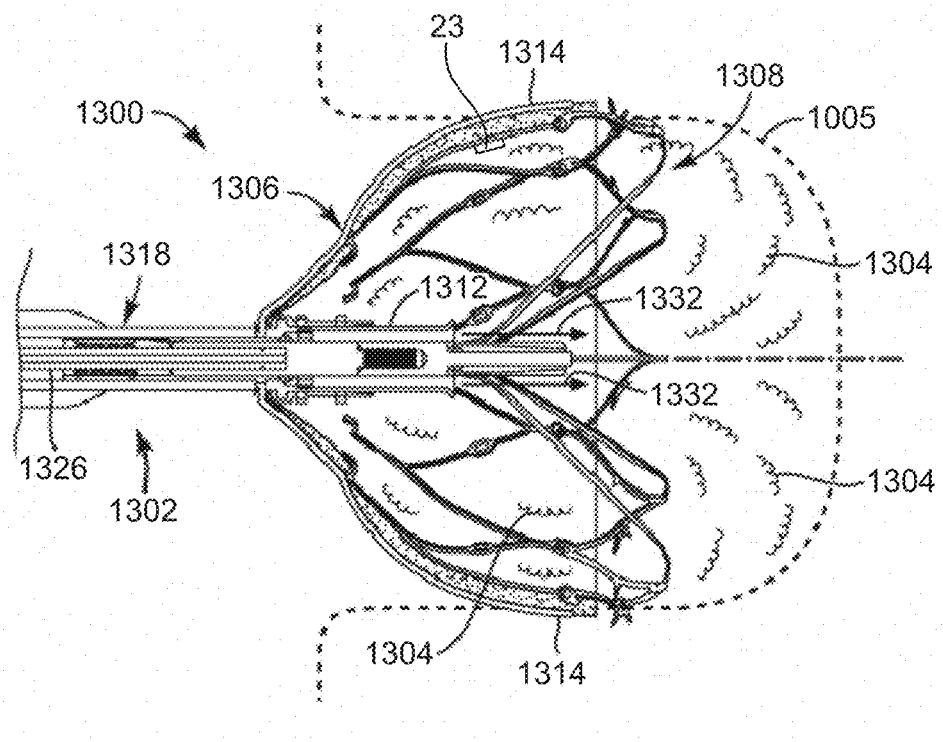
FIG. 29 is a cross-sectional view of the medical tool and the distal portion of the delivery system, depicting a fluid flowing from a hub of the medical tool and into the left atrial appendage, according to the second exemplary embodiment of the present invention.

Now with reference to FIGS. 28 through 30, another alternative of a medical tool 1300 and a medical tool delivery system 1302 for modifying an LAA 1005 of the heart is provided. Under this alternative of the second exemplary embodiment, the structural components and functionality of the medical tool 1300 and the medical tool delivery system 1302 may be substantially similar to any one of the embodiments previously described. For example, the medical tool 1300 may include an occluder portion 1306 and an anchor portion 1308, similar to that described above.

Under this alternative, upon the medical tool 1300 being positioned within the LAA 1005 with the anchor portion 1308 deployed and engaged with tissue of the LAA 1005, the medical tool delivery system 1302 and the medical tool 1300 may include a common flow path 1310 defined therethrough for injecting a fluid 1304 through a hub 1312 of the medical tool 1300 and to a distal side of the medical tool 1300 and into the LAA 1005. One important aspect of this alternative may be that the occluder portion 1306 of the medical tool includes a substantially non-permeable material of, for example, a polymeric material, such as foam and/or ePTFE, described in earlier embodiments herein as the tissue growth member. The ePTFE may be the material that is non-permeable.

The occluder portion 1306 of the medical tool 1300 may include a polymeric material, such as the before-described foam and/or ePTFE. The polymeric material may include a bio-agent coated over or impregnated within the polymeric material. Such bio-agent may be configured to enhance tissue growth and endothelization over the proximal side of the occluder portion 1306 of the medical tool 1300. Alternatively or additionally, the polymeric material may include a coating thereon that may be an anti-thrombotic coating, such as Heprin. The occluder portion may include a biological tissue, in addition to or instead of the before-described polymeric material. Such biological tissue may be a biological sourced tissue, such as pericardial tissue and/or peritoneum tissue, or any suitable biological tissue that is biocompatible as known in the art. Further, the biological tissue may be non-permeable, strong, and thin so as to readily be moved with the occluder portion frame structure between collapsed and expanded configurations. Further, the non-permeable characteristics of the pericardial tissue may function to substantially maintain fluid 1304 in the LAA 1005 upon the medical tool being positioned in the LAA. Alternatively or additionally, the biological tissue may be permeable or include portions with permeable characteristics and other portions with non-permeable characteristics.

With reference to FIGS. 28, 28A and 28B, the medical tool delivery system 1302 includes a sheath 1316, a delivery catheter 1318 coupled to a handle 1320, and the medical tool 1300 coupled to a distal end of the delivery catheter 1318, similar to that described and depicted relative to FIG. 14 herein (as well as other embodiments herein). The delivery catheter 1318 extends between a proximal end and a distal end such that the proximal end is coupled to the handle 1320 and the distal end of the delivery catheter 1318 is coupled to the implantable medical tool 1300. Further, the delivery catheter 1318 defines a lumen 1322 extending along a longitudinal length of the delivery catheter 1318. The handle 1320 may include a fluid port 1324 sized and configured to directly communicate with the lumen 1322 of the delivery catheter 1318. Also, the delivery catheter 1318 may include an actuator shaft 1326 (coupled to the handle 1320 and actuatable by the actuator knob 1321) extending therethrough for controlling actuation of the anchor portion 1308 of the medical tool 1300. With this arrangement, fluid, may be injected through the fluid port 1324 of the handle 1320 and directly through the lumen 1322 of the delivery catheter 1318 such that fluid may advance toward the medical tool 1300. Further, the distal portion of the delivery catheter 1318 may include at least one sensor 23. Additionally or alternatively, a proximal portion of the delivery catheter 1318 may include at least one sensor 23.

As in previous embodiments, the delivery catheter 1318 and the medical tool 1300 coupled at the distal end thereof may be sized and configured to be pushed through a sheath lumen 1317 defined along a length of the sheath 1316. The sheath 1316 may also include a sheath fluid port 1328 sized and configured to inject fluid through the sheath lumen 1317 and to exit from the distal end of the sheath 1316. Further, the distal portion of the sheath 1316 may include at least one sensor 23.

The fluid may be injected through the fluid port 1324 of the handle 1320, as well as the sheath fluid port 1328 of the sheath 1316, with an injection device 1330. The injection device 1330 may be a syringe for manual injection through the fluid port 1324 of the handle 1320 or through the sheath fluid port 1328 of the sheath 1316. Alternatively, or in addition, the injection device 1330 may include an injection machine that controls the pressure, amount, and/or flow rate of fluid being injected through the fluid port 1324 of the handle 1320 (or through the sheath fluid port 1328 of the sheath 1316), as known to one of ordinary skill in the art.

Now with reference to FIGS. 29 and 30, fluid may flow through the lumen 1322 of the delivery catheter 1318, as discussed above, and through the hub 1312 (and components associated therewith) of the medical tool 1300, the medial device 1300 being positioned in the LAA 1005. As the fluid exits the hub 1312 of the medical tool 1300, as depicted by arrows 1332 in FIG. 29, the fluid mixes with the blood in the LAA 1005. Due to the occluder portion 1306 having the substantially non-permeable material associated therewith, if the medical tool 1300 is properly positioned in the LAA 1005, the fluid may be substantially maintained within the LAA 1005, but for general seeping around the outer periphery 1314 of the medical tool 1300 without an identifiable source or gap. The meaning of substantially maintaining fluid in the LAA means substantially containing, sustaining and/or retaining the fluid in the LAA, except for general seeping along the outer periphery 1314. With respect to FIGS. 30, 30A, and 30B, the flow path (depicted by arrows 1310 in FIG. 30) of the fluid flowing from the delivery catheter 1318 and through the hub 1312 will now be described. The flow path 1310 extends through the lumen 1322 of the delivery catheter 1318 and surrounds and moves along a length of the actuator shaft 1326 and the delivery catheter 1318. Section 30C identified in FIG. 30 may be substantially similar to that described and depicted in FIG. 28A, depicting the delivery catheter 1318 defining the lumen 1322 with the actuator shaft 1326 positioned therethrough. The flow path 1310 continues to advance along the collet 1336 and then outward into a space 1334 or channel defined between the collet fingers 1338 (see FIGS. 30 and 30A). The flow path 1310 continues advancing between an inner distal connector 1340 and the delivery catheter 1318 and then between the inner distal connector 1340 and the medical tool 1300 (only the hub 1312 is shown), as depicted in FIGS. 30 and 30A. The hub 1312 includes a guide ring 1342 that may be embedded within the inner diameter or bore 1344 defined in the hub 1312 itself. Such guide ring 1342 includes apertures 1346 (see FIG. 30B) defined therein through which the flow path 1310 extends. Such apertures 1346 may include an annular space or partial annular configuration or space. Alternatively, or in addition, the inner diameter or bore may include an annular protrusion, instead of the guide ring 1342, such that the bore 1344 between the annular protrusion and the inner distal connector 1340 may define an annular space through which the flow path 1310 extends (instead of the apertures 1346). Once the flow path 1310 continues through the apertures 1346 or annular space and past the guide ring 1342 or annular protrusion in the bore 1344, the flow path 1310 continues advancing through the bore 1344 of the hub 1312 and distally over the inner distal connector 1340. The inner distal connector 1340 may include threads along an inner diameter thereof to couple to threads on a proximal end of the anchor hub 1350. The flow path 1310 continues advancing through the hub 1312 until exiting the hub 1312, as depicted with arrows 1332, so that fluid 1304 can enter the LAA 1005 on the distal side of the medical tool 1300, as shown in FIG. 29. With this arrangement, each of the handle 1320, delivery catheter 1318 and hub 1312 of the medical tool 1300 includes a common, shared, or corresponding flow path 1310 that facilitates a fluid 1304 to exit a distal side of the medical tool 1300.

Figure 31:
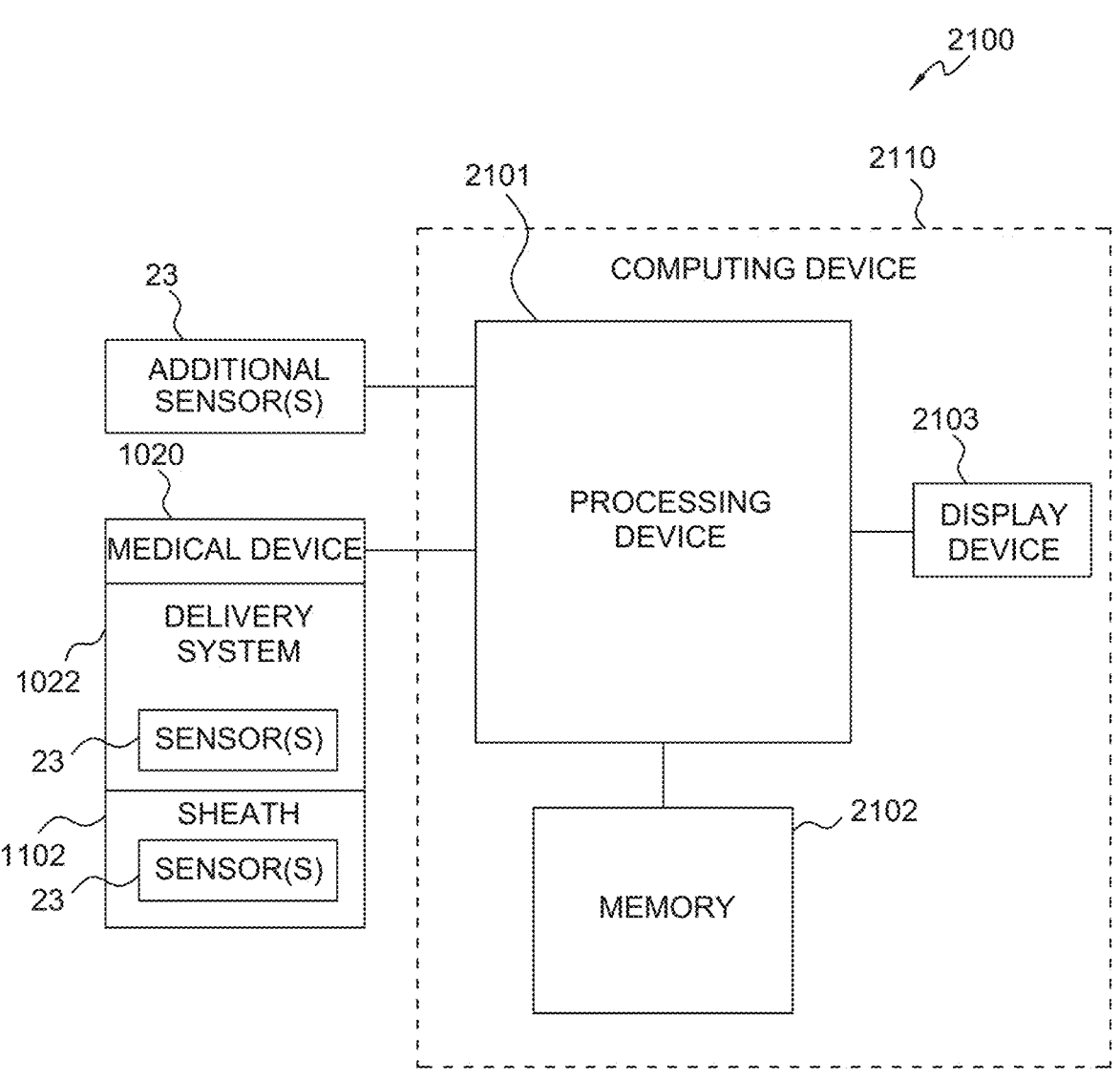
FIG. 31 is a block diagram illustrating example components of a medical system for occlusion detection according to the second exemplary embodiment of the present invention.

With reference to FIG. 31 a system 2100 for occlusion detection may comprise a sheath 1102, a delivery system 1022, a medical tool 1020, at least one sensor 23, as described above, and a processing device 2101. The system 2100 may further comprise a memory 2102 and a display device 2103. The processing device 2101, memory 2102 and display device 2103 may be part of a computing device 2110. The system 2100 may optionally comprise additional sensors located throughout the system. Computing device 2110 may also include an I/O interface.

The at least one sensor 23 may be configured to detect at least one physical characteristic of blood. As noted above, the at least one sensor 23 is located on the distal portion of the sheath 1102. Additionally or alternatively, the at least one sensor 23 may be located on the distal end of the delivery catheter. Additionally or alternatively, the at least one sensor 23 may be located on a proximal end of the delivery catheter. Additional sensors may be located elsewhere throughout the system. For example, as shown in FIGS. 11, 11A, 11B, 12, 14, 16C, 28 and 29, sensor are located in exemplary positions including on exterior of the occlude portion 1024, on the interior of the occlude portion 1024. Although not shown in the figures, one or more sensors 23 may be located on the exterior or interior of the anchor portion 1026, as well.

The at least one sensor 23 may comprise a temperature sensor and the at least one characteristic comprises temperature. Alternatively, or in addition, the at least one sensor 23 comprises a first electrode and a second electrode and the at least one characteristic may comprise bipolar electrical impedance. Alternatively, or in addition, the at least one sensor 23 may comprise a first electrode and a second electrode and the second electrode may a reference electrode, and the at least one characteristic may comprise unipolar electrical impedance. Alternatively, or in addition, the at least one sensor 23 may comprise a pH sensor and the at least one characteristic may comprise pH.

Processing device 2101 may include one or more processors. The processing device 2101 may be configured to process the blood characteristic data acquired from the at least one sensor 23. The processing device 2101 may be further configured to record the at least one characteristic of blood over time.

Display device 2103 may include one or more displays configured to display the at least one characteristic of blood data over time. The display device 2103 may display the at least one characteristic of blood over time in a meaningful way such as a chart or a graph. The display device 2103 may be further configured to display a baseline characteristic of blood next to, or on top of, the at least one characteristic of blood over time. The processing device 2101 may be further configured to determine whether an occlusion is present by comparing at least one blood characteristic data over time to a baseline of the at least one characteristic of blood. Additionally or alternatively, the processing device 2101 may be further configured to determine whether an occlusion is present in the LAA based on how quickly the at least one characteristic of blood returns to its original value. Additionally or alternatively, the processing device 2101 may be further configured to record the at least one blood characteristic of the LAA and the at least one characteristic of blood of the left atrium, and then compare the at least one characteristic of blood of the LAA and the at least one characteristic of blood of the left atrium. Alternatively, or in addition, the the processing device 2101 may be further configured to determine whether an occlusion is present in the LAA using the comparison of the at least one characteristic of blood of the LAA and the at least one characteristic of blood of the left atrium; and determine whether an occlusion is present in the left atrium using the at least one characteristic of blood of the LAA and the at least one characteristic of blood of the left atrium.

The at least one sensor 23 may be in wired or wireless communication with processing device 2101. Display device 2103 may also be in wired or wireless communication with processing device 2101.

The system may further comprise a memory 2102. Memory 2102 may comprise storage for storing data. The memory 2102 may be configured to store the measurements of the at least one characteristic of blood. Alternatively, or in addition, the memory 2102 may be configured to store the baseline of the at least one characteristic of blood. The memory 2102 may include any volatile and/or non-volatile memory, such as random-access memory or a hard disk drive.

Figure 32:
FIG. 32 is a flowchart illustrating a method of occlusion detection according to the second exemplary embodiment of the present invention; and, FIG. 33 is a flowchart illustrating a method of determining a baseline measurement of a patient for occlusion detection according to the second exemplary embodiment of the present invention.
Figure 32:
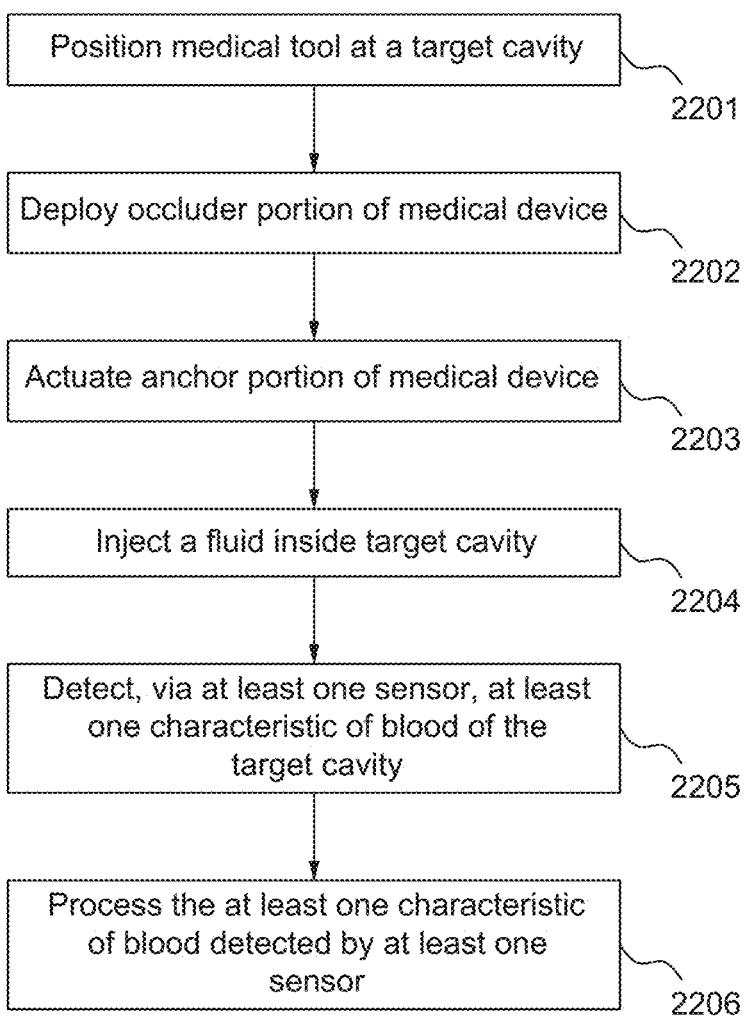

With reference to FIG. 32, at step 2201 the medical tool 1020 may be positioned within an organ of a patient at a target location, such as the heart, as described above. At step 2202, the occluder portion of the medical tool may be deployed, as described above. At step 2203, upon the occluder portion being in an expanded, deployed position, the anchor portion 1026 of the medical tool 1020 may go from a retracted position to an anchor deployed position having tines, as described above. At step 2204, a fluid may be injected through the delivery catheter, in a cavity, as described above. The fluid may be a coolant. The fluid may be saline. Additionally or alternatively, the fluid is glucose at a low temperature. The injected fluid may change the at least one characteristic of blood inside the target cavity. Therefore, changes in the at least one characteristic of blood may indicate the presence or absence of an occlusion. At step 2205, at least one characteristic of blood is detected via at least one sensor 23. At step 2206, the processing device 2101 processes the at least one characteristic of blood data detected by the at least one sensor 23. The presence or absence of an occlusion is determined by the at least one characteristic of blood. For example, the at least one characteristic of blood may change after the fluid is injected into the target cavity due to fluid dilation. Fluid dilation may cause changes in characteristics of the blood, including but not limited to temperature, impedance and pH. As such, changes in the characteristics of the blood may indicate an occlusion, partial occlusion or full occlusion. Fluid dilation changes may be observed by a physician on the display 2103, and the physician may determine the presence or absence of an occlusion based on the changes. Additionally or alternatively, the processing device 2101 may be further configured to determine the presence or absence of an occlusion as described in more detail below.

The at least one sensor 23 may be a temperature sensor and the at least one characteristic of blood is temperature. Alternatively or in addition, the at least one sensor 23 may be a first electrode and a second electrode, and the at least one characteristic is bipolar electric impedance. Alternatively or in addition, the at least one sensor 23 may be a first electrode and a second electrode, the second electrode being a reference electrode, and the at least one characteristic being unipolar electrical impedance. Alternatively or in addition, the at least one sensor 23 is a pH sensor and the at least one characteristic is pH.

Figure 33:
Figure 33:
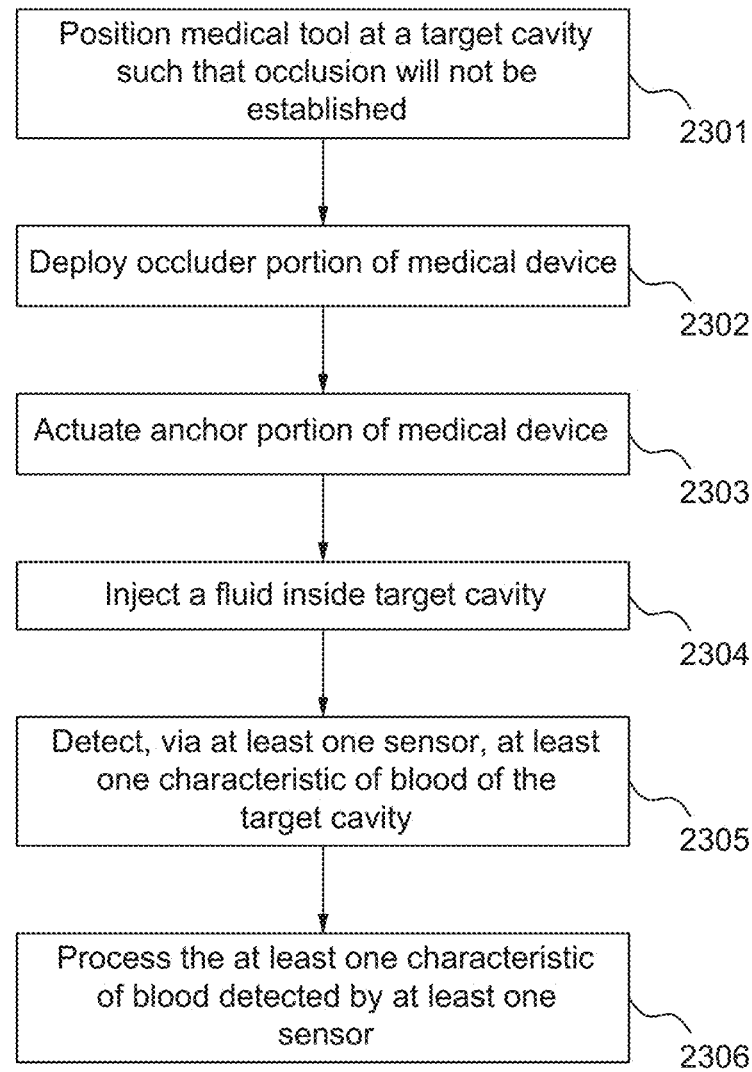

With reference to FIG. 33, in accordance with the second exemplary embodiment, a baseline measurement of a patient at the relevant anatomic location may be determined through method 2300 and then used as a reference to determine if there is a full or partial occlusion. At step 2301 the medical tool 1020 may be positioned within an organ of a patient at a target location, as described above. However, the medical tool 1020 is positioned such that there will not be full occlusion. At step 2302, the occluder portion of the medical tool may be deployed, as described above. At step 2303, upon the occluder portion being in an expanded, deployed position, the anchor portion 1026 of the medical tool 1020 may go from a retracted position to an anchor deployed position having tines, as described above. At step 2304, a fluid may be injected through the delivery catheter, into a target cavity, as described above. At step 2305, at least one characteristic of blood is detected via at least one sensor 23. At step 2306, the processing device 2101 processes the at least one characteristic of blood data detected by the at least one sensor 23 and establishes the data as a baseline measurement of the at least one characteristic of blood.

Alternatively or in addition, the method may further comprise recording, via the processing device 2101, the measurements of the at least one characteristic of blood over time. The method may further comprise storing, in the memory 2102, measurements of the at least one blood characteristic over time.

Determining a baseline characteristic of blood is not necessary for identification of an occlusion using system 2100 of the present disclosure. For example, in an embodiment, the at least one characteristic of blood of the LAA is measured before injection of the fluid. The fluid is then injected and the at least one characteristic of blood is observed over a period of time. If the at least one characteristic of blood returns to the original value relatively quickly, no occlusion is assumed. Similarly, if the at least one characteristic of blood takes a relatively long time to return to its original value, occlusion is assumed. The display may be configured to display the original measurement of the at least one characteristic of blood and the at least one characteristic of blood over time after injection of the fluid so that the physician may determine whether there is an occlusion. Additionally or alternatively, the processing device 2101 may be further configured to compare the original measurement of the at least one characteristic of blood and the at least one characteristic of blood over time after injection of the fluid to determine if an occlusion is present.

The tines of the anchor portion 1026 may be configured to engage tissue with the LAA and the left atrium, as described above, and method 2100 may be performed twice: once on the left atrium and once on the LAA. The LAA measurement and the left atrium measurement may be performed simultaneously. The display device 2103 may be configured to display the at least one characteristic of blood of the left atrium and the at least one characteristic of blood of the LAA so that the physician may compare the measurements to determine whether there is occlusion. For example, if the at least one characteristic of blood changes in a similar manner inside the LAA and the left atrium, no occlusion is assumed. If the at least one characteristic of blood changes in a different manner inside the LAA and the left atrium, occlusion is assumed. Additionally or alternatively, the processing device 2101 may be configured to compare the at least one characteristic of blood of the left atrium and the at least one characteristic of blood of the LAA and determine whether there is an occlusion. The methods described and illustrated in relation to FIGS. 32 and 33 are also algorithms that can be utilized by a skilled software engineer to generate the requisite step-by-step computer codes for implementation of the overall method in a computer system (e.g., a general-purpose computer or a special purpose computer such as the Carto system) so that embodiments described herein can be used to detect occlusion.

It should be understood that many variations are possible based on the disclosure of the first and second exemplary embodiments herein. Although features and elements are described above in particular combinations, each feature or element can be used alone without the other features and elements or in various combinations with or without other features and elements.

What is claimed is:

1. A method of occlusion detection comprising:
   (a) determining, via a processor, an original value of at least one characteristic of blood of a patient;
   (b) positioning a medical tool coupled to a distal portion of a distal end of a delivery catheter at a target cavity within the patient, the medical tool comprising an expandable balloon, and at least one sensor;
   (c) expanding the expandable balloon when the balloon is positioned at the target cavity to thereby establish an occluded area and a leakage area of the target cavity, the expandable balloon having a distal end and a proximal end defining a longitudinal axis, and a membrane formed of a plurality of irrigation pores;
   (d) introducing a fluid into the target cavity;
   (e) detecting, via a first sensor of the at least one sensor, a first updated value of the at least one characteristic of blood in the occluded area;
   (f) detecting, via a second sensor of the at least one sensor, a second updated value of the at least one characteristic of blood in the leakage area, the second sensor being positioned on an outer surface of the expandable balloon to thereby contact the blood;
   (g) processing, via a processor, the first and second updated values of the at least one characteristic of blood; and
   (h) determining, via the processor, a time from when the fluid is introduced into the target cavity to when the first and second updated values of the at least one characteristic of blood return to the original value taken prior to the step of positioning the medical tool in the target cavity, and
   a presence or absence of an occlusion being determined by the updated values of the at least one characteristic of blood from each of the first and second sensor, the original value, and a baseline of the at least one characteristic of blood that has no occlusion.

2. The method of claim 1, said step of introducing the fluid into the target cavity further comprising introducing the fluid through the plurality of irrigation pores of said expandable balloon.

3. The method of claim 1, said step of introducing the fluid into the target cavity further comprising introducing the fluid through an inner lumen of the delivery catheter.

4. The method of claim 1, the target cavity comprising one of a pulmonary vein of a heart or a left atrium of the heart.

5. The method of claim 1, the fluid comprising a coolant.

6. The method as in claim 1, further comprising determining the baseline of the at least one characteristic of blood by:
   positioning the medical tool at a second target cavity within the patient such that there will be no occlusion;

expanding the expandable balloon when the expandable balloon is positioned at the second target cavity;

introducing a fluid into the second target cavity; and detecting, via the at least one sensor, at least one characteristic of blood in the second target cavity, and processing, via the processor, data of the at least one characteristic of blood and establishing the data as a baseline measurement, the at least one characteristic of blood being compared to the baseline measurement.

7. The method of claim 6, within the determining of the baseline, said step of introducing a fluid into the second target cavity further comprising introducing the fluid through the plurality of irrigation pores of the expandable balloon.

8. The method of claim 6, within the determining of the baseline, said step of introducing a fluid into the second target cavity further comprising injecting the fluid through an inner lumen of the delivery catheter.

9. The method as in claim 6, further comprising determining, via the processor, whether the occlusion is present in the target cavity by comparing the baseline measurement and the at least one blood measurement detected by the at least one sensor over time.

10. The method as in claim 1, further comprising executing, via the processor, an algorithm based on the at least one blood characteristic to determine the presence or absence of an occlusion, or a number indicating an extent of the occlusion.

11. The method of claim 1, the at least one sensor comprising a chemical composition sensor and the at least one characteristic of blood being a chemical composition.

12. A method of occlusion detection comprising:

(a) determining, via a processor and at least one sensor, an original value of at least one characteristic of blood of a patient;

(b) positioning a medical tool coupled to a distal portion of a distal end of a delivery catheter at a target cavity within the patient, the medical tool comprising an expandable balloon having an electrode, and the at least one sensor;

(c) after determining the original value, expanding the expandable balloon when the balloon is positioned at the target cavity, the expandable balloon having a distal end and a proximal end defining a longitudinal axis, and a membrane formed of a plurality of irrigation pores;

(d) introducing a fluid into the target cavity;

(e) detecting, via the at least one sensor, an updated value of the at least one characteristic of blood in the target cavity;

(f) processing, via a processor, the updated value of the at least one characteristic of blood; and (g) determining, via the processor, a time from when the fluid is introduced into the target cavity to when the updated value of the at least one characteristic of blood returns to the original value taken prior to the step of positioning the medical tool in the target cavity, and determining a presence or absence of an occlusion by the updated value of the at least one characteristic of blood and a time taken for the updated value of the at least one characteristic of blood to return to the original value, the original value including a baseline of the at least one characteristic of blood that has no occlusion.

* * * * *